(12) United States Patent
Cardozo et al.

(10) Patent No.: US 9,261,497 B2
(45) Date of Patent: Feb. 16, 2016

(54) METHOD OF TREATING CANCER WITH MODULATORS OF SCFSKP2

(71) Applicants: Timothy Cardozo, New York, NY (US); Michele Pagano, New York, NY (US); Lily Wu, Freeport, NY (US); Leslie I. Gold, New York, NY (US)

(72) Inventors: Timothy Cardozo, New York, NY (US); Michele Pagano, New York, NY (US); Lily Wu, Freeport, NY (US); Leslie I. Gold, New York, NY (US)

(73) Assignee: New York University, New York, NY (US)

( * ) Notice: Subject to any disclaimer, the term of this patent is extended or adjusted under 35 U.S.C. 154(b) by 9 days.

(21) Appl. No.: 14/055,501

(22) Filed: Oct. 16, 2013

(65) Prior Publication Data

US 2014/0142120 A1    May 22, 2014

Related U.S. Application Data

(60) Provisional application No. 61/714,540, filed on Oct. 16, 2012, provisional application No. 61/804,531, filed on Mar. 22, 2013.

(51) Int. Cl.
| | | |
|---|---|---|
| *C07D 513/04* | (2006.01) | |
| *G01N 33/50* | (2006.01) | |
| *C07D 239/36* | (2006.01) | |
| *C07D 417/06* | (2006.01) | |
| *C07D 249/12* | (2006.01) | |

(Continued)

(52) U.S. Cl.
CPC .......... *G01N 33/5011* (2013.01); *A61K 31/341* (2013.01); *A61K 31/4015* (2013.01); *A61K 31/4196* (2013.01); *A61K 31/426* (2013.01); *A61K 31/427* (2013.01); *A61K 31/4439* (2013.01); *A61K 31/513* (2013.01); *A61K 31/519* (2013.01); *C07C 251/80* (2013.01); *C07D 207/44* (2013.01); *C07D 239/36* (2013.01); *C07D 249/12* (2013.01); *C07D 277/34* (2013.01); *C07D 307/54* (2013.01); *C07D 417/06* (2013.01); *C07D 471/04* (2013.01); *C07D 513/04* (2013.01); *G01N 33/574* (2013.01); *G01N 2500/02* (2013.01)

(58) Field of Classification Search
CPC ............ A61K 31/341; A61K 31/4196; A61K 31/426; A61K 31/427; A61K 31/4439; A61K 31/513; A61K 31/519
See application file for complete search history.

(56) References Cited

U.S. PATENT DOCUMENTS

| | | |
|---|---|---|
| 6,201,127 B1 | 3/2001 | Copp et al. |
| 7,105,554 B2 | 9/2006 | Orchard et al. |

(Continued)

FOREIGN PATENT DOCUMENTS

| | | | |
|---|---|---|---|
| WO | 2004/006906 A2 | 1/2004 | |
| WO | WO 2008/130619 | * 10/2008 | |

OTHER PUBLICATIONS

Sausville et al. (Cancer Research, 2006, vol. 66, pp. 3351-3354).*

(Continued)

*Primary Examiner* — Savitha Rao
*Assistant Examiner* — Angela Brown-Pettigrew
(74) *Attorney, Agent, or Firm* — LeClairRyan, a Professional Corporation

(57) ABSTRACT

The present invention relates to pharmaceutical compositions comprising a compound and a pharmaceutically acceptable carrier. The present invention is also directed to a method of treating cancer in a subject. Also disclosed are methods of inhibiting SCF-Skp2 activity and a method of identifying inhibitors of SCF-Skp2 activity.

2 Claims, 32 Drawing Sheets

(51) Int. Cl.
| | |
|---|---|
| C07D 471/04 | (2006.01) |
| C07D 207/44 | (2006.01) |
| C07D 277/34 | (2006.01) |
| C07C 251/80 | (2006.01) |
| C07D 307/54 | (2006.01) |
| G01N 33/574 | (2006.01) |
| A61K 31/341 | (2006.01) |
| A61K 31/4015 | (2006.01) |
| A61K 31/4196 | (2006.01) |
| A61K 31/426 | (2006.01) |
| A61K 31/427 | (2006.01) |
| A61K 31/4439 | (2006.01) |
| A61K 31/513 | (2006.01) |
| A61K 31/519 | (2006.01) |

(56) References Cited

U.S. PATENT DOCUMENTS

2009/0054312 A1  2/2009 Wolf et al.
2011/0269954 A1  11/2011 Cho et al.

OTHER PUBLICATIONS

Johnson et al. (British J. of Cancer, 2001, 84(10):1424-1431).*
Cardozo et al., "Wrenches in the Works: Drug Discovery Targeting the SCF Ubiquitin Ligase and APC/C Complexes," BMC Biochem. 8(Suppl I):S9 (2007).
Wu, "Structure-Based Design of SCF-Skp2 Inhibitors," Pharmacology Work in Progress Oral Presentation (2009).
Wu, "Novel Therapeutic Strategies Targeting the SCF Family of E3 Ligases," Oral Presentation at NYU Cancer Institute 6th Annual Translational Research Retreat (2009).
Wu et al., "Specific Small Molecule Inhibitors of Skp2-Mediated p27 Degradation," Chem. Biol. 19(12):1515-1524 (2012).
Wu, "Targeting the Ubiquitin Proteasome System: Structure-Based Design of Novel Inhibitors," Hematology Seminar (2010).
Wu et al., "Structure-Based Design of Inhibitors Against the SCF E3 Ligases," Aided Drug Design Seminar, Poster (2010).
Huang et al., "Estrogen and Progesterone Regulate p27kip1 Levels via the Ubiquitin-Proteasome System: Pathogenic and Therapeutic Implications for Endometrial Cancer," PLOS One 7(9):e4607 (2012).
Chan et al., "Pharmacological Inactivation of Skp2 SCF Ubiquitin Ligase Restricts Cancer Stem Cell Traits and Cancer Progression," Cell 154:556-568 (2013).
Rico-Bautista et al., "Skipping Cancer: Small Molecule Inhibitors of SKP2-Mediated p27 Degradation," Chem. Biol. 19:1497-1498 (2012).
Coulibaly et al., "Synthesis of New N,N'-Bis(5-arylidene-4-oxo-4,5-dihydrothiazolin-2-yl)piperazine Derivatives Under Microwave Irradiation and Preliminary Biological Evaluation," Sci. Pharm. 80(4):825-836 (2012).
International Search Report and Written Opinion for Patent Application No. PCT/US2013/065256 (Apr. 14, 2014).

* cited by examiner

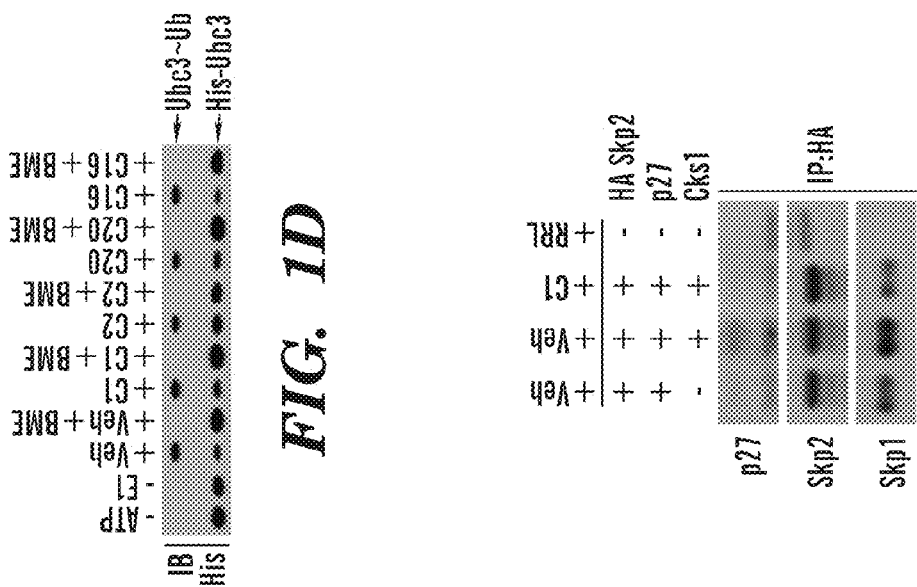
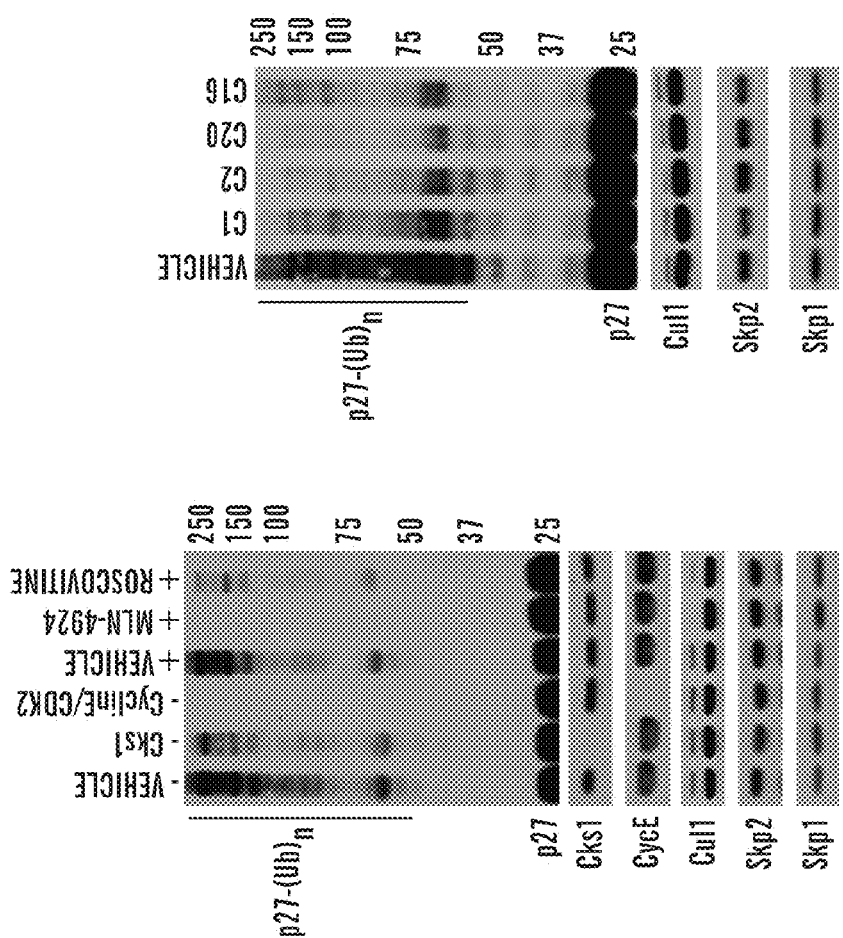
FIG. 1B  FIG. 1C  FIG. 1D  FIG. 1E

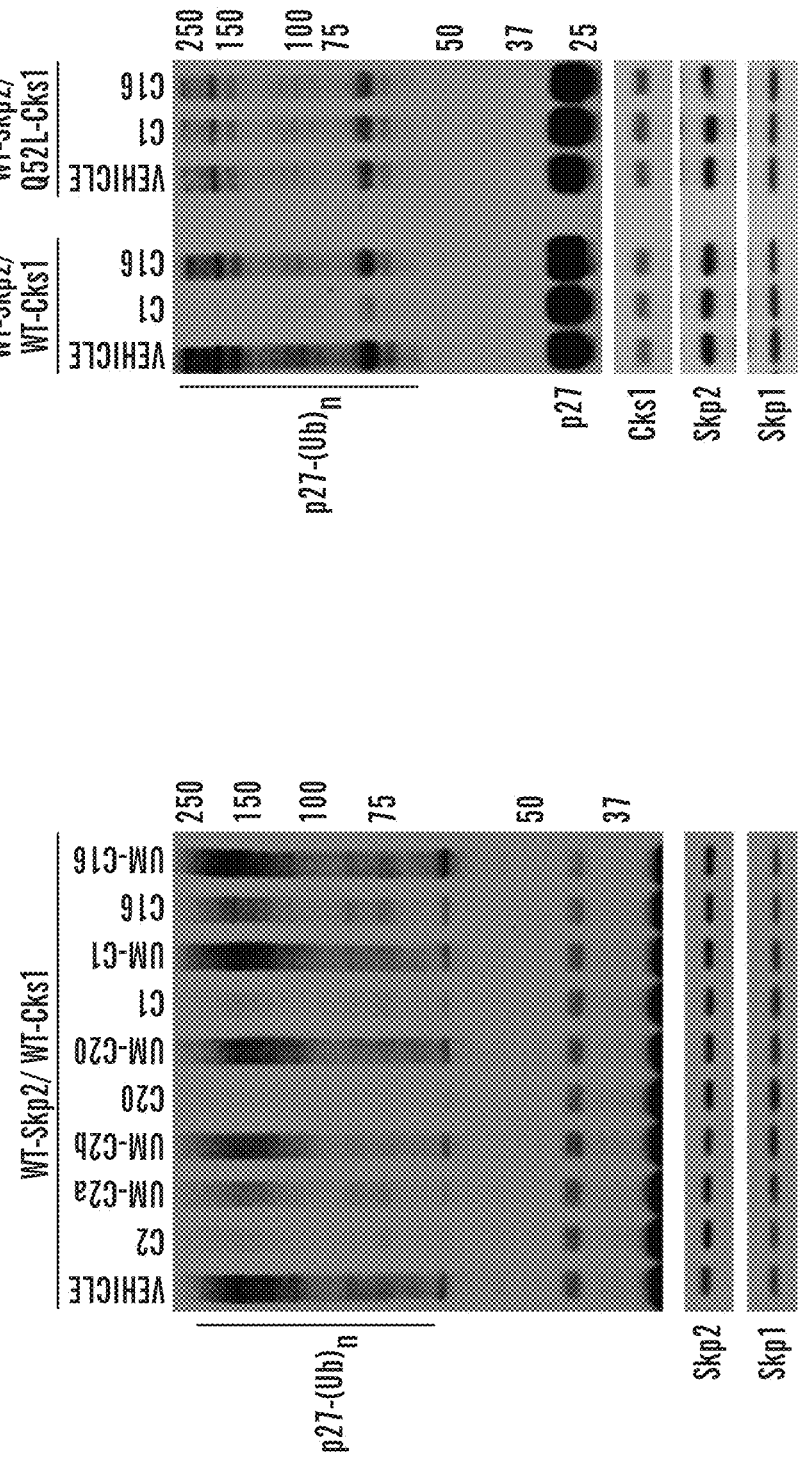

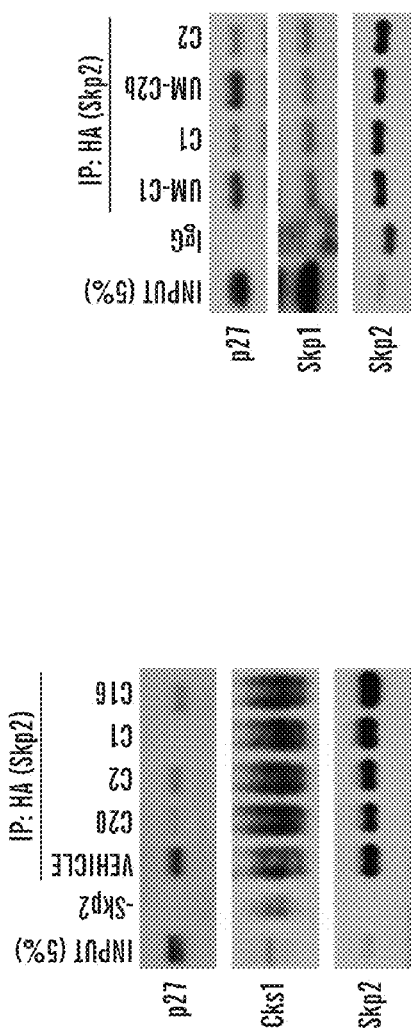
FIG. 3B
FIG. 3C
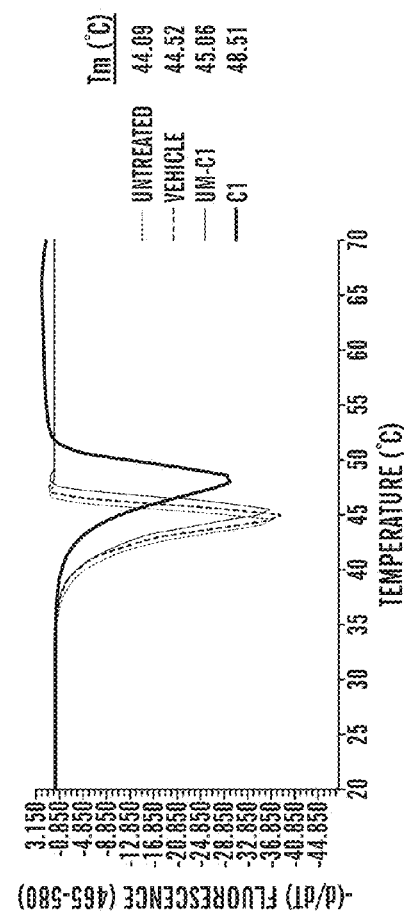
FIG. 3D

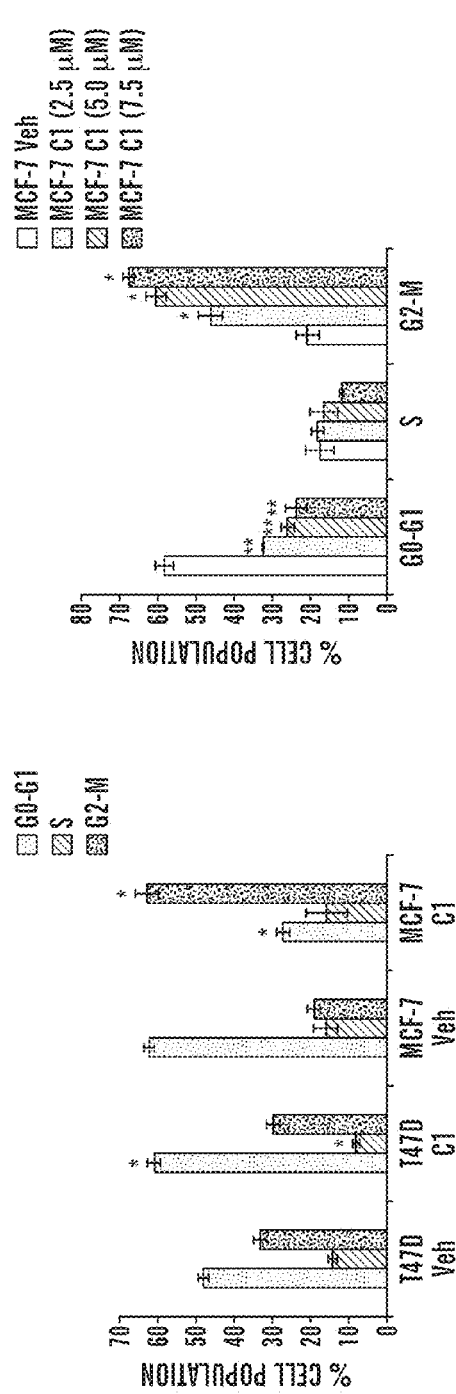
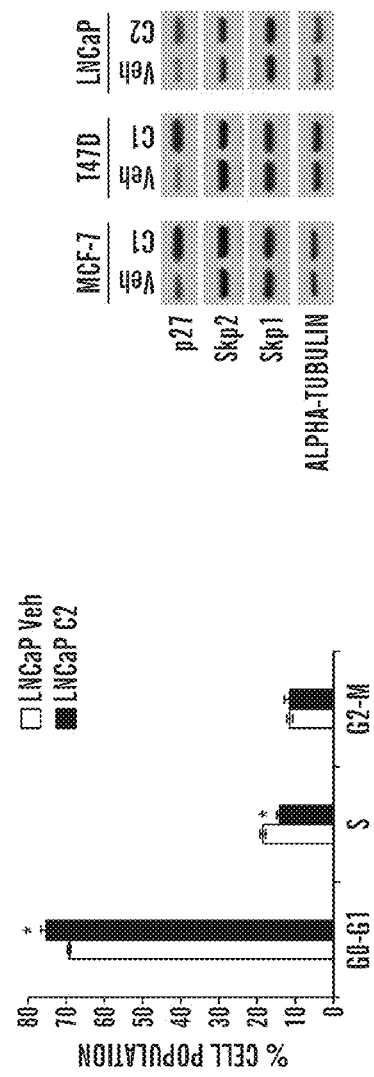
FIG. 5C
FIG. 5D
FIG. 5E

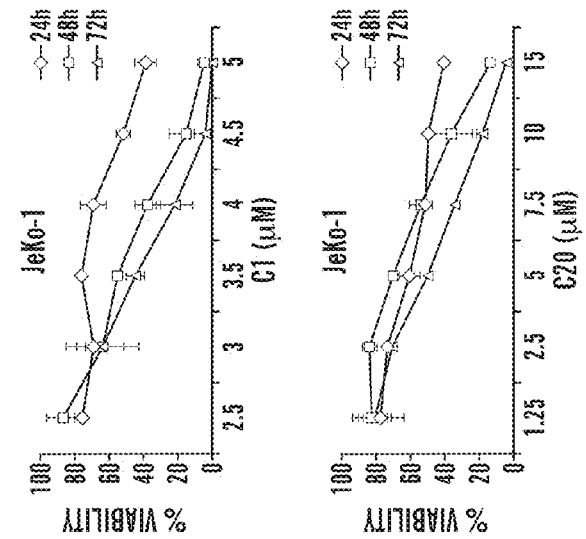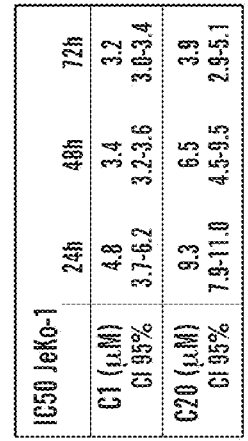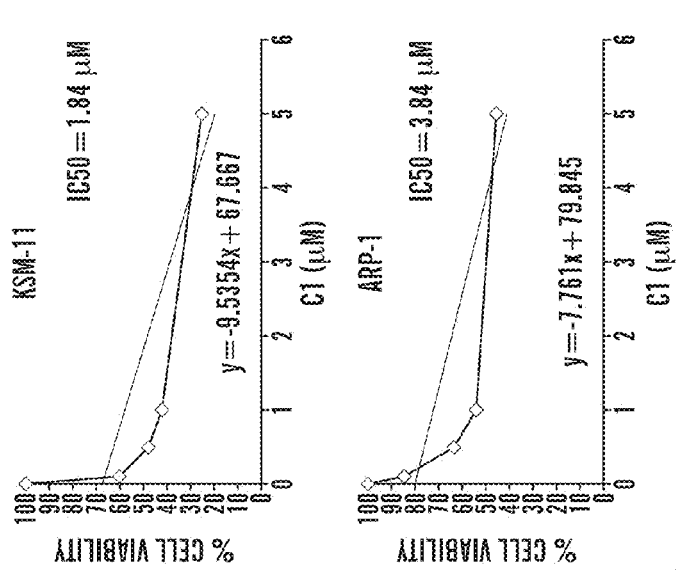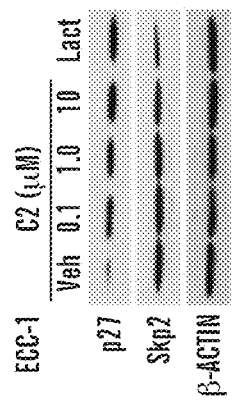
FIG. 10A
FIG. 10B
FIG. 10C

PRIMERS USED FOR REAL-TIME RT-PCR

| PRIMER NAME | ACCESSION NUMBER | SEQUENCE NEW SHEET |
|---|---|---|
| p27 F | NM_004064 | 5'-CTTGCCCGAGTTCTACTACAGAC-3' |
| p27 R | | 5'-CAAATGCGGTGTCCTCAGAGTTAG-3' |
| Skp2 F | NM_005983 | 5'-TCAACTACCTCCAACACCTATCAC-3' |
| Skp2 R | | 5'-GGTACCATCTGGCACGATTCC-3' |
| Cks1 F | NM_001826 | 5'-GAGTATCGACATGTCATGCTGC-3' |
| Cks1 R | | 5'-TCTTTGGTTTCTTGGGTAGT-3' |
| Cdh1 F | NM_016263 | 5'-GTCCAAGCACGCCAACGAGCTGGTGA-3' |
| Cdh1 R | | 5'-GACACAGACTCCTTTGTCGAACGG-3' |
| PR F | NM_000926 | 5'-GGTCTACCCGCCCTATCTCA-3' |
| PR R | | 5'-GGCTTGGCTTTCATTTGGAA-3' |
| glycodelin F | NM_002571 | 5'-CACGCTGCTCGATACTGACTACGAC-3' |
| glycodelin R | | 5'-TGGAGGCGGAGGTGAGCTAGAAA-3' |
| actin F | NM_001101 | 5'-ATCATGTTTGAGACCTTCAA-3' |
| actin R | | 5'-CATCTCTTGCTCGAAGTCCA-3' |

FIG. 19

METHOD OF TREATING CANCER WITH MODULATORS OF SCFSKP2

This application claims the benefit of U.S. Provisional Patent Application Ser. No. 61/714,540, filed Oct. 16, 2012, and U.S. Provisional Patent Application Ser. No. 61/804,531, filed Mar. 22, 2013, both of which are hereby incorporated by reference in their entirety.

This invention was made with government support under NIH grant numbers DP2 OD004631 and T32 HL 007151-30. The government has certain rights in the invention.

FIELD OF THE INVENTION

The present invention is directed to pharmaceutical compositions and treatment of cancer or other diseases or disorders associated with SCF-Skp2 activity.

BACKGROUND OF THE INVENTION

The ubiquitin proteasome system ("UPS") is essential for the turnover of almost all cellular proteins, maintaining homeostatic levels in normal cells while controlling levels of oncogenes and tumor suppressors in transformed cells. In an ATP-dependent process, ubiquitin is transferred from the ubiquitin-activating enzyme E1 to the ubiquitin-conjugating enzyme E2, and covalently attached via an isopeptide linkage to a target protein bound to a ubiquitin ligase E3 (Ciechanover, "Proteolysis: from the lysosome to ubiquitin and the proteasome,". *Nat. Rev. Mol. Cell. Biol.* 6:79-87 (2005)). Chains of four or more ubiquitin domains trigger degradation by the 26S proteasome.

FDA approval of the proteasome inhibitor Bortezomib (Velcade™, Millenium Pharmaceuticals Inc.) established the UPS as a validated target for treatment of multiple myeloma and mantle cell lymphoma (Bross et al., "Approval Summary for Bortezomib for Injection in the Treatment of Multiple Myeloma," *Clin. Cancer Res.* 10:3954-3964 (2004) and Kane at al., "Bortezomib for the Treatment of Mantle Cell Lymphoma," *Clin. Cancer Res.* 13:5291-5294 (2007)). Yet, advances in the clinical use of Bortezomib for solid tumors are lacking, resistance is developing, and peripheral neuropathy is a major side effect (Argyriou et al., "Bortezomib-induced Peripheral Neuropathy in Multiple Myeloma: A Comprehensive Review of the Literature," *Blood* 112:1593-1599 (2008) and Orlowski et. al., "Proteasome Inhibitors In Cancer Therapy: Lessons from the First Decade," *Clin. Cancer Res.* 14:1649-1657 (2008)). Recent investigations are now focused on inhibiting UPS proteins upstream of the proteasome (Ceccarelli et al., "An Allosteric Inhibitor of the Human Cdc34 Ubiquitin-conjugating Enzyme," *Cell* 145: 1075-1087 (2012); Orlicky et al., "An Allosteric Inhibitor of Substrate Recognition by the SCF(Cdc4) Ubiquitin Ligase," *Nat. Biotechnol.* 28:733-737 (2010); and Soucy et al., "An Inhibitor of NEDD8-activating Enzyme as a New Approach to Treat Cancer," *Nature* 458:732-736 (2009)). Of particular interest are inhibitors specific to E3 ligases in the hope of reducing off-target effects.

The Skp1-Cullin1-F-box ("SCF") family is a multi-protein RING-finger E3 ligase that drives each stage of the cell cycle by controlling the protein levels of cyclins and cyclin-dependent kinase inhibitors ("CKI's") (Cardozo et al., "The SCF Ubiquitin Ligase: Insights into a Molecular Machine," *Nat. Rev. Mol. Cell Biol.* 5:739-751 (2004)). Through a coordinated repertoire of protein-protein interactions, the scaffold protein Cullin-1 ("Cul1") binds both the Ring-box protein 1 ("Rbx1"), recruiting the E2-ubiquitin complex, and the adaptor protein Skp1, recruiting the F-Box E3 ligase (Petroski et al., "Function and Regulation of Cullin-RING Ubiquitin Ligases," *Nat. Rev. Mol. Cell Biol.* 6:9-20 (2005)). The F-box family members dictate the substrate by binding a degron that is usually, but not always, post-translationally modified (Skowyra et al., "F-box Proteins are Receptors that Recruit Phosphorylated Substrates to the SCF Ubiquitin-ligase Complex," *Cell* 91:209-219 (1997)).

The F-box protein S-phase kinase-associated protein 2 ("Skp2") is overexpressed in human cancers and implicated in multiple murine models (Frescas et al., "Deregulated Proteolysis by the F-box Proteins SKP2 and Beta-TrCP: Tipping the Scales of Cancer," *Nat. Rev. Cancer* 8:438-449 (2008); Lin et al., "Skp2 Targeting Suppresses Tumorigenesis by Arf-p53-independent Cellular Senescence," *Nature* 464:374-379 (2010); and Nakayama et al., "Ubiquitin Ligases: Cell-cycle Control and Cancer," *Nat. Rev. Cancer* 6:369-381 (2006)). SCF-Skp2 degrades known tumor suppressors CKIs p27, p21, and p57 (Carrano et al., "SKP2 is Required for Ubiquitin-mediated Degradation of the CDK Inhibitor p27," *Nat. Cell. Biol.* 1:193-199 (1999); Kamura et al., "Degradation of p57Kip2 Mediated by SCFSkp2-dependent Ubiquitylation," *Proc. Natl. Acad. Sci. USA* 100:10231-10236 (2003); and Yu et al., "Human CUL-1 Associates with the SKP1/SKP2 Complex and Regulates p21(CIP1/WAF1) and Cyclin D Proteins," *Proc. Natl. Acad. Sci. USA* 95:11324-11329 (1998)). Recognition of the p27 degron is unique, being bound by a complex consisting of Skp2 and an accessory protein, Cdc kinase subunit 1 (Cks1), after phosphorylation of Thr-187 by CyclinE-CDK2 (Ganoth et al., "The Cell-cycle Regulatory Protein Cks1 is Required for SCF(Skp2)-mediated Ubiquitinylation of p27," *Nat. Cell Biol.* 3:321-324 (2001); Montagnoli et al., "Ubiquitination of p27 is Regulated by Cdk-dependent Phosphorylation and Trimeric Complex Formation," *Genes Dev.* 13:1181-1189 (1999); and Tsvetkov et al. "p27(Kip1) Ubiquitination and Degradation is Regulated by the SCF(Skp2) Complex through Phosphorylated Thr187 in p27," *Curr. Biol.* 9:661-664 (1999)). Additional non-phosphorylated residues of the p27 degron reinforce this trimeric complex for a high rate of p27 ubiquitylation (Hao et al., "Structural Basis of the Cks1-dependent Recognition of p27(Kip1) by the SCF(Skp2) Ubiquitin Ligase," *Mol. Cell* 20:9-19 (2005); Sitry et al., "Three Different Binding Sites of Cks1 are Required for p27-ubiquitin Ligation," *J. Biol. Chem.* 277:42233-42240 (2002); Wang et al., "A Negatively Charged Amino Acid in Skp2 is Required for Skp2-Cks1 Interaction and Ubiquitination of p27Kip1," *J. Biol. Chem.* 278:32390-32396 (2003); and Wang et al., "Molecular and Biochemical Characterization of the Skp2-Cks1 Binding Interface," *J. Biol. Chem.* 279:51362-51369 (2004)).

Small molecule inhibitors have been successfully developed against E3 ligase-substrate interfaces, including Mdm2-p53 and IAPs-caspases (Vassilev et al., "In Vivo Activation of the p53 Pathway by Small-molecule Antagonists of MDM2," *Science* 303:844-848 (2004) and Wang et al., "Cellular, Biochemical, and Genetic Analysis of Mechanism of Small Molecule IAP Inhibitors," *J. Biol. Chem.* 279:48168-48176 (2004)). In addition, high-throughput screens designed to detect small molecules that stabilize p27 identified compounds that either inhibited 26S proteasome activity, prevented Skp2 from incorporating into the SCF complex, or downregulated Skp2 mRNA (Chen et al., "Targeting the p27 E3 Ligase SCF(Skp2) Results in p27- and Skp2-mediated Cell-cycle Arrest and Activation of Autophagy," *Blood* 111: 4690-4699 (2008); Nickeleit et al., "Argyrin A Reveals a Critical Role for the Tumor Suppressor Protein p27(kip1) in Mediating Antitumor Activities in Response to Proteasome Inhibition," *Cancer Cell* 14:23-35 (2008); and Rico-Bautista et al., "Chemical Genetics Approach to Restoring p27Kip1 Reveals Novel Compounds with Antiproliferative Activity in Prostate Cancer Cells," *BMC Biol.* 8:153 (2010)). No inhibitors specifically and directly targeted to the E3 ligase activity of Skp2 have been identified, however.

The present invention is directed to overcoming these and other deficiencies in the art.

SUMMARY OF THE INVENTION

In one aspect, the present invention relates to a pharmaceutical composition comprising a compound of formula (I):

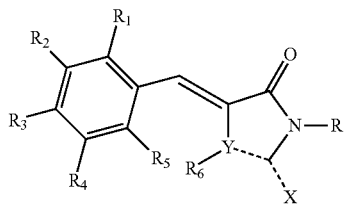

(I)

a stereoisomer, pharmaceutically acceptable salt, oxide, solvate, or ester thereof, where ------ is a single or double bond;

R is H, $C_{1-6}$ alkyl, $C_{2-6}$ alkenyl, $C_{2-6}$ alkynyl, $R_7$, $CH_2R_7$, $CH_2C(O)R_7$, or $CH_2C(O)NHR_7$;

$R_1$ is H, $OR_8$, or $OCH_2COOR_8$;

$R_2$ is H, $OR_8$, or $OCH_2COOR_8$;

$R_3$ is H, $C_{1-6}$ alkyl, $C_{2-6}$ alkenyl, $C_{2-6}$ alkynyl, $OCH_2COOR_8$, or $OS(O)_2R_7NHC(O)R_8$;

or $R_2$ and $R_3$ can combine to form —$OCH_2O$—;

$R_4$ is H or halogen;

$R_5$ is H or $OR_8$;

or $R_4$ and $R_5$ can combine to form a 6-membered aryl ring;

$R_6$ is optional, and if present is $COOR_8$ $R_7$ is a monocyclic or polycyclic aryl, or a monocyclic or polycyclic heterocyclyl or heteroaryl containing 1-5 heteroatoms selected from the group consisting of nitrogen, oxygen, and sulfur, each $R_7$ being optionally substituted from 1-3 times with substituents selected from the group consisting of halogen, $COOR_8$, $C_{1-6}$ alkyl, $C_{2-6}$ alkenyl, and $C_{2-6}$ alkynyl;

$R_8$ is H, $C_{1-6}$ alkyl, $C_{2-6}$ alkenyl, or $C_{2-6}$ alkynyl;

X is S, O, $C_{1-6}$ alkyl, $C_{2-6}$ alkenyl, or $C_{2-6}$ alkynyl;

Y is S or C; and a pharmaceutically acceptable carrier.

A second aspect of the present invention relates to a pharmaceutical composition comprising a compound of formula (II):

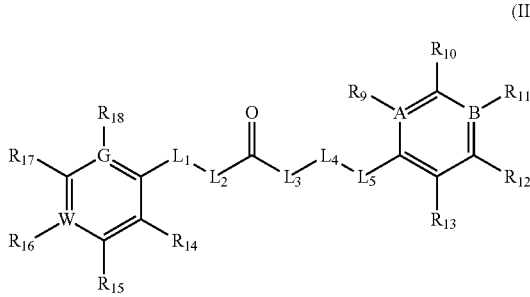

(II)

a stereoisomer, pharmaceutically acceptable salt, oxide, solvate, or ester thereof, where A is C or O;

B is C or absent;

G is C or S;

W is C or absent;

$L_1$ is independently selected from the group consisting of:

(1) absent;

(2) —C(S)NH—; or (3)

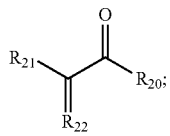

$L_2$ is NH or O;

$L_3$ is independently selected from the group consisting of:

(1) absent;

(2) —$CH_2$—;

$L_4$ is independently selected from the group consisting of:

(1) absent;

(2) —N($R_{19}$)—;

(3) —$R_{24}$=N—N=CH—;

$L_5$ is independently selected from the group consisting of:

(1) absent;

(2) —C(O)—;

$R_9$ is H;

$R_{10}$ is H, halogen, $C_{1-6}$ alkyl, $C_{2-6}$ alkenyl, or $C_{2-6}$ alkynyl;

$R_{11}$ is H, halogen, $NO_2$, $OCH_2COOR_{23}$, $OC(O)R_{23}$, or $OR_{23}$;

$R_{12}$ is H or $OR_{23}$;

$R_{13}$ is H;

or when $L_4$ is —N($R_{19}$)— and $L_5$ is —C(O)—, $R_{13}$ can combine with $R_{19}$ to form —C(O)—;

$R_{14}$ is H, $OR_{23}$, $C(O)NH_2$, or $COOR_{23}$;

$R_{15}$ is H, halogen, $C_{1-6}$ alkyl, $C_{2-6}$ alkenyl, $C_{2-6}$ alkynyl, or $COOR_{23}$;

$R_{16}$ is H, halogen, $C_{1-6}$ alkyl, $C_{2-6}$ alkenyl, $C_{2-6}$ alkynyl, —CH=$R_{24}$, or $COOR_{23}$;

$R_{17}$ is H, halogen, $C_{1-6}$ alkyl, $C_{2-6}$ alkenyl, $C_{2-6}$ alkynyl, or $COOR_{23}$;

$R_{18}$ is H, $C_{1-6}$ alkyl, $C_{2-6}$ alkenyl, $C_{2-6}$ alkynyl, $OR_{23}$, or $COOR_{23}$;

$R_{20}$ is —NH—, —NH—N=CH—, or $NH_2$;

$R_{21}$ is —$(CH_2)_n$—, where n is 0 to 6;

$R_{22}$ is —CH— or —$CHR_{24}$;

$R_{23}$ is H, $C_{1-6}$ alkyl, $C_{2-6}$ alkenyl, or $C_{2-6}$ alkynyl;

$R_{24}$ is a monocyclic or polycyclic aryl, or a monocyclic or polycyclic heterocyclyl or heteroaryl containing 1-5 heteroatoms selected from the group consisting of nitrogen, oxygen, and sulfur, each $R_{24}$ being optionally substituted from 1-3 times with substituents selected from the group consisting of OH, $C_{1-6}$ alkyl, $C_{2-6}$ alkenyl, $C_{2-6}$ alkynyl, =O, =NH, $NH_2$, halogen, $COOR_{23}$ and a pharmaceutically acceptable carrier.

A third aspect of the present invention is directed to a pharmaceutical composition comprising a compound of formula (III):

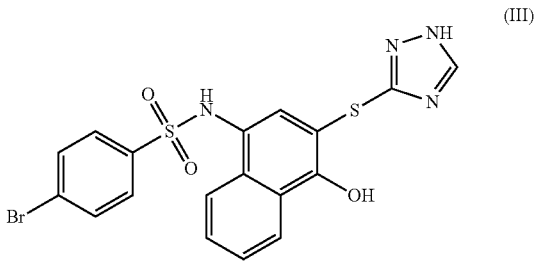

(III)

a stereoisomer, pharmaceutically acceptable salt, oxide, solvate, or ester thereof and a pharmaceutically acceptable carrier.

A fourth aspect of the present invention relates to a pharmaceutical composition comprising a compound of formula (IV):

IV a stereoisomer, pharmaceutically acceptable salt, oxide, solvate, or ester thereof and a pharmaceutically acceptable carrier.

A fifth aspect of the present invention is directed to a pharmaceutical composition comprising a compound of formula (V):

(V)

a stereoisomer, pharmaceutically acceptable salt, oxide, solvate, or ester thereof and a pharmaceutically acceptable carrier.

A sixth aspect of the present invention is directed to a method of treating cancer in a subject. This method involves selecting a subject with cancer and administering to the subject a compound of formulae (I)-(V) as defined herein under conditions effective to treat cancer in the subject.

A seventh aspect of the present invention relates to a method of inhibiting SCF-Skp2 activity. This method involves administering to cells a compound of formulae (I)-(V) as defined herein under conditions effective to inhibit SCF-Skp2 activity in the cell.

An eighth aspect of the present invention relates to a method of identifying inhibitors of SCF-Skp2 activity. This method involves providing a model comprising a p27-binding interface of a Skp2-Cks 1 complex; providing one or more candidate compounds; evaluating contact between the candidate compounds and the model to determine which of the one or more candidate compounds have an ability to bind to and/or fit in the p27-binding interface of a Skp2-Cks 1 complex; and identifying compounds which, based on said evaluating, have the ability to bind to and/or fit in the p27-binding interface of a Skp2-Cks 1 complex as compounds potentially useful as inhibitors of SCF-Skp2 activity.

A ninth aspect of the present invention relates to a method of inhibiting SCF-Skp2 activity in a subject. This method involves selecting a subject in need of inhibiting Skp2-mediated p27 degradation; providing a compound which binds to and/or fits in a p27-binding interface of a Skp2-Cks 1 complex; and administering the compound to the selected subject under conditions effective to inhibit SCF-Skp2-mediated p27 degradation activity in the subject.

Inhibitors have been identified using structure-based drug discovery to target specific three-dimensional ("3D") molecular surfaces, or pockets, at the substrate's binding site (Cardozo et al., "Druggability of SCF ubiquitin ligase-protein interfaces," *Methods Enzymol.* 399:634-653 (2005) and Cardozo et al., "Wrenches in the works: drug discovery targeting the SCF ubiquitin ligase and APC/C complexes," *BMC Biochem.* 8 Suppl 1:S9 (2007)). The first selective inhibitors against PERK catalytic activity were identified using a pocket-targeted approach (Wang et al., "Structural determinants of PERK inhibitor potency and selectivity," *Chem. Biol. Drug Des.* 76:480-495 (2010)). The present invention targets a protein-protein interface with an in silico structure-based discovery tool, virtual ligand screening (VLS) against a pocket identified at the p27-binding interface formed by Skp2-Cks1. The combination of VLS, chemical similarity searches, in vitro functional screens, and couterscreens identified four selective inhibitors of Skp2 ligase activity. The inhibitors increased both p27 protein level and half-life in metastatic melanoma cell lines, with this activity dependent on Skp2 Inhibitor treatments in various cancer cells also shifted the population of cells into G1 or G2/M phase, and this phenotype was both p27 and cell type dependent.

Clinical efficacy of the proteasome inhibitor Bortezomib (Velcade™) established the ubiquitin proteasome system ("UPS") as a key target in cancer. In a number of human cancers, low levels of the cell-cycle regulatory tumor suppressor p27 correlate with the overexpression of its UPS E3 ligase SCF-Skp2, suggesting that deregulation of p27 degradation by the UPS promotes carcinogenesis. Thus, inhibitors designed to stabilize p27 by selectively targeting SCF-Skp2 may provide a new avenue of cancer treatment with enhanced specificity over Bortezomib.

From a chemistry point of view, however, identifying a specific small molecule inhibitor of the SCF-Skp2/p27 interface is challenging, since this is a protein-protein interface. Using a structure-based approach encompassing both in silico virtual ligand screening (VLS) and in vitro assays, a diverse set of inhibitors of Skp2-mediated p27 degradation were identified that reduce p27 ubiquitylation by specifically and competitively inhibiting the Skp2-p27 interaction. In various cancer cells, these compounds induce p27 and elicit cell cycle arrest. This work establishes a proof-of-principle both for drug discovery targeting Skp2, a potential advance in biology, and for drug discovery targeting this form of protein-protein interface, a potential advance in chemistry.

In the ubiquitin proteasome system, the E3 ligase SCF-Skp2 and its accessory protein Cks1 promote proliferation largely by inducing the degradation of the CDK inhibitor p27. Overexpression of Skp2 in human cancers correlates with poor prognosis, and deregulation of SCF-Skp2-Cks1 promotes tumorigenesis in animal models. Pursuant to the present invention, small molecule inhibitors specific to SCF-Skp2 activity were identified using in silico screens targeted to the binding interface for p27. These compounds selectively inhibited Skp2-mediated p27 degradation by reducing p27 binding through key compound-receptor contacts. In cancer cells, the compounds induced p27 accumulation in a Skp2-dependent manner and promoted cell-type specific blocks in the G1 or G2/M phases. Designing SCF-Skp2 specific inhibitors is a novel strategy to treat cancers dependent on the Skp2-p27 axis.

BRIEF DESCRIPTION OF THE DRAWINGS

FIGS. 1A-E relate to in silico and in vitro screens for Skp2 ligase inhibitors. In FIG. 1A, the top picture shows an ICM 3D receptor model of Skp2 (medium grey ribbon), Cks1 (dark grey ribbon), and p27 phospho-peptide (light grey ribbon, phospho-T187 and E185 in wire). Key residues important for E185 interactions are highlighted in ball and stick, colored accordingly. The bottom picture of FIG. 1A shows a grey globular pocket exposed with removal of p27 peptide and antagonizes p27-E185 interactions. FIG. 1B is a photograph of results of calibration of the in vitro ubiquitylation assay. Immunoblotting was for p27 (poly-ubiquitylation ladder, p27-(Ub)$_n$), Cks1, Cyclin E, Cul1, Skp2, and Skp1 levels in the absence of Vehicle, Cks1, or CyclinE/CDK2; or in the presence of Vehicle (0.1% DMSO), 1 µM NEDD8-activating enzyme (NAE) inhibitor MLN-4924, or 50 µM CDK2 inhibitor Roscovitine. FIG. 1C is a photograph of results of the representative primary screen for activity. Immunoblotting was for p27-(UB)$_n$, Cul1, Skp2, and Skp1 in ubiquitylation assays treated with Vehicle (0.1% DMSO) or 50 µM inhibitor (C1, C2, C20, or C16). FIG. 1D is a photograph of results showing E2 charging is unaffected by active compound. Immunoblotting was for His-tagged Ubc3-ubiquitin conjugates (Ubc3~Ub) in the presence of Vehicle (0.1% DMSO, Veh) or 50 µM inhibitor (C1, C2, C20, or C16) under non-reducing or reducing (Beta-mercaptoethanol, BME) conditions. FIG. 1E is a photograph of results showing compound treatment blocks the physical p27-Skp2 interaction. Immunoblotting was for p27, Skp2, and Skp1 from HA-immunoprecipitates of ubiquitylation assays treated with Vehicle (0.1% DMSO, Veh) or 50 µM C1. No background using rabbit reticulocyte lysate (RRL) only.

FIGS. 2A-E relate to the structure-function approach to identifying key contacts. FIG. 2A shows the chemical structures of C1 and C2. The box is an active group used in chemical similarity search. FIG. 2B shows predicted conformations with lowest energy for C1 and C2 (ball and stick) interacting with residues (wire) in Skp2 (medium grey ribbon) and Cks1 (dark grey ribbon). Hydrogen bonds are depicted as small balls. FIG. 2C shows the chemical structures of C16 and C20 containing active groups (box) from FIG. 2A. FIG. 2D is a photograph of results showing that removal of active groups reverses activity. Immunoblotting was for p27, Skp2, and Skp1 from ubiquitylation assays treated with Vehicle (0.1% DMSO), 50 µM inhibitors (C2, C20, C1, or C16), or 50 µM unmatched compound (UM, see FIG. 8A) lacking active groups. FIG. 2E is a photograph of results showing that Cks1 mutation reverses inhibitor activity, as predicted by a binding model (see also FIG. 7B). Immunoblotting was for p27, Cks1, Skp2, and Skp1 from ubiquitylation assays using Wild Type-Cks1 (left side of the picture) or Q52L-Cks1 (right side of the picture) treated with Vehicle (0.1% DMSO) or 50 µM inhibitor (C1 or C16).

FIGS. 3A-D are results showing that binding of inhibitors disrupts the Skp2-p27 interaction. FIG. 3A is a photograph of results showing that reduced ubiquitylation correlates with reduced interaction. The left side of the picture of FIG. 3A shows immunoblotting for p27, Skp2, and Skp1 from in vitro ubiquitylation assays treated with Vehicle (0.1% DMSO) or 10 µM inhibitor (C20, C2, C1, or C16). The right side of the picture of FIG. 3A shows immunoblotting for p27, Skp1, Cul1, and HA-Skp2 in HA immunoprecipitates from ubiquitylation reactions. FIG. 3B is a photograph of results showing that inhibitors reduce p27 binding to Skp2. HA-Skp2 and Cks1 proteins were pretreated with Vehicle (0.1% DMSO) or 10 µM inhibitor (C20, C2, C1, or C16) before being added to p27-pT187. HA-immunoprecipitates were immunoblotted for p27, Cks1, and Skp2. FIG. 3C is a photograph of results showing that loss of chemically active groups restores binding. HA-Skp2/Cks1 was pretreated with 10 µM inhibitor (C1 or C2) or corresponding unmatched compound (UM-C1 or UM-C2b, see FIG. 8A) before p27-pT187 addition. HA-immunoprecipitates were immunoblotted for p27, Skp1, and Skp2. FIG. 3D shows that the loss of active group removes compound binding. Melting temperature (Tm) of recombinant His-6Skp1-Skp2-Cks1 (1.5 µM) preincubated with C1 (75 µM), UM-C1 (75 µM), or Vehicle (0.5% DMSO) determined from melting peaks using differential scanning fluorimetry.

FIG. 4A is a photograph of results showing protein induction following inhibitor treatment. Immunoblotting was for steady state levels of Skp2 substrates (p27, p21, p130, and Cdt1), Skp2, Skp1, Cul1, and Nedd8 in 501 Mel cells (left side of FIG. 4A) treated with vehicle (0.1% DMSO, Veh) or 10 µM inhibitor (C20, C2, C1, or C16) and (right side of FIG. 4A) untreated (Unt) or treated with 10 µM proteasome inhibitor MG-132 (MG) or 400 nM NAE inhibitor MLN-4924 (MLN). Loading was normalized to alpha-tubulin. FIG. 4B is a photograph of results showing immunoblotting for p27, Skp1, and Skp2 steady state levels in melanoma cell lines, SK-MEL-147 (top picture) and SK-MEL-173 (bottom picture) treated with vehicle (0.1% DMSO) or 10 µM inhibitor (C20, C2, C1, or C16). Loading was normalized to alpha-tubulin. FIG. 4C is a photograph of results showing p27 half-life analysis. Cycloheximide half-life from 501 Mel cells pretreated 16 hours with Vehicle (0.1% DMSO) or 10 µM inhibitor (C16, C1, C20, or C2). Representative immunoblots at times 0, 1, 3, and 5 hours post-cycloheximide (n=3). Total protein was normalized to alpha-tubulin. The graph shows densitometry levels for percent p27 protein remaining FIG. 4D is a photograph of results showing p27 induction by compounds is dependent on Skp2. Immunoblotting was for p27 and Skp2 in 501 Mel cells expressing shRNA against Skp2 (shSkp2) or empty vector (shEmpty) treated with Vehicle (0.1% DMSO, Veh) or 10 µM inhibitor (C1 or C2, on the left side of FIG. 4D; C16 or C20, on the right side of FIG. 4D). Loading was normalized to alpha-tubulin.

FIGS. 5A-E relate to Skp2 ligase inhibitors inducing cell cycle changes. FIG. 5A is a photograph of results showing a p27-dependent G1 arrest. The left photograph of FIG. 5A shows results of 501 Mel cells expressing empty vector (shEmpty) or two different shRNAs (shp27-1 or shp27-5) against p27 being immunoblotted for protein expression of p27, Skp2, Skp1, and alpha-tubulin. The center graph of FIG. 5A shows results for the previously mentioned cell lines stained with Propidium Iodide for FACS analysis. The graph represents mean+/−STDEV from n=3. *, p<0.01; , p<0.001 compared with shEmpty (one-way ANOVA followed by Dunnett test). The right graph of FIG. 5A shows results after shp27-1 501 Mel cells treated with Vehicle (0.1% DMSO, Veh) or 10 µM inhibitor (C1, C16, C2, or C20) were stained with Propidium Iodide for FACS analysis. The graph represents mean+/−STDEV from n=4. FIG. 5B relates to G1 induction by inhibitors. The photograph on the left side of FIG. 5B shows results after shEmpty 501 Mel cells were treated with Vehicle (0.1% DMSO, Veh) or 10 µM inhibitor (C1, C16, C2, or C20) and were immunoblotted for p27, Skp2, Skp1, and alpha-tubulin. The graph on the right side of FIG. 5B** represents FACS analysis of the previously mentioned treated cell lines with the mean+/−STDEV from n=4. *, p<0.05; , p<0.01; *, p<0.001 compared with shEmpty Vehicle (one-way ANOVA followed by Dunnett test). FIG. 5C shows results of G1 or G2/M induction by C1 in breast cancer cells. The left graph shows results of FACS analysis of T47D and MCF-7 treated with Vehicle (0.1% DMSO, Veh) or 5 µM C1. The graph represents mean+/−STDEV from n=4 for T47D and n=3 for MCF-7. *, p<0.0001 compared with corresponding cell cycle phase in Vehicle (unpaired two-tailed Student's t test). The graph on the right of FIG. 5C shows results of FACS analysis of MCF-7 treated with increasing doses of C1. The graph represents mean+/−STDEV from n=3. *, p<0.01; , p<0.001 compared with Vehicle (one-way ANOVA followed by Dunnett test). FIG. 5D** is a graph showing results of G1 induction by C2 in prostate cancer cells using FACS analysis of LNCaP cells treated with Vehicle (0.1% DMSO, Veh) or 10 µM C2. The graph represents mean+/−STDEV from n=6. *, p<0.0001 compared with Vehicle (unpaired two-tailed Student's t test). FIG. 5E is a photograph of results showing p27 protein induction in cancer cells. Immunoblotting for p27, Skp2, Skp1, and alpha-tubulin in MCF-7, T47D, or LNCaP cells treated with Vehicle (0.1% DMSO, Veh), 5 µM C1, or 10 µM C2.

FIG. 6A is a photograph of results showing that MDM2 activity is not blocked by Skp2 ligase inhibitors. Immunoblotting was for p53 (poly-ubiquitylation ladder, p53-(Ub)$_n$), MDM2, and His-Ubc5 from in vitro ubiquitylation assays treated with Vehicle (0.1% DMSO) or 50 µM inhibitor (C1, C2, C16, or C20). Negative controls include exclusion of MDM2 or addition of 10 mM EDTA. FIG. 6B is a photograph of results showing that β-TrCP activity is not blocked by Skp2 ligase inhibitors. Immunoblotting was for HA (poly-ubiquitylation ladder, PDCD4-(Ub)$_n$), □ β-TrCP, and Skp1 from in vitro ubiquitylation assays treated with +/−Vehicle (0.1% DMSO) or 50 µM inhibitor (C1, C2, C16, or C20). Negative control is exclusion of S6 Kinase 1 (S6K1). FIG. 6C is a photograph of results showing that CyclinE/CDK2 activity is not blocked by Skp2 ligase inhibitors. Immunoblotting was for phospho-T187 p27, total p27, and cyclin E from kinase assays treated with Vehicle (0.1% DMSO) or 50 µM inhibitor (C1, C2, C16, or C20). Negative control is exclusion of CyclinE/CDK2. FIG. 6D is a photograph of results showing dose response to inhibitor C2. Immunoblotting was for p27 (poly-ubiquitylation ladder, p27-(Ub)$_n$) from Skp2-mediated in vitro ubiquitylation assays treated with Vehicle (0.1% DMSO) or increasing concentrations of C2 (2.5 µM-100 µM).

In FIG. 7A, docking pose is predicted for C1 (left) and C2 (center) displayed as ball and stick in the Skp2 (medium grey ribbon)-Cks1 (dark grey ribbon) interface. Electrostatic surface of the binding pockets is displayed in grey tones. p27 binding (light grey ribbon) is antagonized by the compounds. The right side of FIG. 7A shows overlay of C1 (light grey ball and stick) and C16 (dark grey ball and stick) lowest energy poses highlighting the —COOH group (oval circle) that is required for interacting with —NH2 side group of Q52 Cks1 (matchstick). In FIG. 7B, the left shows in silico model of C1 at the Cks1 interface. C1 is displayed as ball and stick (ball color based on charge, dark grey=negative) with a medium grey carbon backbone. Csk1 residue Q52 is displayed as ball and stick (ball color based on charge, dark grey=positive) with a light grey carbon backbone. The —NH$_2$ group in Q52 is positioned 2.0 Angstrom away from the COOH group in C1, allowing an electrostatic interaction to form. On the right, in silico model of Q52L-Cks1 mutation removes the electrostatic interaction. FIG. 7C shows that residues important for inhibitor binding are also required for p27 ubiquitylation. In FIG. 7C, the left picture shows an immunoblot for p27 (poly-ubiquitylation, p27-(Ub)$_n$), Cks1, Skp2, and Skp1 in in vitro ubiquitylation assays using either WildType-Skp2, R294A, or R344A mutants. The right picture shows immunoblot for p27 (poly-ubiquitylation, p27-(Ub)$_n$), Skp2, and Cks1 from in vitro ubiquitylation assays using either WildType-Cks1 or R44A/H mutants.

In FIG. 8A, the top line of chemicals shows structures of compounds (C1, C2, C16, C20) with queries (predicted active group) used in similarity searches highlighted in the box. The bottom line of chemicals shows structures of unmatched compounds (UM-C1, UM-C2a, UM-C2b, UM-C16, UM-C20) lacking the highlighted group. Hierarchy chemical similarity tree is based on Tanimoto distance (top axis, 0-0.6) between all compounds. Diverse compounds have a distance greater than 0.3 (Grigoryan et al., "Spatial Chemical Distance Based on Atomic Property Fields," *Journal of Computer-aided Molecular Design* 24:173-182 (2010), which are hereby incorporated by reference in their entirety). Distance between compounds and corresponding unmatch: Group 1=0.27, Group 2=0.19, Group 3=0.31. Distance between each compound-unmatch set: Group 4=0.57 and Group 5=0.66. FIG. 8B shows rhodanine core and rhodanine containing compounds that tested negative in the in vitro ubiquitylation functional assay. Neg-C1b is a second unmatch compound to C1. Neg-5 is a compound identified to be a promiscuous PAINS (Baell et al., "New Substructure Filters for Removal of Pan Assay Interference Compounds (PAINS) from Screening Libraries and for Their Exclusion In Bioassays," *J. Med. Chem.* 53:2719-2740 (2010), which is hereby incorporated by reference in its entirety) but has no ability to block Skp2-mediated ubiquitylation. FIG. 8C shows binding of C20 to Skp2-Skp1-Cks1. Overlay of the representative SPR sensorgram displaying the association and dissociation curves of decreasing C20 concentrations with the His6-Skp2-Skp1-Cks1 recombinant protein complex. The corresponding fitted curves are shown as smooth lines. C20 $K_D$ is calculated to be 47±14 µM.

FIG. 9A shows an immunoblot for p27 induction in 501 Mel metastatic melanoma cell lines or MCF-7 breast cancer cell lines treated 16 h with increasing concentration of C1, C2, C16, and C20. Immunoblot for Skp2 confirms inhibitors are not affecting levels of the ligase. Loading is normalized to alpha-tubulin. FIG. 9B shows the percentage of viable cells in 501 Mel metastatic melanoma cell lines (left) and proliferating MCF-7 breast cancer cell lines (right) treated 16 h with increasing concentration of C1, C2, C16, and/or C20. Each treatment was performed in quadruplicates and repeated three times.

FIGS. 10A-C relate to cytotoxicity curves and protein induction in multiple myeloma, mantle cell lymphoma, and endometrial carcinoma cell lines. FIG. 10A shows the percentage of viable cells in two different multiple myeloma cell lines (KSM-11 and ARP-1) using increasing concentration of C1 treatment for 24 hours. The IC50 is calculated at 1.84 μM or 3.84 μM, respectively. FIG. 10B shows the percentage of cell viability in JeKo-1 mantle cell lymphoma cell line after treatment with increasing concentration of C1 and C20 for three time points (24, 48, and 72 hours). The graph represents mean+/−STDEV from n=3. IC50 for each time point is calculated using CalcuSyn software and is listed in the chart. FIG. 10C is a photograph of results showing p27 protein induction in ECC-1 endometrial cancer cell line treated with increasing concentration of C2 treatment after 24 hours. Immunoblotting was for p27, Skp2, and Beta-actin. Vehicle (Veh) contains 0.1% DMSO. 1 μM of lactacystin (Lact) inhibits the proteasome and is the positive control for p27 induction.

FIG. 11A shows that the Skp2E3LIs, C2, C20, and N1, and C16, but not L6 increase p27 protein levels in ECC-1 cells over Vehicle (Veh) control. Cells were prepared, treated with Skp2E3LIs, and whole cell lysates immunoblotted, all as described in Example 8; n=3 experiments. FIG. 11B shows a dose-dependent response to C2 and C20, with no effect on the levels of Skp2. Cells were treated and analyzed as described in FIG. 11A (n=4). FIG. 11C shows that C2 and C20 specifically increase nuclear p27, while N1 and C16 increase cytoplasmic and nuclear p27 over control. Antibodies to α-tubulin and Sp1 confirm purity of cytoplasmic and nuclear fractions, respectively. The graph reflects densitometric analysis of protein bands indicating relative intensity of p27 levels normalized to actin (Veh=100%; n=2). FIG. 11D shows that Lactacystin increases both nuclear and cytoplasmic p27. The graph shows the relative intensity of p27 levels normalized to actin (Veh=100%; n=3).

In FIG. 12A, the endometrial carcinoma cell line HEC-1B (moderately differentiated; from ATCC) in Minimum Essential Medium (Invitrogen) supplemented with 1 mM sodium pyruvate and 2 mM L-Glutamine and 10% FBS were seeded at $3 \times 10^5$ cells/well/6-well plate and cultured until 70% confluency. The cells were synchronized in serum-free media for 24 h and treated with 0-100 nM 17β-Estradiol (E2) for 18 h. Cell lysates were prepared in cold RIPA buffer (50 mM Tris-HCl, 150 mM NaCl, 1 mM NaF, 1 mM $Na_3VO_4$, 0.25% sodium deoxycholate, 1% NP40 and 1 mM EDTA, pH 7.4) supplemented with 1 mM PMSF and protease inhibitor cocktail (Sigma). Protein concentrations were determined by MicroBCA Protein Assay kit (ThermoScientific) and equal protein concentrations (20 μg/well) were applied to an SDS-PAGE (12% acrylamide) and then transferred to nitrocellulose membranes. The membranes were blocked with 3% BSA in TBS containing 0.1% Tween (TBST) for 1 h and incubated with rabbit anti-phospho-p27 (1:1000, PT187, Invitrogen) in TBST overnight at 4° C. followed by peroxidase conjugated goat anti-rabbit secondary antibody (1:2000) in TBST for 1 h. The blots were incubated with SuperSignal West Dura Extended Duration Substrate kit (ThermoScientific) and protein bands visualized by exposure on x-ray film (Denville Scientific). The blots were stripped and re-probed with anti-β-actin (1:10,000, AC-15, Sigma). Densitometry was performed and the intensity of each band determined by ID Image analysis (Kodak); each protein band was normalized to the density of actin in each well and expressed as fold-increase or percent decrease compared to the untreated control. The blot shows that E2 dose-dependently increases the phosphorylation of p27 at T187 (p-p27[T187]) with a peak response of 1.75 fold at 0.1 nM E2 compared to the untreated control that decreases by 40% at 10 nM. The HEC-1B cell line was more sensitive to E2 than the ECC-1 cell line. (n=2 for HEC-1B cells). In FIG. 12B, estrogen (E2)-induced decrease in p27 is mediated by MARK/MEK. The endometrial carcinoma cell line, ECC-1 cells, were seeded, synchronized and treated as described for FIG. 12A, in the presence or absence of the MAPK/MEK inhibitor, PD98059 (PD), (Calbiochem) at a final concentration of 20 μM, for 18 h. Cell lysates were prepared and equal protein concentrations (20 μg) subjected to SDS-PAGE followed by protein transfer to nitrocellulose membranes, as described in FIG. 12A. The membranes were blocked with 5% non-fat dry milk in TBST for 1 h followed by incubation overnight with mouse anti-human $p27^{kip1}$ (1:1000, Clone 57, BD Transduction Labs) in TBST followed by peroxidase-conjugated goat anti-mouse secondary antibody (1:2000, ThermoScientific). The intensity of p27 protein band was determined as described in FIG. 12A. The immunoblot shows that E2 decreases p27 in total cell lysates by 46% of the untreated control, which is partially blocked by the MAPK/MEK inhibitor PD 98059 (24% less than control). (n=3 separate experiments).

In FIG. 13A, Skp2E3LIs C2 and C20 are shown to inhibit cell proliferation. Cells were prepared and analyzed for proliferation by the MTS assay; values were calculated as percent of Vehicle-treated control ±SD, and statistical significance determined using GraphPad Prism Software; *P≤0.05 (n=4). FIG. 13B is a graph showing that the half-maximal effective concentration (EC50) of C2 in inhibiting proliferation of ECC-1 is 14.3 μM. ECC-1 cells were treated as described in Example 8 to obtain values as percent of Vehicle-treated control and EC50 calculated using the Hillslope method (n=2). FIG. 13C is a graph showing that C2, C20, and N1 are not cytotoxic for ECC-1 cells. Cell viability was calculated as percent of control, all as described in Example 8. Significance: *P≤0.05. (n=2). FIG. 13D shows that C2 and C20 do not induce apoptosis. Apoptosis was determined in whole cell lysates by Caspase-3 cleavage, as described in Example 8. (n=2).

FIG. 14A shows that knocking-down Skp2 with Skp2 siRNA blocks the ability of C2 and C20 to increase nuclear p27. ECC-1 cells were transfected with either control siRNA or 10 nM Skp2 siRNA, treated with C2 and C20 and lysates analyzed, all as described in Example 8. (n=2). FIG. 14B is a graph showing that knocking-down Skp2 blocks the ability of C2 and C20 to inhibit cell proliferation. Skp2 siRNA transfected cells were treated and analyzed described in Example 8. (n=2). FIG. 14C shows that C2 and C20 block E2-induced degradation of nuclear and cytoplasmic p27. Cells were prepared and treated as shown in FIG. 14C and analyzed, all as described in Example 8. (n=3). FIG. 14D shows that Skp2E3LIs C2 and C20 block E2-induced proliferation in ECC-1 cells. Cells were treated with C2 and C20, and cell proliferation determined, all as described in Example 8. Percent of control values are below the bars. (n=3). FIG. 14E shows that treatment with C2 and C20 together did not further increase nuclear p27 levels than either alone. (n=3).

C2 and C20 increase p27 half-life over controls in ECC-1 cells. In FIGS. 15A-B, C2 stabilizes nuclear p27 and simultaneously decreases cytoplasmic p27; Lactacystin stabilizes p27 in both subcellular fractions. Cells were prepared, treated, and subfractionated at the times shown, all as described in Example 8. Densitometric values appear below each lane as percent of control. (n=2). FIG. 15C shows that C2 and C20 extend p27 half-life (prevent degradation) by 6.1 h and 2.7 h over cycloheximide (CHX) control. Cells were prepared, treated with C2, C20, or Vehicle, chased with 20 µM cycloheximide (CHX), and cell lysates were collected at time points, all as described in Example 8. The graph depicts the relative intensity of p27 levels. (n=2).

In FIG. 17A, p27 protein is increased in total cell lysates of primary ECA cells derived from grade I endometrioid ECA. Primary ECA cells were prepared from Type I endometrioid tumors, treated, and cell lysates analyzed, all as described in Example 8. Densitometry values are shown at the base of the blot as percent of control. FIG. 17B shows that the Skp2E3LIs C2 and C20 increase nuclear p27 while decreasing cytoplasmic p27 in primary ECA cells derived from a grade II endometrioid ECA showing p27 mislocalized to the cytoplasm prior to treatment. Cells were treated and nuclear cytoplasmic fractions analyzed, all as described in Example 8. The graph represents relative intensity of p27 levels.

FIG. 19 is a table showing a list of primers used for real-time RT-PCR: p27 F (SEQ ID NO:1), p27 R (SEQ ID NO:2), Skp2 F (SEQ ID NO:3), Skp2 R (SEQ ID NO:4), Cks1 F (SEQ ID NO:5), Cks1 R (SEQ ID NO:6), Cdh1 F (SEQ ID NO:7), Cdh1 R (SEQ ID NO:8), PR F (SEQ ID NO:9), PR R (SEQ ID NO:10), glycodelin F (SEQ ID NO:11), glycodelin R (SEQ ID NO:12), actin F (SEQ ID NO: 13), and actin R (SEQ ID NO:14).

DETAILED DESCRIPTION OF THE INVENTION

Figure 1A:
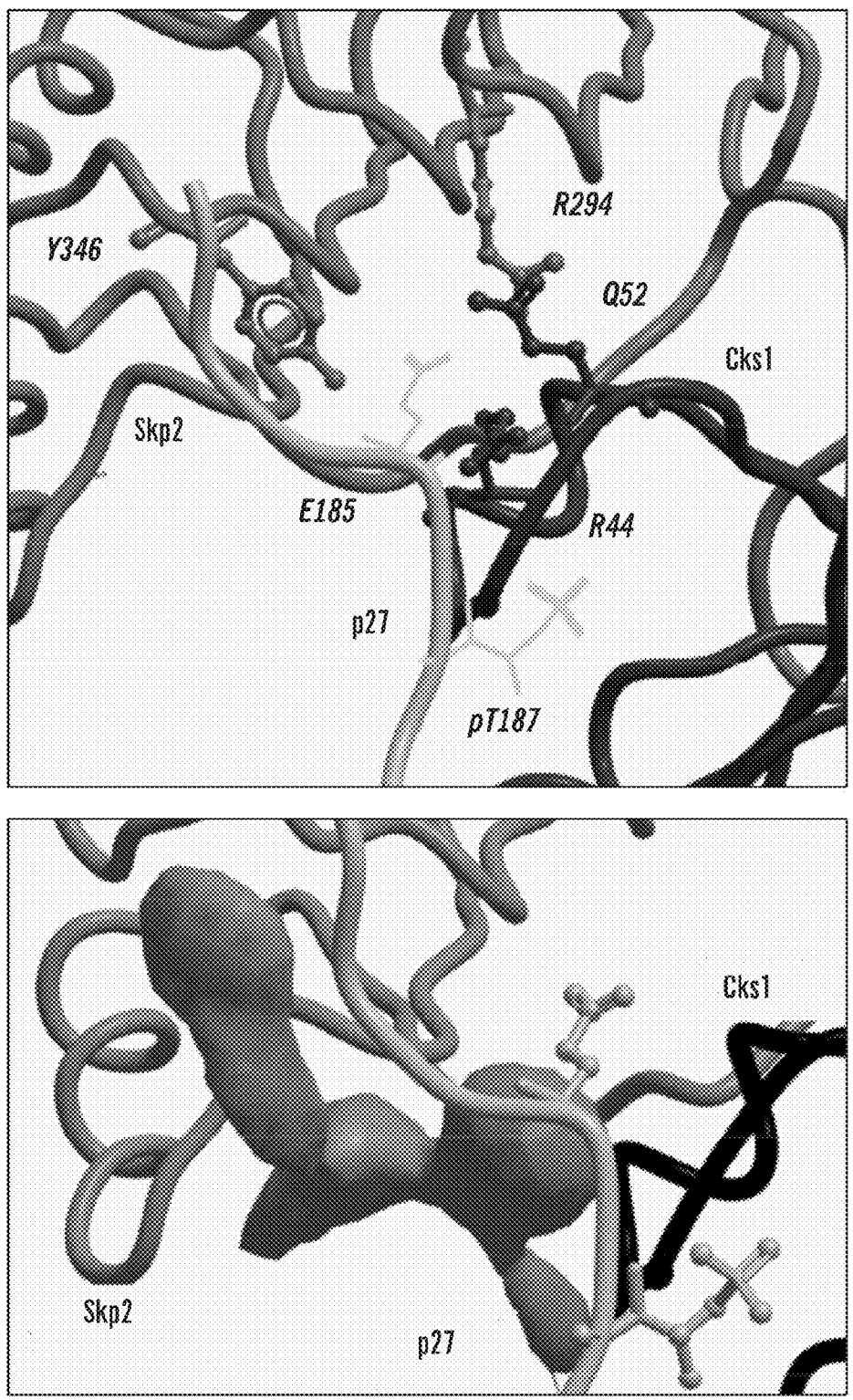

The present invention relates to a pharmaceutical composition comprising a compound of formula (I):

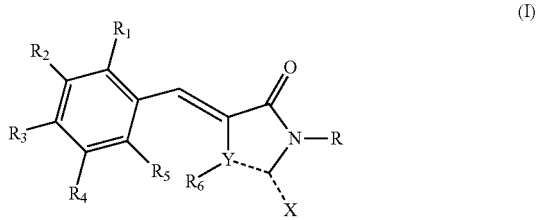

a stereoisomer, pharmaceutically acceptable salt, oxide, solvate, or ester thereof, where
- ------ is a single or double bond;
- R is H, $C_{1-6}$ alkyl, $C_{2-6}$ alkenyl, $C_{2-6}$ alkynyl, $R_7$, $CH_2R_7$, $CH_2C(O)R_7$, or $CH_2C(O)NHR_7$;
- $R_1$ is H, $OR_8$, or $OCH_2COOR_8$;
- $R_2$ is H, $OR_8$, or $OCH_2COOR_8$;
- $R_3$ is H, $C_{1-6}$ alkyl, $C_{2-6}$ alkenyl, $C_{2-6}$ alkynyl, $OCH_2COOR_8$, or $OS(O)_2R_7NHC(O)R_8$;
- or $R_2$ and $R_3$ can combine to form —$OCH_2O$—;
- $R_4$ is H or halogen;
- $R_5$ is H or $OR_8$;
- or $R_4$ and $R_5$ can combine to form a 6-membered aryl ring;
- $R_6$ is optional, and if present is $COOR_8$
- $R_7$ is a monocyclic or polycyclic aryl, or a monocyclic or polycyclic heterocyclyl or heteroaryl containing 1-5 heteroatoms selected from the group consisting of nitrogen, oxygen, and sulfur, each $R_7$ being optionally substituted from 1-3 times with substituents selected from the group consisting of halogen, $COOR_8$, $C_{1-6}$ alkyl, $C_{2-6}$ alkenyl, and $C_{2-6}$ alkynyl;
- $R_8$ is H, $C_{1-6}$ alkyl, $C_{2-6}$ alkenyl, or $C_{2-6}$ alkynyl;
- X is S, O, $C_{1-6}$ alkyl, $C_{2-6}$ alkenyl, or $C_{2-6}$ alkynyl;
- Y is S or C; and
- a pharmaceutically acceptable carrier.

As used herein, the term "halo" or "halogen" means fluoro, chloro, bromo, or iodo.

The phrase "optionally substituted" indicates that a group may have a substituent at each substitutable atom of the group (including more than one substituent on a single atom), and the identity of each substituent is independent of the others.

The term "substituted" or "substitution" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds. By "stable compound" it is meant a compound that is sufficiently robust to survive isolation to a useful degree of purity from a reaction mixture, and formulation into an efficacious therapeutic agent. Exemplary substituents include, without limitation, oxo, thio (i.e., =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic hetereoaryl, polycyclic aryl, and polycyclic heteroaryl.

The term "monocyclic" indicates a molecular structure having one ring.

The term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain (or the number of carbons designated by "$C_{n\text{-}n}$", where n-n is the numerical range of carbon atoms). Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "aryl" or "aryl ring" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "heterocyclyl" refers to a stable 3- to 18-membered ring radical which consists of carbon atoms and from one to five heteroatoms selected from the group consisting of nitrogen, oxygen, and sulfur. The heterocyclyl radical may be a monocyclic, or a polycyclic ring system, which may include fused, bridged, or spiro ring systems; and the nitrogen, carbon, or sulfur atoms in the heterocyclyl radical may be optionally oxidized, the nitrogen atom may be optionally quaternized, and the ring radical may be partially or fully saturated. Examples of such heterocyclyl radicals include, without limitation, azepinyl, azocanyl, pyranyl, dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" means an aromatic monocyclic or multi-cyclic ring system of about 5 to about 14 ring atoms, or about 5 to about 10 ring atoms, in which one or more of the atoms in the ring system is/are element(s) other than carbon, for example, nitrogen, oxygen, or sulfur. In the case of multicyclic ring systems, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-c]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

Suitable aryl groups for the substituents of the present invention, include, but are not limited to phenyl, naphthyl, azulenyl, fluorenyl, phenanthrenyl, anthracenyl, pyrenyl, triphenylenyl, chrysenyl, and naphthacenyl. Suitable heteroaryl groups of the present invention include, but are not limited to pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuryl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, and naphthyridinyl. Exemplary substituted heteroaryls include without limitation pyridyl, 2-oxo-pyridin-1-yl, pyrimidinyl, pyridazinyl, pyrazinyl, 1,2,4-triazinyl, 1,3,5-triazinyl, furanyl, pyrrolyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, tetrazolyl, indolyl, isoindolyl, benzofuranyl, benzothiophenyl, indolinyl, oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, furo[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 2-oxo-2,3-dihydro-1H-benzo[d]imidazole, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridinyl.

Further heterocycles and heteroaryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

The term "alkoxy" means groups of from 1 to 6 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. Alkoxy also includes methylenedioxy and ethylenedioxy in which each oxygen atom is bonded to the atom, chain, or ring from which the methylenedioxy or ethylenedioxy group is pendant so as to form a ring.

The term "carboxy," employed alone or in combination with other terms, refers to a group of the formula —C(=O)OH.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

The term "cycloalkylalkyl" refers to a radical of the formula —$R^aR^b$ where $R^a$ is an alkyl radical as defined above and $R^b$ is a cycloalkyl radical as defined above. The alkyl radical and the cycloalkyl radical may be optionally substituted as defined above.

The term "cycloalkylene" means a group obtained by removal of a hydrogen atom from a cycloalkyl group. Non-limiting examples of cycloalkylene include cyclobutylene and cyclopropylene.

The term "arylene" means a group obtained by removal of a hydrogen atom from an aryl group. Non-limiting examples of arylene include phenylene and naphthylene.

The term "heterocyclylene" means a group obtained by removal of a hydrogen atom from a heterocyclyl group. Non-limiting examples of heterocyclylene include piperidylene, pyrrolidinylene, piperazinylene, morpholinylene, thiomorpholinylene, thiazolidinylene, 1,4-dioxanylene, tetrahydrofuranylene and tetrahydrothiophenylene.

The term "heteroarylene" means a group obtained by removal of a hydrogen atom from a heteroaryl group. Non-limiting examples of heteroarylene include pyridylene, pyrazinylene, furanylene, thienylene and pyrimidinylene.

The term "alkylene" means a group obtained by removal of a hydrogen atom from an alkyl group. Non-limiting examples of alkylene include methylene and ethylene.

The term "alkenylene" means a group obtained by removal of a hydrogen atom from an alkene group.

The term "alkynylene" means a group obtained by removal of a hydrogen atom from an alkyne group.

The present invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides, and iodides; and aralkyl halides including benzyl and phenethyl bromides. Water or oil-soluble or dispersible products may be obtained by such quaternization.

The term "compounds of the invention" and equivalent expressions, are meant to embrace compounds herein described, which expression includes the prodrugs, the pharmaceutically acceptable salts, the oxides, and the solvates, e.g., hydrates, where the context so permits.

The term "method of treating" means amelioration or relief from the symptoms and/or effects associated with the disorders described herein.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions and methods of treatment is provided as the salt form.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: "Design of Prodrugs," H. Bundgaard, ed., Elsevier (1985); "Methods in Enzymology," K. Widder et al, Ed., Academic Press, 42, p. 309-396 (1985); "A Textbook of Drug Design and Development," Krogsgaard-Larsen and H. Bundgaard, ed., Chapter 5; "Design and Applications of Prodrugs," p. 113-191 (1991); "Advanced Drug Delivery Reviews," H. Bundgard, 8, p. 1-38 (1992); *Journal of Pharmaceutical Sciences* 77:285 (1988); Nakeya et al, *Chem. Pharm. Bull.* 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

Compounds of formula (I) are commercially available and/or known and/or can be produced according to known methods. In one embodiment, compounds of formula (I) are prepared by reacting aldehydes of formula (VI)

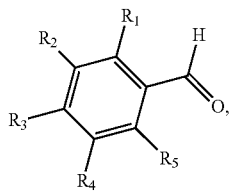

VI in which $R_1$-$R_5$ are as defined herein, with a compound of formula (VII)

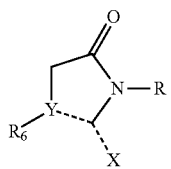

VII where R, $R_6$, X, and Y are as defined herein. This reaction can be carried out in an organic solvent, e.g., benzene, toluene, xylene, dioxane, dichloromethane, ethanol, or the like at room temperature to solvent-refluxing temperature, but the solvent refluxing temperature is preferable. Moreover, as a catalyst, addition of a secondary amine (e.g., piperidine or the like) or an acetic acid salt (e.g., ammonium acetate or the like) and acetic acid or benzoic acid is suitable.

In another embodiment, compounds of formula (I) can be produced by reacting compounds of formula (I) where R is H, and which themselves represent active ingredients, with suitable alkylation, acylation, or arylation agents.

The starting compounds (VI) and (VII) are commercially available, are known, or can be produced according to known methods.

A compound of formula (VIIa)

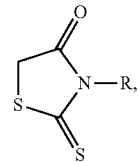

VIIa in which R is as defined herein, is prepared by reacting a compound of formula (VIII)

R—NH$_2$  VII with carbon disulfide, followed by a reaction with chloroacetic acid. The reaction between a compound of formula (VII) and carbon disulfide can be conducted in an organic solvent, e.g, ethyl ether at 0-5° C. Successive reaction with chloroacetic acid can be conducted in an organic solvent, e.g., alcohol such as ethanol at room temperature to the solvent refluxing temperature.

A compound of formula (VIIe)

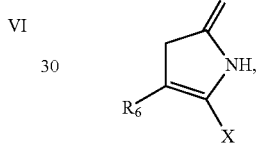

VIIc in which $R_6$ is as defined herein and X is $C_{1-6}$ alkyl, $C_{2-6}$ alkenyl, or $C_{2-6}$ alkynyl, can be prepared from a compound of formula (X) with ammonium acetate in acetic acid at the solvent refluxing temperature, according to the following scheme:

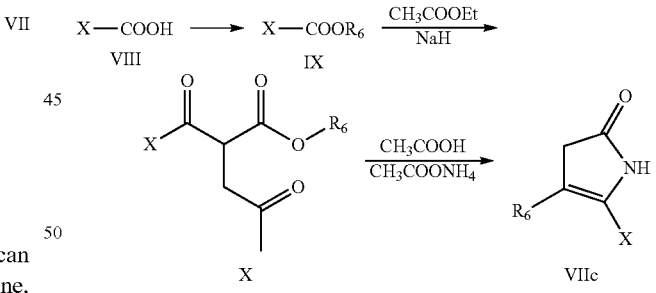

Compounds of formula (X) can be prepared by reacting compounds of formula (IX) with ethyl acetate. This reaction can be carried out in an organic solvent, e.g., 1-buthoxy-buthane or the like at room temperature to solvent-refluxing temperature. Moreover, as a base, addition of sodium hydride may be suitable.

Compounds of formula (IX) can be prepared by reacting compounds of formula (VIII) with alcohol such as ethanol in the presence of sulphuric acid as a catalyst. The reaction can be conducted at room temperature to solvent-refluxing temperature.

Compounds of formula (I) produced according to the methods described herein can be isolated and purified in a known manner, e.g., by subjecting the residue after distillation of the solvent to partition, extraction, re-precipitation, or re-crystallization or another purification method. In one embodiment, column chromatography on a suitable support or preparative middle or high pressure liquid chromatography (HPLC) is employed.

In one embodiment of the pharmaceutical composition of the present invention, the compound is a compound of formula (I) where R is selected from the group consisting of $CH_2R_7$, $CH_2C(O)R_7$, or $CH_2C(O)NHR_7$.

In another embodiment, the pharmaceutical composition of the present invention includes a compound of formula (I) where $R_7$ is unsubstituted or substituted with a halogen.

In another embodiment, the pharmaceutical composition of the present invention includes a compound of formula (I) where Y is S.

In yet another embodiment, the pharmaceutical composition of the present invention includes a compound selected from

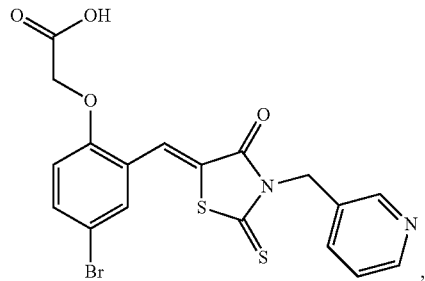

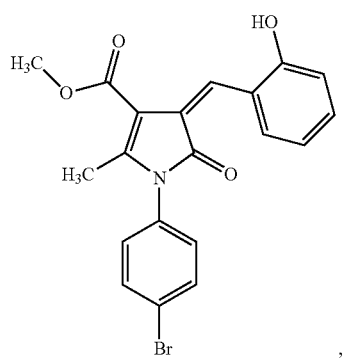

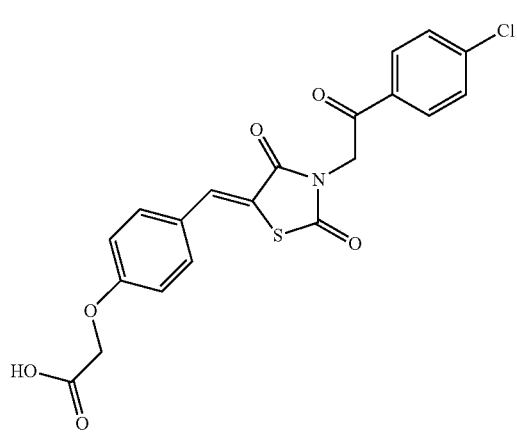

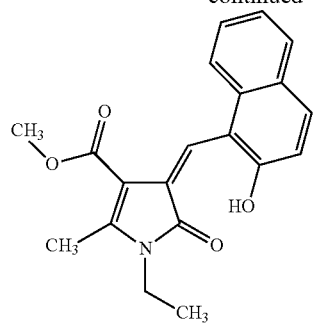

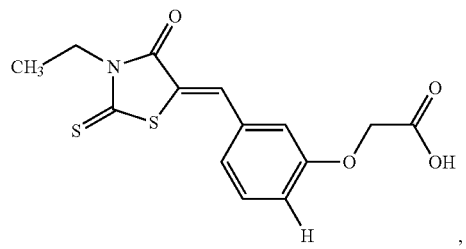

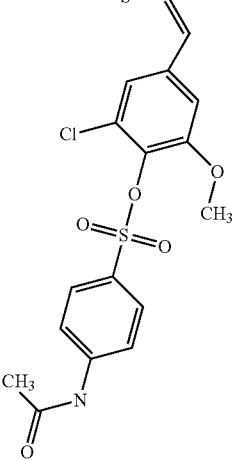

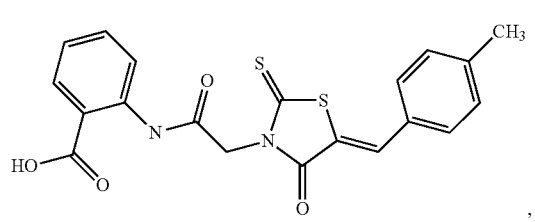

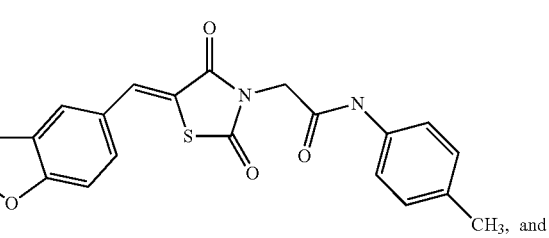

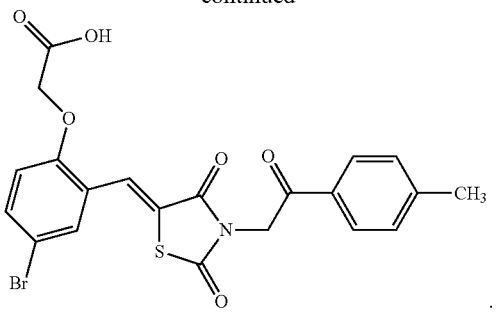

In a further embodiment, the pharmaceutical composition of the present invention includes a compound selected from

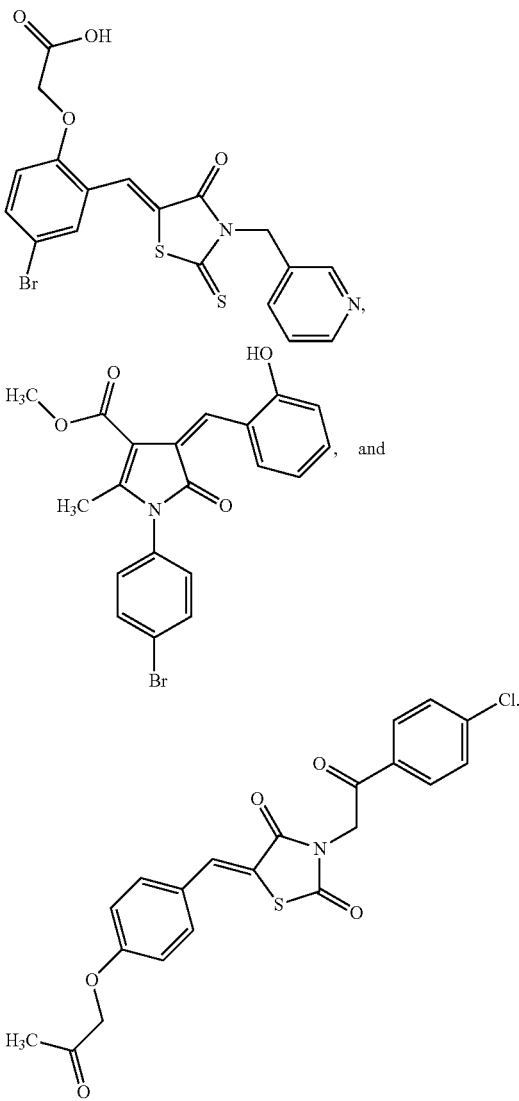

Another aspect of the present invention relates to a pharmaceutical composition comprising a compound of formula (II):

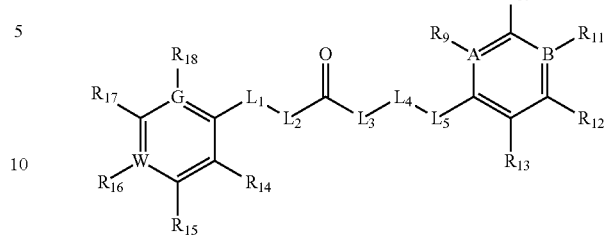

a stereoisomer, pharmaceutically acceptable salt, oxide, solvate, or ester thereof, where A is C or O;
B is C or absent;
G is C or S;
W is C or absent;
$L_1$ is independently selected from the group consisting of:
(1) absent;
(2) —C(S)NH—; or
(3)

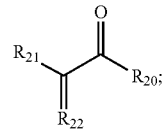

$L_2$ is NH or O;
$L_3$ is independently selected from the group consisting of:
(1) absent;
(2) —CH$_2$—;
$L_4$ is independently selected from the group consisting of:
(1) absent;
(2) —N(R$_{19}$)—;
(3) —R$_{24}$=N—N=CH—;
$L_5$ is independently selected from the group consisting of:
(1) absent;
(2) —C(O)—;
$R_9$ is H;
$R_{10}$ is H, halogen, $C_{1-6}$ alkyl, $C_{2-6}$ alkenyl, or $C_{2-6}$ alkynyl;
$R_{11}$ is H, halogen, NO$_2$, OCH$_2$COOR$_{23}$, OC(O)R$_{23}$, or OR$_{23}$;
$R_{12}$ is H or OR$_{23}$;
$R_{13}$ is H;
or when $L_4$ is —N(R$_{19}$)— and $L_5$ is —C(O)—, $R_{13}$ can combine with $R_{19}$ to form —C(O)—;
$R_{14}$ is H, OR$_{23}$, C(O)NH$_2$, or COOR$_{23}$;
$R_{15}$ is H, halogen, $C_{1-6}$ alkyl, $C_{2-6}$ alkenyl, $C_{2-6}$ alkynyl, or COOR$_{23}$;
$R_{16}$ is H, halogen, $C_{1-6}$ alkyl, $C_{2-6}$ alkenyl, $C_{2-6}$ alkynyl, —CH=R$_{24}$, or COOR$_{23}$;
$R_{17}$ is H, halogen, $C_{1-6}$ alkyl, $C_{2-6}$ alkenyl, $C_{2-6}$ alkynyl, or COOR$_{23}$;
$R_{18}$ is H, $C_{1-6}$ alkyl, $C_{2-6}$ alkenyl, $C_{2-6}$ alkynyl, OR$_{23}$, Or COOR$_{23}$;
$R_{20}$ is —NH—, —NH—N=CH—, or NH$_2$;
$R_{21}$ is —(CH$_2$)$_n$—, where n is 0 to 6;
$R_{22}$ is —CH— or —CHR$_{24}$;
$R_{23}$ is H, $C_{1-6}$ alkyl, $C_{2-6}$ alkenyl, or $C_{2-6}$ alkynyl;
$R_{24}$ is a monocyclic or polycyclic aryl, or a monocyclic or polycyclic heterocyclyl or heteroaryl containing 1-5 heteroatoms selected from the group consisting of nitrogen, oxygen, and sulfur, each $R_{24}$ being optionally substituted from 1-3 times with substituents selected from the group consisting of OH, $C_{1-6}$ alkyl, $C_{2-6}$ alkenyl, $C_{2-6}$ alkynyl, =O, =NH, $NH_2$, halogen, $COOR_{23}$ and
a pharmaceutically acceptable carrier.

Compounds of formula (II) are commercially available, or known, or can be produced according to known methods.

Compounds of formula (II), where $L_2$ is NH can be prepared by reacting carboxylic acids of formula (XI)

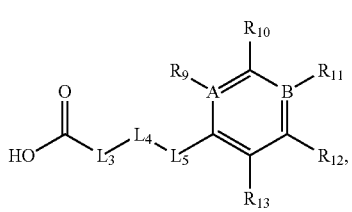
XI where $R_9$, $R_{10}$, $R_{11}$, $R_{12}$, $R_{13}$, $L_3$, $L_4$, $L_5$, A, and B are as defined herein, with compounds of formula (XII)

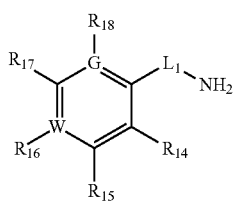
XII where $R_{14}$, $R_{15}$, $R_{16}$, $R_{17}$, $R_{18}$, $L_1$, G, and W are as defined herein (see U.S. Pat. No. 6,593,344 to Biedermann et. al., which is hereby incorporated by reference in its entirety).

Reactive derivatives of compounds of formula (XI) can be, e.g., activated esters, anhydrides, acyl benzotriazoles, acid halides (e.g., acid chlorides) or simple low alkyl esters. Suitable activated esters are, for example, p-nitrophenyl ester, 2,4,6-trichlorphenyl ester, pentachlorophenyl ester, cyanomethyl ester, esters of N-hydroxysuccinimide, N-hydroxyphthalimides, 1-hydroxybenzotriazole, N-hydroxypiperidine, 2-hydroxypyridine, or 2-mercaptopyridine, etc.

Anhydrides can be symmetric anhydrides or mixed, as they are obtained, e.g., with pivaloyl chloride or with chloroformates. Aromatic (e.g., chloroformic phenyl ester), araliphatic (e.g., chloroformic benzyl ester) or aliphatic chloroformates (e.g., chloroformic methyl ester, ethyl ester, or isobutyl ester) can be used for this.

Reaction of compounds of formula (XI) with the compounds of formula (XII) can also be carried out in the presence of condensation agents such as dicyclohexylcarbodiimide, 1-ethyl-3-(3-dimethylaminpropyl) carbodiimide hydrochloride, N,N'-carbonyldiimidazole, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazole, N-hydroxypiperidine, etc. can be advantageously added.

Compounds of formula (XII) can be used for reaction as free bases as well as in the form of their acid addition salts. For this, the salts of inorganic acids are to be preferred, i.e., hydrochlorides, hydrobromides, or sulfates to name a few.

Compounds of formula (XII) can be mono or polyamines. If a polyamine, then the use of a suitable nitrogen protecting group might be required, such as benzyl group, tert-butoxycarbonyl group, Fmoc, and Cbz. Methods describing incorporation and removal of the protecting groups are fully familiar to persons of ordinary skill in the art, and are also documented in various monographs (see, e.g., Wuts and Greene, "Green's Protective Groups in Organic Synthesis," John Wiley & Sons, 2006 which is hereby incorporated by reference in its entirety).

Reaction of compounds of formula (XI) or their reactive derivatives with compounds of formula (X) are normally carried out in a suitable, e.g., inert solvent. As examples, aromatic hydrocarbons such as benzene, toluene, xylene, halogenated hydrocarbons (for example dichloromethane, chloroform, 1,2-dichloroethane, trichloroethylene), or ethers such as for example diethyl ether, tetrahydrofuran, dioxane, glycol dimethyl ether, ethyl acetate, acetonitrile or polar aprotic solvents such as, for example, dimethylsulfoxide, dimethylformamide or N-methylpyrrolidone are to be named. Pure solvents, as well as mixtures of two or more, can be used.

The reaction temperatures can, depending on the reactivity of the starting materials, vary in a wide range. Generally, the reaction is carried out at temperatures between −40° C. and 180° C., or between −10° C. and 130° C., or at the boiling point of the solvent used.

The starting compounds (XI) and (XII) are known or can be produced according to known methods (see, e.g., U.S. Pat. No. 6,593,344 to Biedermann et al., which is hereby incorporated by reference in its entirety).

Compounds of formula (II) where $L_1$ has the following structure

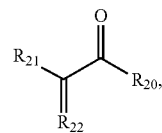

where $R_{20}$ is —NH—N=CH— can be prepared by reacting the corresponding compound of formula (II) where $R_{20}$ is OMe, with hydrazine hydrate ($N_2H_4 \cdot H_2O$) and a subsequent reaction with an aldehyde. The reaction between a compound of formula (II) and hydrazine hydrate can be carried out in an organic solvent, e.g., tetrahydrofuran or the like at room temperature. Subsequent reaction with an aldehyde can be carried out in organic solvent at room temperature.

Compounds of formula (II), where $L_2$ is O can be prepared by reacting carboxylic acids of formula (XI)

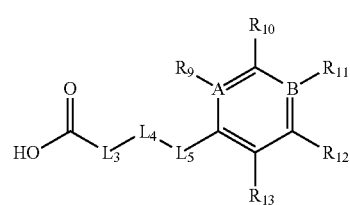
XI with compounds of formula (XIII)

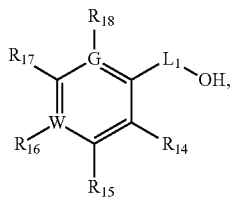

where $R_{14}$, $R_{15}$, $R_{16}$, $R_{17}$, $R_{18}$, $L_1$, G, and W are as defined herein. This reaction can be conducted in an organic solvent, e.g., ethyl acetate at room temperature.

Compounds of formula (II), where L1 is —C(S)NH— can be prepared by reacting acyl isothiocyanates of formula (XIV)

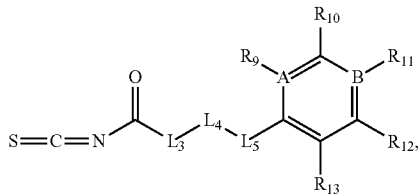

where $R_9$, $R_{10}$, $R_{11}$, $R_{12}$, $R_{13}$, $L_3$, $L_4$, $L_5$, A, and B are as defined herein, with an amine of formula (XV)

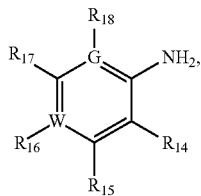

where $R_{14}$, $R_{15}$, $R_{16}$, $R_{17}$, $R_{18}$, G, and W are as defined herein (see Parmar et al., "Synthesis and Antibacterial Evaluation of Some Novel 2-Arylamino-4-phenyl-thiazolyl Derivatives," *Bull. Korean Chem. Soc.* 31(4):793-797 (2010); Pazdera et al., "2-(3-Acylthioureido)benzonitriles. I. Synthesis and cyclization reactions of 2-(3-acylthioureido)benzonitriles," *Chem. Papers* 45(4):527-540 (1991), which are hereby incorporated by reference in their entirety). This reaction can be conducted in an organic solvent, e.g., acetone at room temperature or at the solvent boiling temperature.

Compounds of formula (XIV) can be prepared by reacting an acyl chloride of formula (XVI)

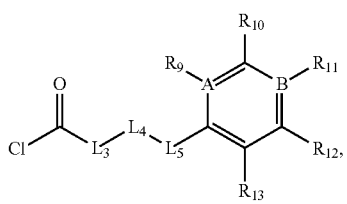

with potassium thiocyanate or ammonium thiocyanate. This reaction can be conducted in an organic solvent, e.g., acetone at room temperature or at the solvent boiling temperature.

Compounds of formula (II), where
$L_1$ is

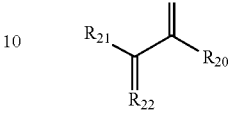

$R_{20}$ is —NH— or $NH_2$;
$R_{21}$ is —$(CH_2)_n$—, where n is 0; and
$R_{22}$ is —CH— or —$CHR_{24}$
can be prepared by reacting a compound of formula (XXI)

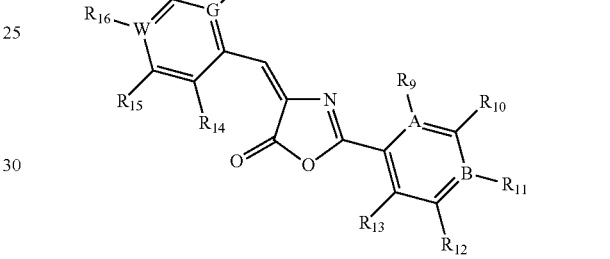

with ammonia and primary amines.

The reaction can be conducted in an organic solvent, e.g., benzene at the solvent boiling temperature.

Compounds of formula (XXI) can be prepared by reacting a compound of formula (XXII)

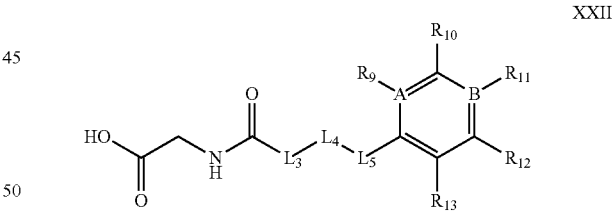

with aldehydes of the formula (XXIII)

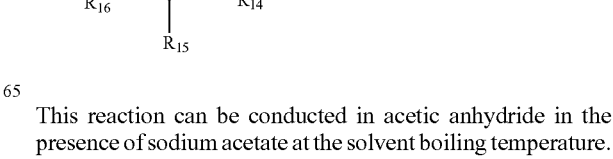

This reaction can be conducted in acetic anhydride in the presence of sodium acetate at the solvent boiling temperature.

Compounds of formula (XXII) can be prepared by reacting an acyl chloride of formula (XXIV)

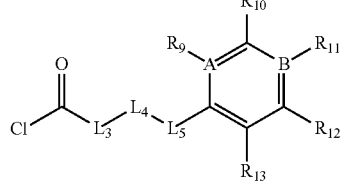

XXIV with glycine in the presence of the aqueous base. This reaction can be conducted in an aqueous sodium hydroxide solution at 10° C. to 15° C.

Compounds of formula (II) produced according to the methods described herein can be isolated and purified in a known manner, e.g., by subjecting the residue after distillation of the solvent to partition, extraction, re-precipitation, or re-crystallization or another purification method. Column chromatography on a suitable support or preparative middle or high pressure liquid chromatography (HPLC) may also be employed.

According to one embodiment, the pharmaceutical composition of the present invention includes a compound of formula (II) where $L_3$, $L_4$, and $L_5$ are absent.

In another embodiment, the pharmaceutical composition of the present invention includes a compound of formula (II), where $L_1$ is

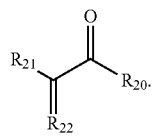

According to another embodiment, the pharmaceutical composition of the present invention includes a compound of formula (II) where A, B, G, and W are all C.

In yet another embodiment, the pharmaceutical composition includes a compound of formula (II) where $L_1$ and $L_2$ are absent.

In a further embodiment, the pharmaceutical composition of the present invention includes a compound selected from

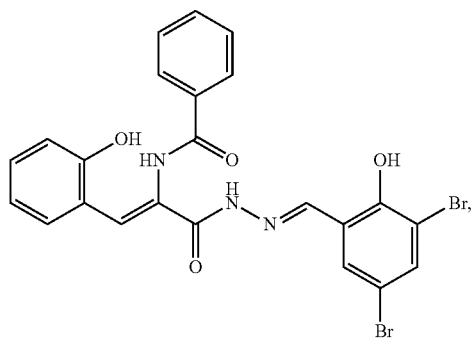 [SMILES: O=C(N/N=C/c1cc(Br)cc(Br)c1O)/C(=C/c1ccccc1O)NC(=O)c1ccccc1]

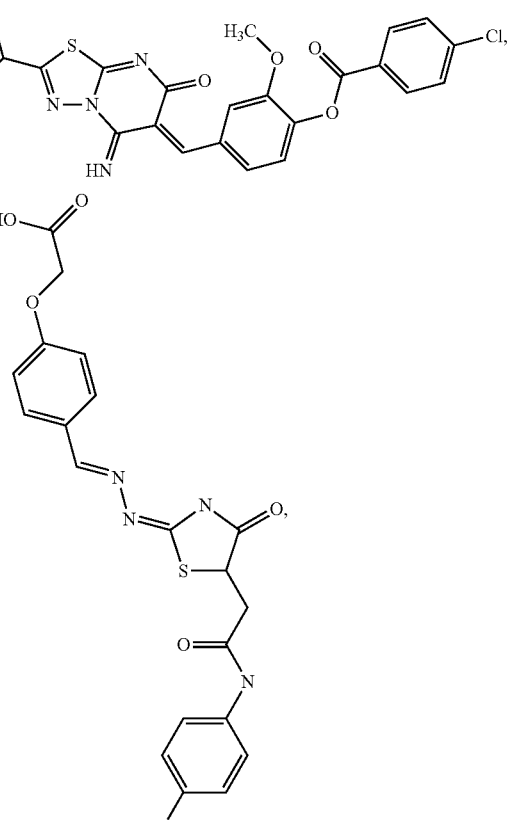

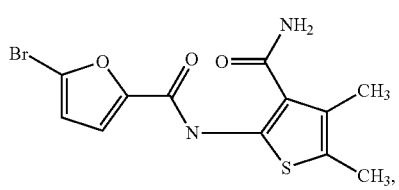

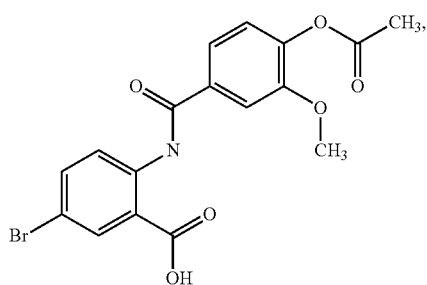

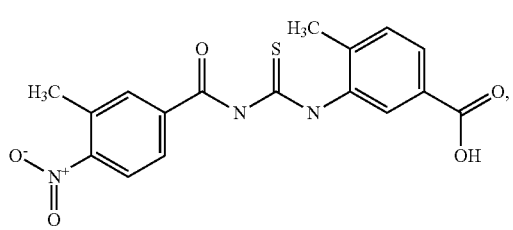

-continued

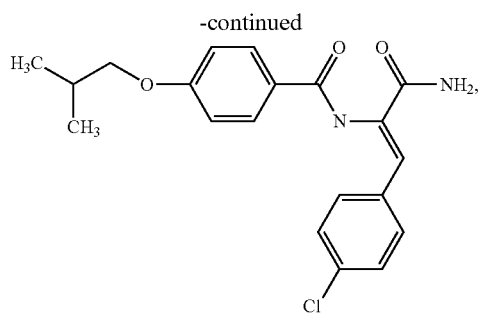

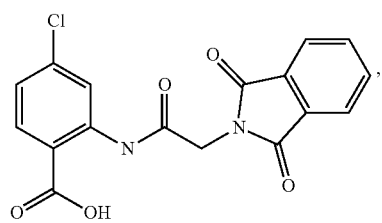

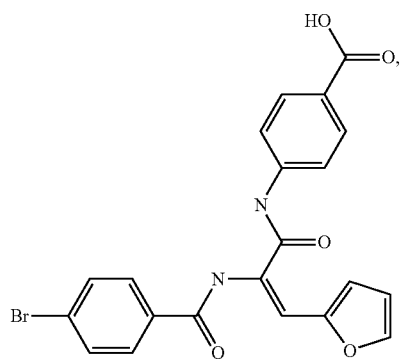

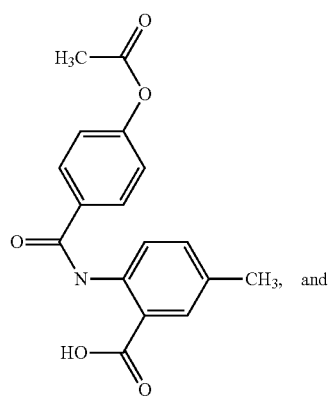

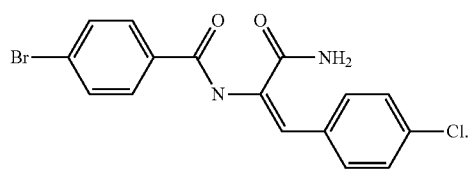

In still another embodiment, the pharmaceutical composition of the present invention includes a compound of formula:

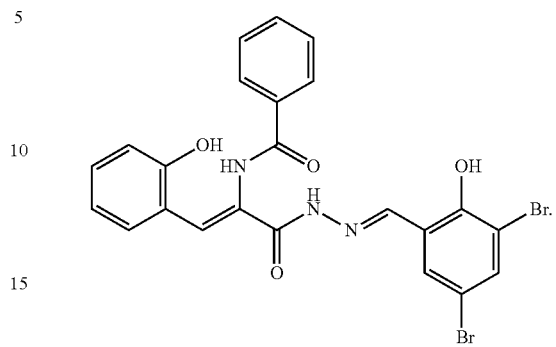

A further aspect of the present invention is directed to a pharmaceutical composition comprising a compound of formula (III):

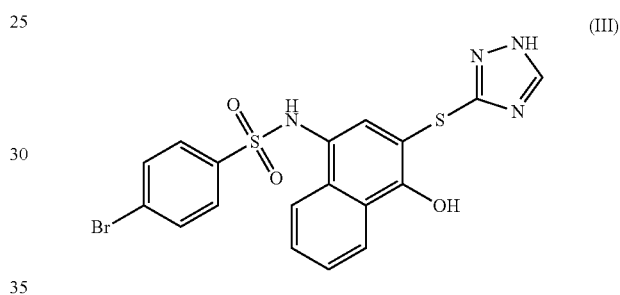

(III)

a stereoisomer, pharmaceutically acceptable salt, oxide, solvate, or ester thereof and a pharmaceutically acceptable carrier.

A compound of formula (III) can be prepared by reacting a compound of formula (XVI)

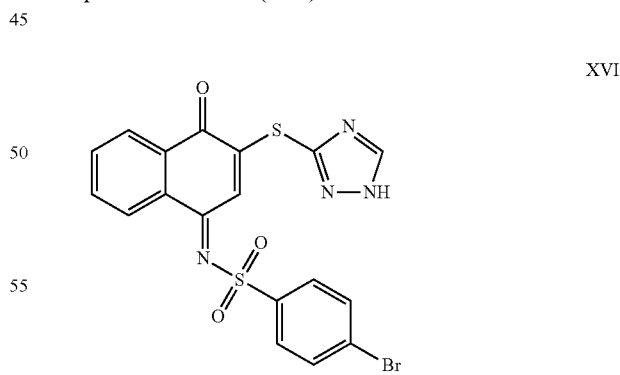

XVI with sodium hydrosulfite ($Na_2S_2O_4$) (Qin et al., "Identification of a Novel Family of BRAF$^{V600E}$ inhibitors," *J. Med. Chem*, 2012, 55:5220-5230; US 2012/0142917 to Lawrence et al., which are hereby incorporated by reference in its entirety). This reaction can be conducted in an organic solvent, e.g., ethyl acetate at room temperature. Addition of water to the reaction mixture may be desirable.

A compound of formula (XVI) can be prepared by reacting a compound of formula (XVII)

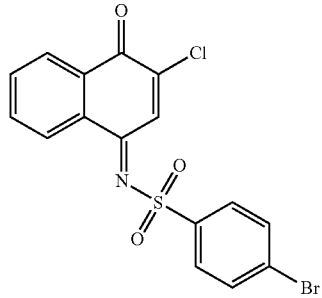

XVII

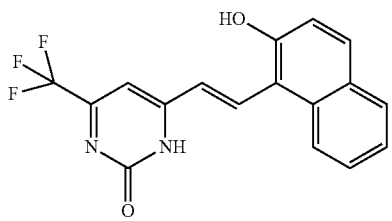

IV a stereoisomer, pharmaceutically acceptable salt, oxide, solvate, or ester thereof and a pharmaceutically acceptable carrier. This compound can be prepared by reacting the aldehyde of formula (X)

with a thiol compound of formula (XVIII)

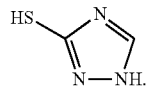

XVIII

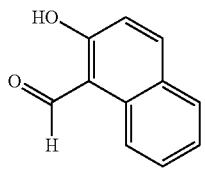

XXII

This reaction can be carried out in an organic solvent, e.g., tetrahydrofuran or the like at room temperature.

A compound of formula (XVII) can be prepared by reacting a 2-chloro-1,4-naphtoquinone compound of formula (XIX)

with the pyrimidone of formula (XXIII)

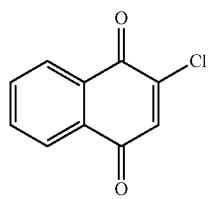

XIX

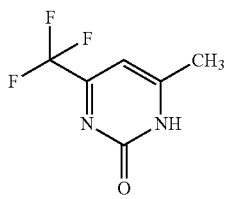

XXIII with a sulfonamide compound of formula (XX)

(see e.g., EP 1389461 to Missio et al., which is hereby incorporated by reference in its entirety). This reaction can be carried out in an organic solvent, e.g., ethanol or the like at solvent refluxing temperature. Addition of a secondary amine, such as piperidine or the like may be suitable.

The pyrimidone of formula (XXIII) can be produced by reacting the 1,3-diketone of formula (XXIV)

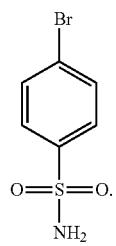

(XX)

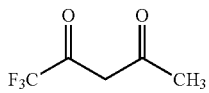

XXIV

This reaction can be carried out in an organic solvent, e.g., dichloromethane or tetrahydrofuran. Addition of titanium chloride (TiCl$_4$) at 0° C. is suitable. The reaction can be conducted at 60° C. with microwave assisted heating. This reaction can also be carried out in the presence of a triethyl amine.

A further aspect of the present invention relates to a pharmaceutical composition comprising a compound of formula (IV)

with urea. This reaction can be conducted in an organic solvent (ethanol or the like) or a mixture of the solvents, e.g., ethanol/water (1:1) at solvent refluxing temperature. Addition of a concentrated mineral acid, such as hydrochloric or sulfuric acid, is required.

Another aspect of the present invention is directed to a pharmaceutical composition comprising a compound of formula (V):

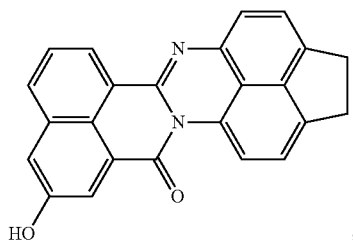
(V)

a stereoisomer, pharmaceutically acceptable salt, oxide, solvate, or ester thereof and a pharmaceutically acceptable carrier. This compound can be purchased from different suppliers, including ChemBridge Corporation.

A further aspect of the present invention is directed to a method of treating cancer in a subject. This method involves selecting a subject with cancer and administering to the subject a compound of formulae (I)-(V) as defined herein under conditions effective to treat cancer in the subject.

Administering of compounds and/or pharmaceutical compositions to a subject may involve administering therapeutically effective amounts, which means an amount of compound effective in treating the stated conditions and/or disorders in a subject. Such amounts generally vary according to a number of factors well within the purview of ordinarily skilled artisans given the description provided herein. These include, without limitation, the particular subject, as well as its age, weight, height, general physical condition, and medical history, the particular compound used, as well as the carrier in which it is formulated and the route of administration selected for it, and the nature and severity of the condition being treated.

Administering typically involves administering pharmaceutically acceptable dosage forms, which means dosage forms of compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

Administering may be carried out orally, intradermally, intramuscularly, intraperitoneally, intravenously, subcutaneously, or intranasally. Compounds may be administered alone or with suitable pharmaceutical carriers, and can be in solid or liquid form, such as tablets, capsules, powders, solutions, suspensions, or emulsions.

Cancers amenable to the treatment method of the present invention include, without limitation, multiple myeloma; lymphoma; mantle cell lymphoma; melanoma; leukemia; sarcoma; glioblastoma; nasopharyngeal carcinoma; stomach (gastric) cancer; renal cancer; ovarian cancer; oral cancer; breast cancer; rectal cancer; cancers of the pancreas, prostate, colon, lung, liver, thyroid, skin, gallbladder, and biliary tract (see Wang et al., "Skp2: A Novel Potential Therapeutic Target for Prostate Cancer," *Biochimica et Biophisica Acta* 1825:11-17 (2012); Hershko, "Oncogenic Properties and Prognostic Implications of the Ubiquitin Ligase Skp2 in Cancer," Cancer 112(7):1415-1424 (2008), which are hereby incorporated by reference in their entirety); and endometrial cancers.

Another aspect of the present invention relates to a method of inhibiting SCF-Skp2 activity. This method involves administering to cells a compound of formulae (I)-(V) as defined herein under conditions effective to inhibit SCF-Skp2 activity in the cell.

In one embodiment, this method of the present invention is carried out in vitro, such as in a sample. In vitro methods may be carried out to test the activity of certain compounds and/or pharmaceutical compositions against cells in, e.g., a solution or a tissue sample, for their ability to inhibit SCF-Skp2 activity.

In another embodiment, this method of the present invention is carried out in vivo in an animal or patient or subject.

Inhibiting SCF-Skp2 activity may be accomplished in a cell by any mechanism of action. Without being bound by theory, it is believed that inhibiting SCF-Skp2 activity may be achieved according to one embodiment by targeting a compound to bind to and/or fit in the p27-binding interface of a Skp2-Cks 1 complex.

The methods of treating and inhibiting of the present invention may also be carried out in combination with other molecules that have activity at or near the p27-binding interface of a Skp2-Cks 1 complex. Thus, according to one embodiment, methods are carried out by administering a cks-dependent inhibitor (e.g., the Skp2 inhibitors (a compound of formulae (I)-(V)) of the present invention) with a cks-independent inhibitor and/or other proteasome inhibitors and/or any other cancer drugs. For example, and without limitation, a suitable combination may include a compound of formulae (I)-(V) of the present invention with one or more compounds that target the following sites: cyclin dependent kinase (CDK), the interface of Skp1-Skp2 (CpdA), SMIP004, MLN4924, CDC34, E1, and Bortezomib (see Bautista and Wolf, "Skipping Cancer: Small Molecule Inhibitors of SKP2-Mediated p27 Degradation," *Chem. & Biol.* 19:1497-1498 (2012) and Chan et al., "Pharmacological Inactivation of Skp2 SCF Ubiquitin Ligase Restricts Cancer Stem Cell Traits and Cancer Progression," *Cell* 154:556-568 (2013), which are hereby incorporated by reference in their entirety).

Another aspect of the present invention relates to a method of identifying inhibitors of SCF-Skp2 activity. This method involves providing a model comprising a p27-binding interface of a Skp2-Cks 1 complex; providing one or more candidate compounds; evaluating contact between the candidate compounds and the model to determine which of the one or more candidate compounds have an ability to bind to and/or fit in the p27-binding interface of a Skp2-Cks 1 complex; and identifying compounds which, based on said evaluating, have the ability to bind to and/or fit in the p27-binding interface of a Skp2-Cks 1 complex as compounds potentially useful as inhibitors of SCF-Skp2 activity.

Providing a model comprising a p27-binding interface of a Skp2-Cks 1 complex may be carried out by using methods known and used by persons of ordinary skill in the art. In one embodiment, a cell is provided which expresses, e.g., Skp2 and Cks 1. To this end, a nucleic acid molecule encoding the desired polypeptide or protein can be introduced into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, e.g. AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others including, but not limited to, lacUV 5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno sequence about 7-9 bases 5' to the initiation codon (e.g., ATG) to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The protein-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a protein (e.g., Skp2 and/or Cks 1) is inserted into a vector in the sense (i.e., 5'→3') direction, such that the open reading frame is properly oriented for the expression of the protein under the control of a promoter of choice. Single or multiple nucleic acids may be ligated into an appropriate vector in this way, under the control of a suitable promoter, to prepare a nucleic acid construct.

Once the isolated nucleic acid molecule encoding the protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

It may be beneficial in carrying out this method of the present invention to knock down the expression of cellular proteins. Inhibitory nucleic acid (RNAi) molecules that interfere with protein expression e.g., to cause a reduction in protein expression levels are known. In the field RNAi technology, siRNA, miRNA or shRNA, or other RNAi inducing agents may be used. RNA interference is a multistep process and is generally activated by double-stranded RNA that is homologous in sequence to the targeted transcript.

In vitro transcription/translation systems using rabbit reticulocyte lysate is a helpful technique that uses rabbit reticulocyte lysate to supply the machinery needed for human protein to be made from a plasmid in a cell free system. This type of system is commonly used for the identification of mRNA species, the characterization of their protein products, and the investigation of transcriptional and translational control. Rabbit reticulocyte lysate is prepared from New Zealand white rabbits using a standard protocol that ensures reliable and consistent reticulocyte production in each lot. The reticulocytes are purified to remove contaminating cells, which could otherwise alter the translational properties of the final extract. After the reticulocytes are lysed, the extract is treated with micrococcal nuclease to destroy endogenous mRNA and thus reduce background translation to a minimum. The lysate contains the cellular components necessary for protein synthesis (tRNA, ribosomes, amino acids, initiation, elongation, and termination factors). Rabbit reticulocyte lysate may contain a variety of post-translational processing activities, including acetylation, isoprenylation, and some phosphorylation activity. Processing events such as signal peptide cleavage and core glycosylation can be examined by adding canine pancreatic microsomal membranes to a standard translation reaction.

Methods of identifying compounds that bind and/or fit in the p27-binding interface of a Skp2-Cks 1 complex can also be carried out in a cell-free format.

In one embodiment, the assay is directed to the identification of a compound that binds and/or fits in the p27-binding interface of a Skp2-Cks 1 complex. This method involves combining the p27-binding interface of a Skp2-Cks 1 complex in the presence of a test compound under conditions effective to measure binding and/or interaction of the compound with the p27-binding interface of a Skp2-Cks 1 complex. Detection of binding and/or interaction can be achieved through any suitable procedure that is known in the art or hereafter developed. Exemplary procedures for use in a cell-free format include, without limitation, a competitive binding assay, direct measurement, or detecting changes in e.g., the activity of a protein or protein complex.

The assay methods of the present invention can be accomplished in any vessel suitable for containing the reactants. Examples of such vessels include, without limitation, microtiter plates, test tubes, and micro-centrifuge tubes.

In one approach, a fusion protein can be provided which adds a domain that allows the p27-binding interface of a Skp2-Cks 1 complex to be bound to a matrix. For example, the p27-binding interface of a Skp2-Cks 1 complex, or portion thereof, can be adsorbed onto glutathione sepharose beads (Sigma Chemical; St. Louis, Mo.) or glutathione derivatized microtiter plates, which are then combined with the test compound or the test compound and either the non-adsorbed protein(s), and the mixture incubated under conditions conducive to complex formation (e.g., at physiological conditions for salt and pH). Following incubation, the beads or microtiter plate wells are washed to remove any unbound components, the matrix immobilized in the case of beads, and complex determined either directly or indirectly, for example, as described above. Alternatively, the complexes can be dissociated from the matrix, and the level of protein binding or activity determined using standard techniques.

Other techniques for immobilizing proteins on matrices can also be used in the screening assays of the invention. For example, the protein of interest can be immobilized utilizing conjugation of biotin and streptavidin. Biotinylated protein can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with certain proteins (e.g., Skp2 and/or Cks 1), but which do not interfere with their binding, can be derivatized to the wells of the plate, and unbound protein trapped in the wells by antibody conjugation. Methods for detecting such complexes, in addition to those described above for the GST-immobilized complexes, include immunodetection of complexes using antibodies reactive with the protein, as well as enzyme-linked assays which rely on detecting an enzymatic activity associated with the protein.

According to one embodiment, this method of the present invention further involves screening the identified compounds in vitro for their ability to inhibit Skp2-mediated p27 ubiquitylation to alter cell cycle progression and designating the screened compounds which inhibit Skp2-mediated p27 ubiquitylation to alter cell cycle progression as useful therapeutics.

In another embodiment, the evaluating comprises using automated docking algorithm. Evaluating may involve analyzing electrostatic complementarity, Van Der Waals interactions, cation-π interactions, hydrophilic interactions, hydrophobic interactions, and/or hydrogen bonding between the candidate compounds and the first model by methods commonly employed by persons of ordinary skill in the art.

According to another embodiment, this method involves designing de novo compounds based on said identifying. Designing may involve, for example, linking functional groups or small molecule fragments of the identified compounds to form de novo compounds.

A further aspect of the present invention relates to a method of inhibiting SCF-Skp2 activity in a subject. This method involves selecting a subject in need of inhibiting Skp2-mediated p27 degradation; providing a compound which binds to and/or fits in a p27-binding interface of a Skp2-Cks 1 complex; and administering the compound to the selected subject under conditions effective to inhibit SCF-Skp2-mediated p27 degradation activity in the subject.

According to one embodiment, administering is carried out in vivo.

In another embodiment, administering is carried out orally, topically, transdermally, parenterally, subcutaneously, intravenously, intramuscularly, intraperitoneally, by intranasal instillation, by intracavitary or intavesical instillation, intraocularly, intraarterially, intralesionally, or by application to mucous membranes.

According to another embodiment, the subject is a mammal, such as human.

Another aspect of the present invention relates to methods of administering compounds of the present invention to assist in stem cell isolation, stem cell maintenance in culture, organogenesis, and bone marrow transplantation (Wang et al. "The Role of Skp2 In Hematopoietic Stem Cell Quiescence, Pool Size, and Self-renewal," *Blood* 118(20):5429-5438 (2011) and Rodriguez et al., "The SKP2 E3 Ligase Regulates Basal Homeostasis and Stress-induced Regeneration of HSCs," *Blood* 117(24):6509-6519 (2011), which are hereby incorporated by reference in their entirety).

EXAMPLES

The following examples are provided to illustrate embodiments of the present invention but are by no means intended to limit its scope.

Example 1

Identification of Small Molecule Inhibitors

The published Skp2-Cks1-p27 crystal structure (FIG. 1A, top) was interrogated with ICM-PocketFinder (Molsoft LLC, La Jolla, San Diego) (Hao et al., "Structural Basis of the Cks1-dependent Recognition of p27(Kip1) by the SCF (Skp2) Ubiquitin Ligase," *Mol. Cell* 20:9-19 (2005), which is hereby incorporated by reference in its entirety). Removal of the p27 peptide revealed a pocket formed jointly by Skp2 and Cks1 (FIG. 1A, bottom), and flanked by residues Skp2-R294, Skp2-Y346, Cks1-R44, and Cks1-Q52, which are essential for p27 binding and/or ubiquitylation (Hao et al., "Structural Basis of the Cks1-dependent Recognition of p27 (Kip1) by the SCF(Skp2) Ubiquitin Ligase," *Mol. Cell* 20:9-19 (2005); Sitry et al., "Three Different Binding Sites of Cks1 are Required for p27-ubiquitin Ligation," *J. Biol. Chem.* 277: 42233-42240 (2002); Ungermannova et al., "Ubiquitination of p27Kip1 Requires Physical Interaction with Cyclin E and Probable Phosphate Recognition by SKP2," *J. Biol. Chem.* 280:30301-30309 (2005), which are hereby incorporated by reference in their entirety). The pocket's area and volume fall within a range calculated to be permissive for drug-like small molecule binding (An et al., "Comprehensive Identification of 'Druggable' Protein Ligand Binding Sites," *Genome Inform.* 15:31-41 (2004); Cardozo et al., "Druggability of SCF Ubiquitin Ligase-protein Interfaces," *Methods Enzymol.* 399:634-653 (2005), which are hereby incorporated by reference in their entirety). This pocket was targeted in a virtual screen (ICM-VLS) of 315,000 diverse compounds (ChemBridge Corp., La Jolla, Calif.) and from the 202 VLS hits 96 compounds were selected based on calculated binding score and Lipinski properties (Lipinski et al., "Experimental and Computational Approaches to Estimate Solubility and Permeability in Drug Discovery and Development Settings," *Adv. Drug Deliv. Rev.* 46:3-26 (2001), which is hereby incorporated by reference in its entirety).

Figure 2A:
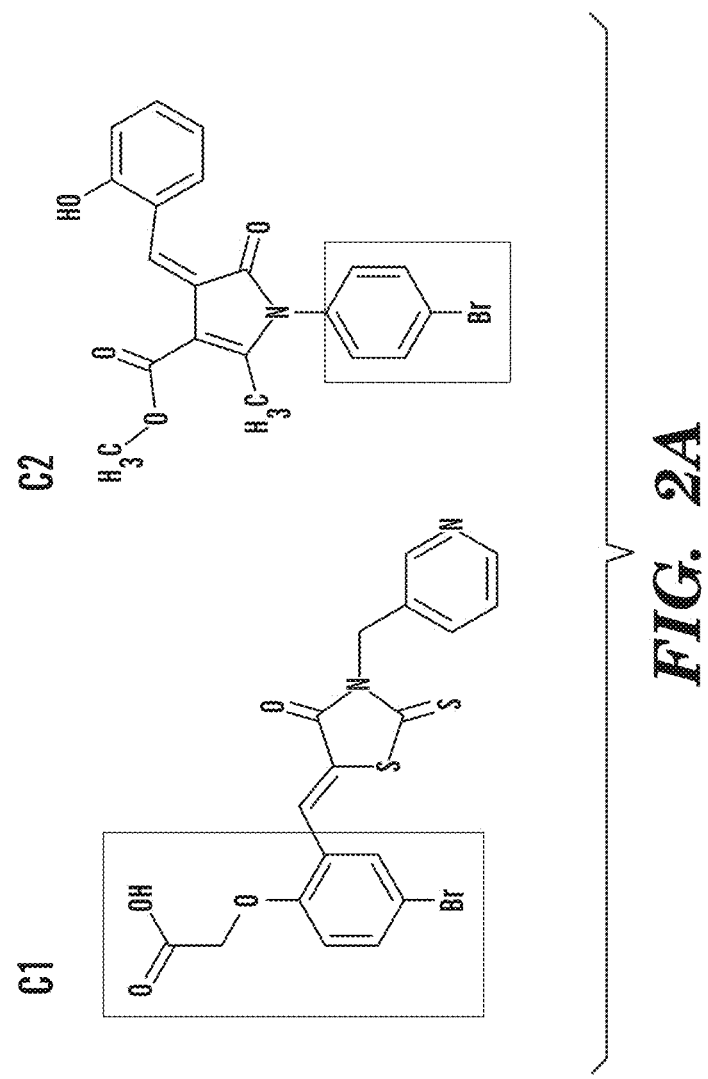
Figures 6A, 6B:
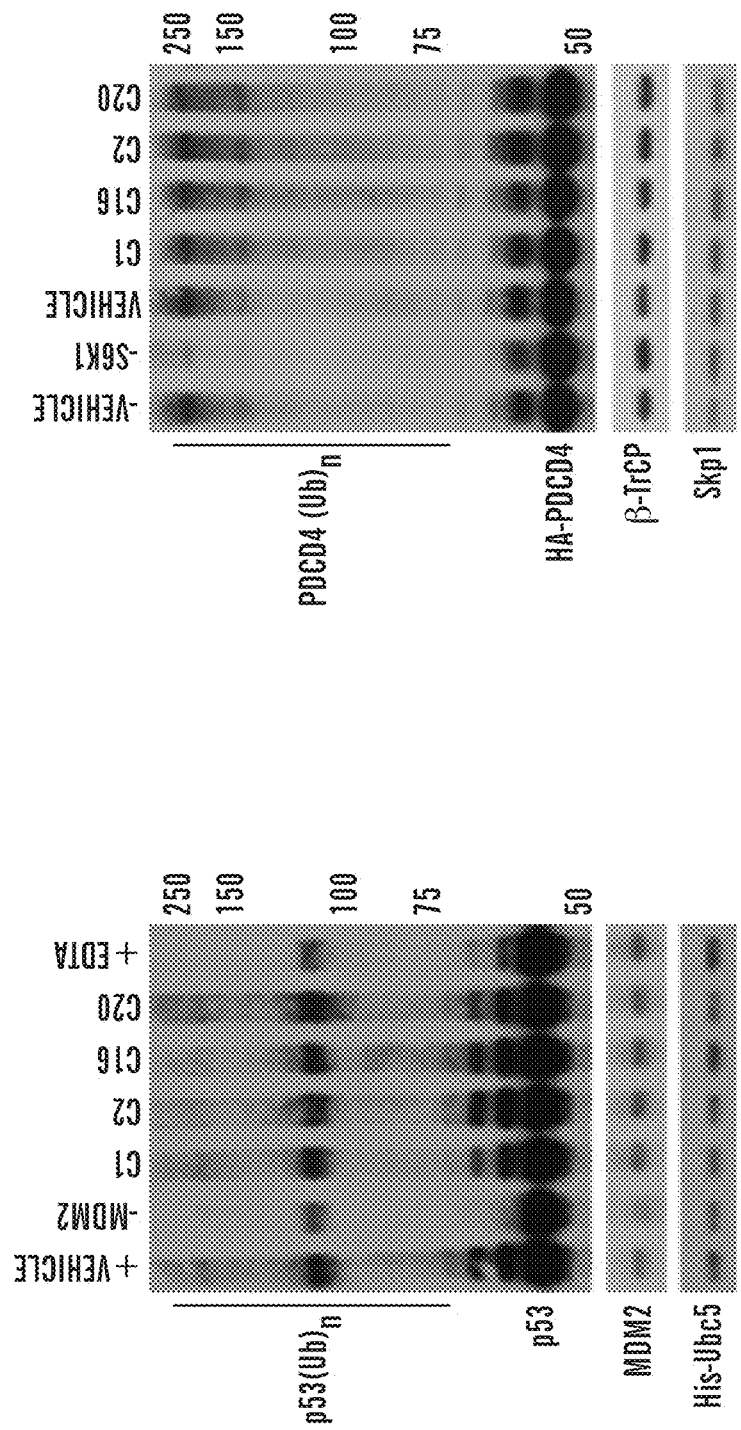
FIGS. 6A-D show testing results for specificity of inhibitors against Skp2.

The 96 hits were tested in an in vitro ubiquitylation assay driven by in vitro transcribed/translated Skp2, Cks1, and p27 (Sitry et al., "Three Different Binding Sites of Cks1 are Required for p27-ubiquitin Ligation," *J. Biol. Chem.* 277: 42233-42240 (2002)). Assay sensitivity was established for various criteria (FIG. 1B): Enhanced ubiquitylation with Cks1 (lane 2), kinase activity requirement (lane 3), and responsiveness to known inhibitors of Cullin (lane 5) or Cdk2 (lane 6) activity (Meijer et al., "Biochemical and Cellular Effects of Roscovitine, a Potent and Selective Inhibitor of the Cyclin-dependent Kinases cdc2, cdk2 and cdk5," *Eur. J. Biochem.* 243:527-536 (1997); Soucy et al., "An Inhibitor of NEDD8-activating Enzyme as a New Approach to Treat Cancer," *Nature* 458:732-736 (2009), which are hereby incorporated by reference in their entirety). Compounds showing at least 50% inhibition of Skp2-mediated p27 ubiquitylation (FIG. 1C) were counter-screened for inactivity against two anti-target E3 ligases: MDM2 and SCF-βTrCP (FIGS. 6A-B). Compounds C1 and C2 were identified from the primary VLS and C16 and C20 were identified from a second VLS (FIG. 2).

Figure 6D:
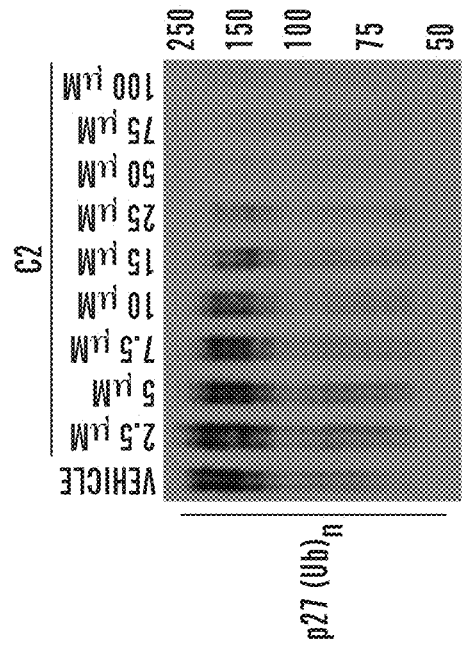
Figure 6C:
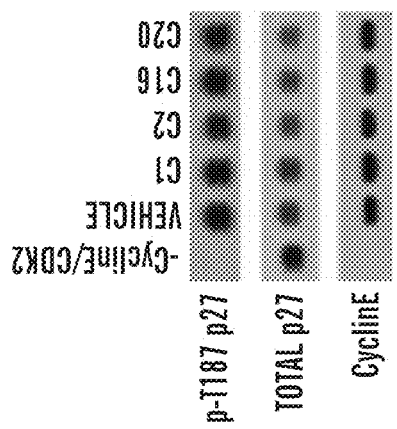

Secondary bioassays confirmed selectivity for Skp2-Cks1 interface by testing compound effects on ubiquitin transfer to either E2-Ubc3 or E2-Ubc5, as observed when ATP or E1 is omitted (FIG. 1D), level of CyclinE/CDK2 phosphorylation of p27 (FIG. 6C), and dose dependent inhibition of Skp2 ligase activity (FIG. 6D). In addition, C1 reduced the amount of p27, but not Skp1, interacting with Skp2 (FIG. 1E) to a level similar to the amount of p27 bound in the absence of Cks1 (FIG. 1E, lane 1 versus 3), suggesting that inhibitor activity is dependent on Cks1. Taken together, this approach identified a set of inhibitors that fit into a molecular surface pocket at the Skp2-Cks1 interface and block p27 ubiquitylation in vitro, but do not block the non-Skp2-p27 interfaces of the active SCF.

Example 2

Identification of Contacts Responsible for Inhibitor Activity

To identify the chemical groups responsible for inhibitor activity, divergent compounds sharing a common R-group with C1 or C2 (FIG. 2A, highlighted in box) were selected from the PubChem database and docked in silico to the pocket at the Skp2-Cks1 interface. Compounds were tested in vitro if they preferentially docked in positions similar to C1 or C2 (FIG. 2B): Either forming predicted electrostatic interactions with Cks1-Q52 and/or hydrogen bonding to Cks1-R44 or Skp2-R344 (as in C1) or predicted cation-π interaction with Skp2-R294, and/or a hydrogen bond to Cks 1-R44 (as in C2).

Figure 7A:
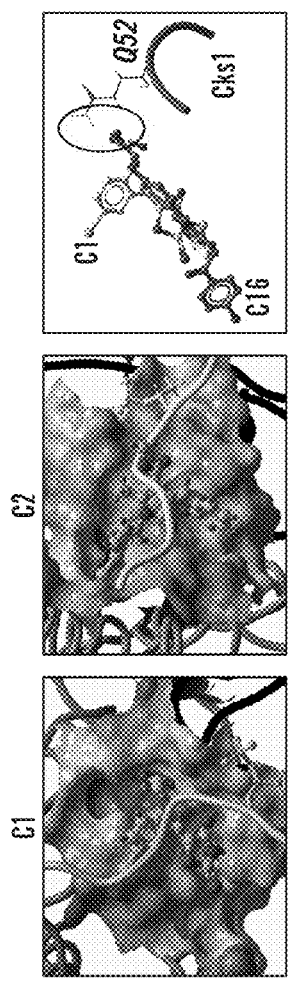
FIGS. 7A-C show that receptor (Skp2-Cks1)-compound interaction is required for activity.

C16 and C20 were identified using this method (FIG. 2C) and showed similar inhibition as C1 or C2 (FIG. 2D, lane 2 versus 5 and lane 7 versus 9) and parallel docking poses (FIG. 7A).

Figure 8A:
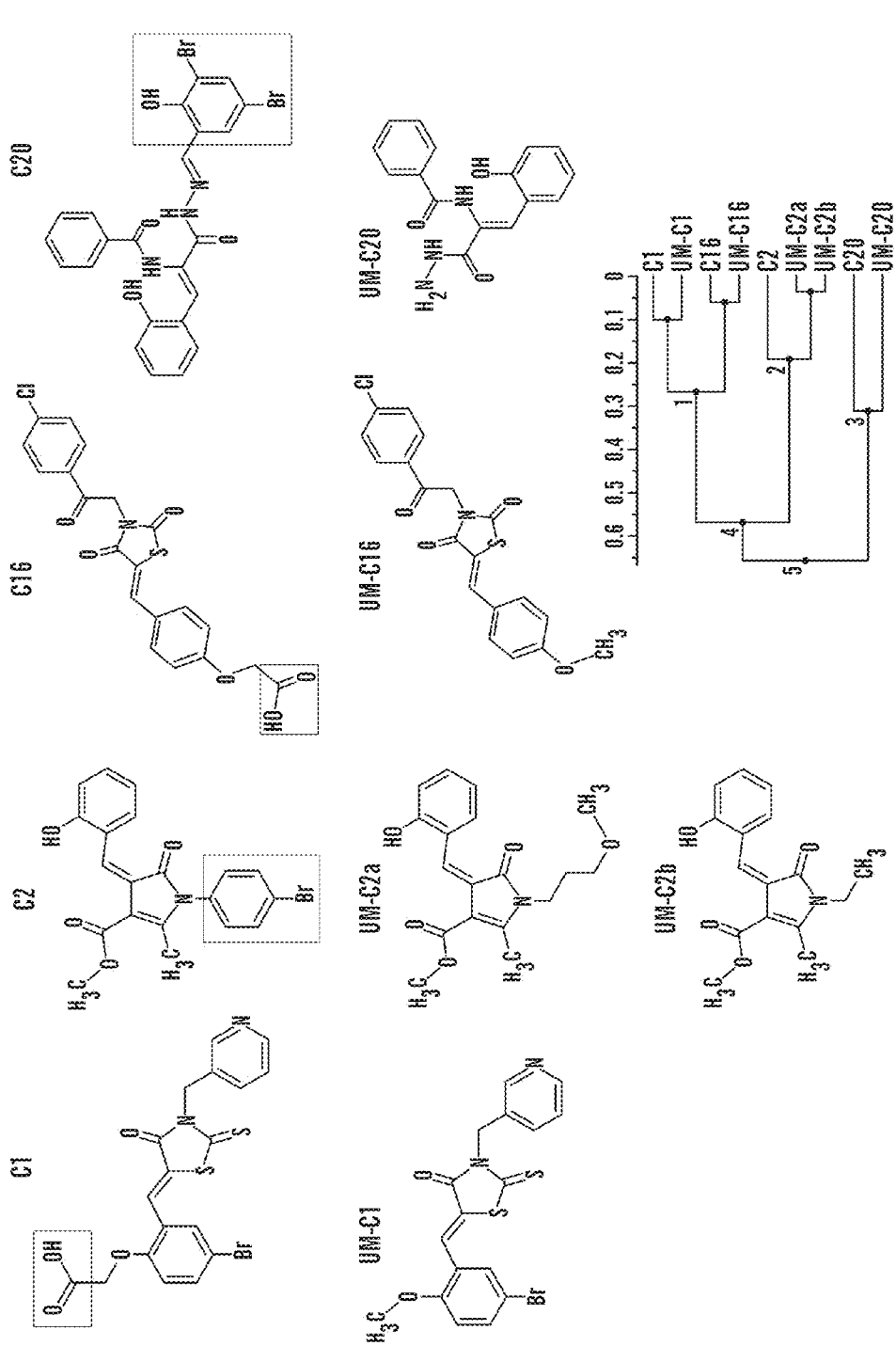
FIGS. 8A-C relate to the structures of active and inactive compounds, and SPR binding curves.
Figure 8B:
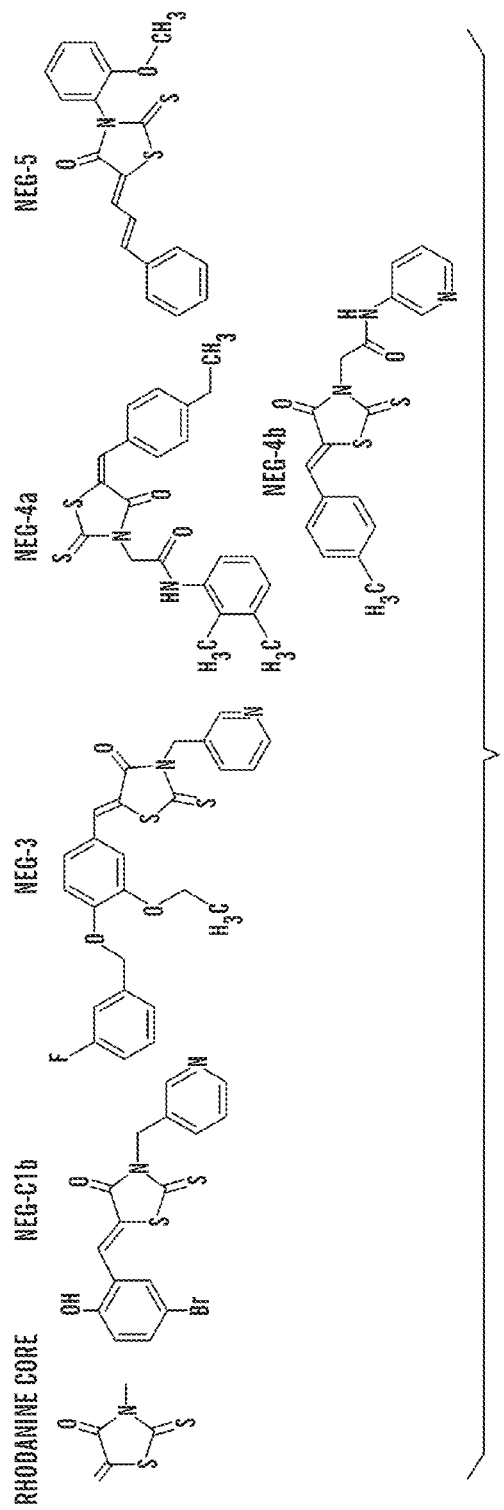

To test the necessity of the predicted chemical contact group, compounds sharing the same scaffold but differing in the key R-group listed above (unmatched compounds; UM) were identified for each of the 4 active compounds (FIG. 8A). With loss of the contact R-group, levels of p27 ubiquitylation were restored to vehicle control levels (FIG. 2D, lane 1 versus 4, 6, 8, 10). Notably, UM-C2a (unmatched compound for C2) partially reduced p27 ubiquitylation (FIG. 2D, lane 1 versus 3), suggesting that both the distance and charge of the contact group is important for C2 activity. Compound C1 contains a potentially promiscuous rhodanine core, but this core chemical group was not sufficient to inhibit ubiquitylation (FIG. 8B). Thus, chemical fingerprints guided the identification of additional Skp2 ligase inhibitors, with key 3D structural chemical groups confirmed necessary for inhibiting p27 ubiquitylation.

Figure 7C:
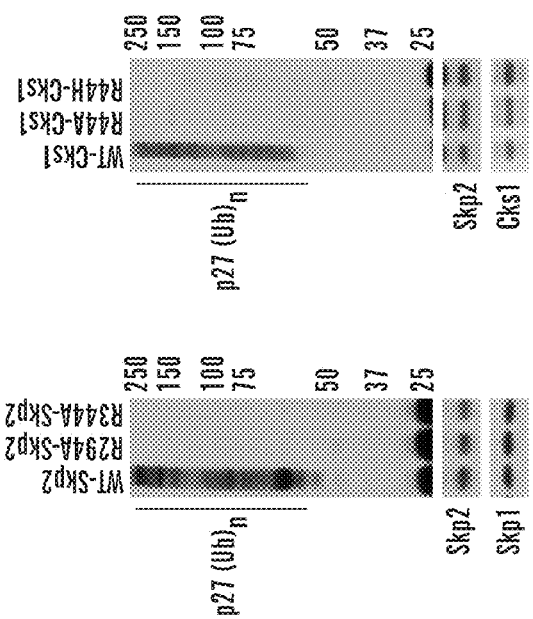
Figure 7B:
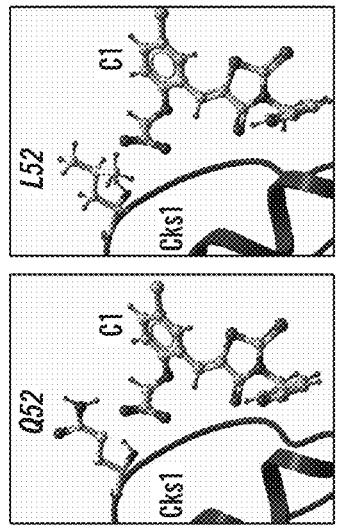

To interrogate the compound-contacting residues on the Skp2-Cks1 interface, mutants of Skp2 and Cks1 were designed based on the in silico dockings. The predicted electrostatic interactions between the positive charge on the $NH_2$ side group in Q52-Cks1 with the COOH-group in C1 and C16 should be lost when mutated to a neutral-charge leucine (FIG. 7B). In vitro ubiquitylation assays confirmed that C1 and C16 are active against Wild-Type Cks1 but are inactive against the Q52L-Cks 1 mutant (FIG. 2E). In contrast, C2 and C20 strongly inhibited the activity of both the Wild-Type Cks1 and the Q52L-Cks1 mutant. This confirms that the Q52-Cks1 residue is important for only C1 and C16 activity, as predicted by the in silico dockings. Notably, the basal level of ubiquitylation for the Q52L-Cks1 mutant was reduced (FIG. 2E, lane 1 versus 5), being the first report that Q52 contributes partially to p27 degradation. The Skp2-R294A and the Cks1-R44A/H mutants lacked ubiquitylation activity (FIG. 7C) preventing the interrogation of these residues' contribution to the activity of C2 and C20. R294A-Skp2 was previously shown to reduce p27 binding, suggesting that the predicted site for C2 and C20 binding correlates with ligase activity (Ungermannova et al., "Ubiquitination of p27Kip1 Requires Physical Interaction with Cyclin E and Probable Phosphate Recognition by SKP2," *J. Biol Chem.* 280:30301-30309 (2005), which is hereby incorporated by reference in their entirety). Thus, the predicted three-dimensional mode of interaction of the compounds with Skp2-Cks1 was validated at a chemical and protein level.

Example 3

Reduction of p27 Binding to Skp2 by the Inhibitors

Figure 2B:
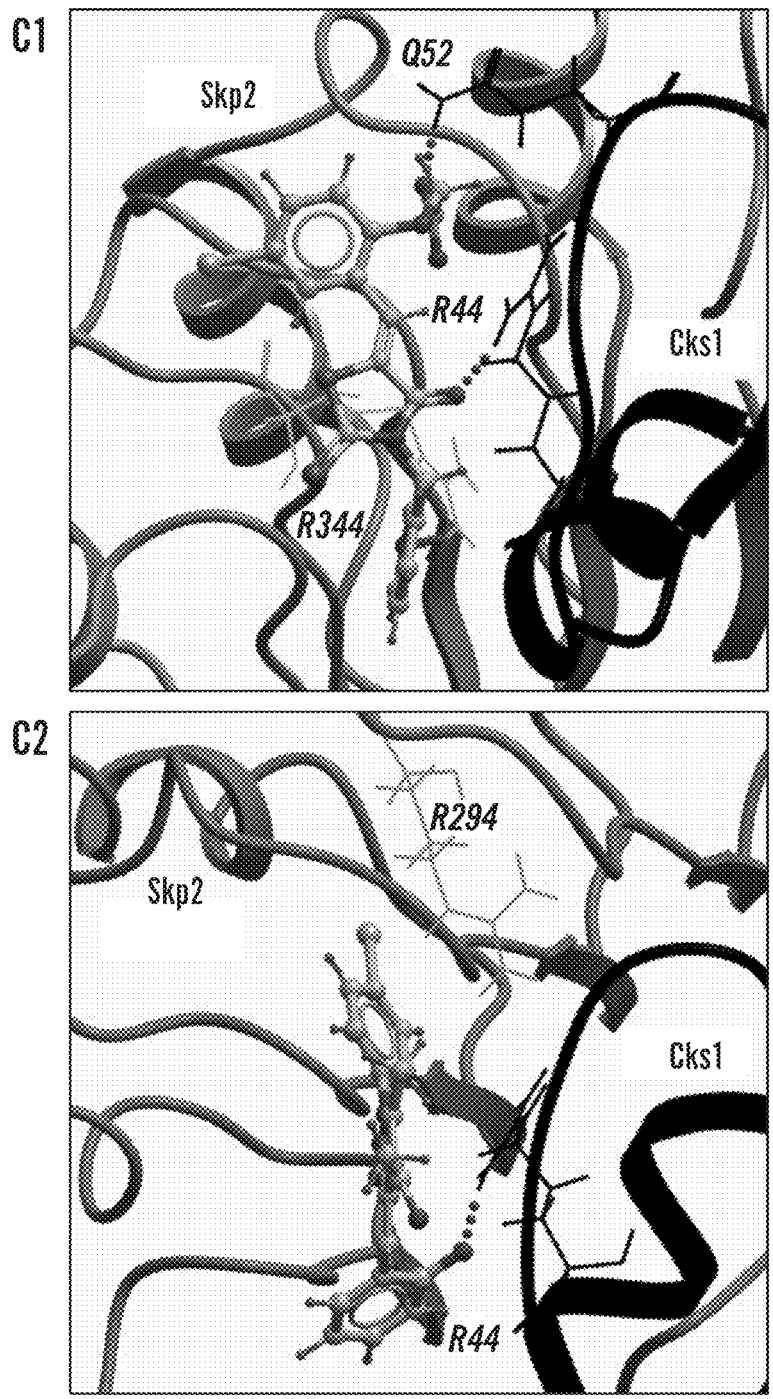
Figure 2C:
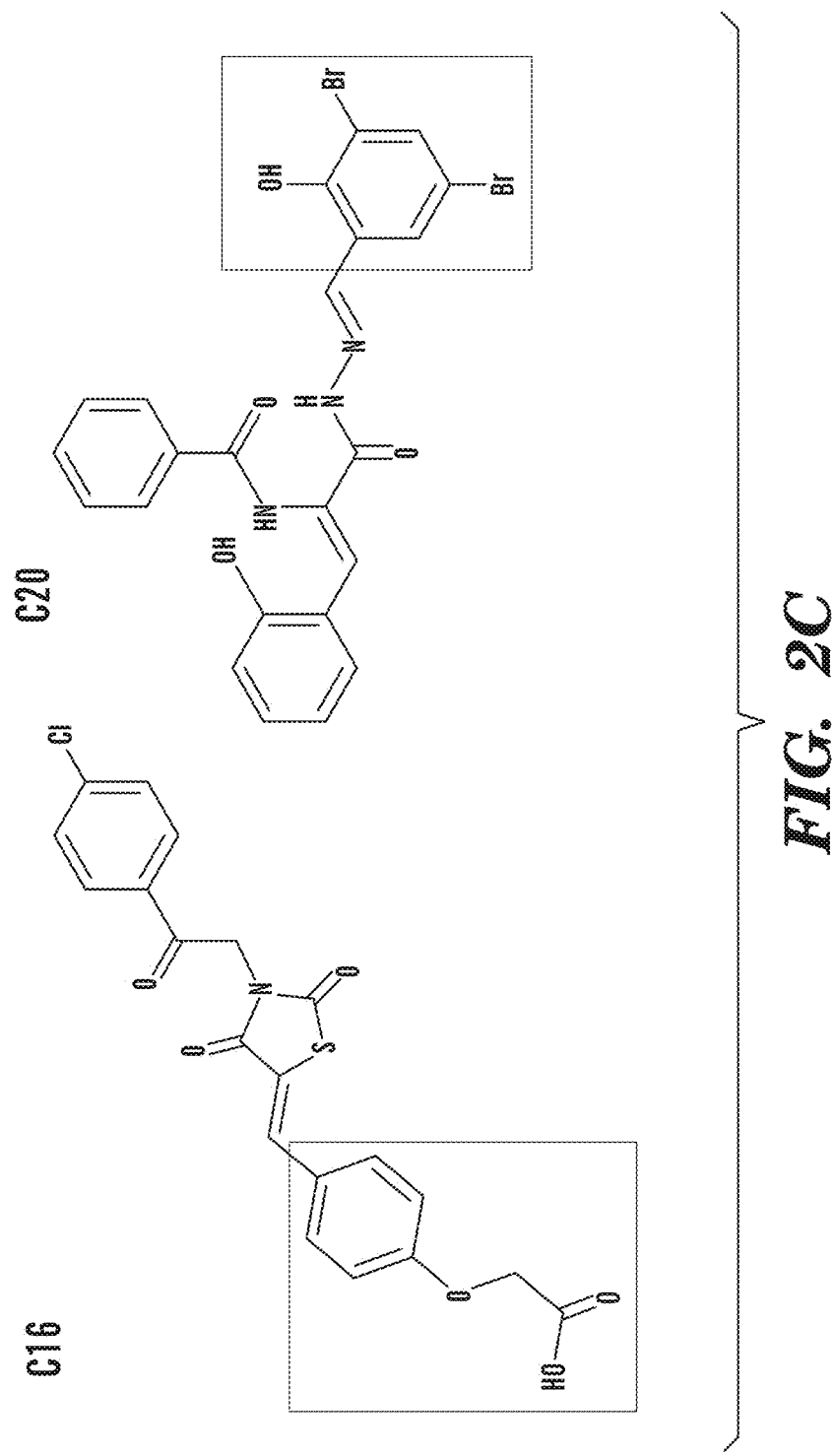
Figure 3A:
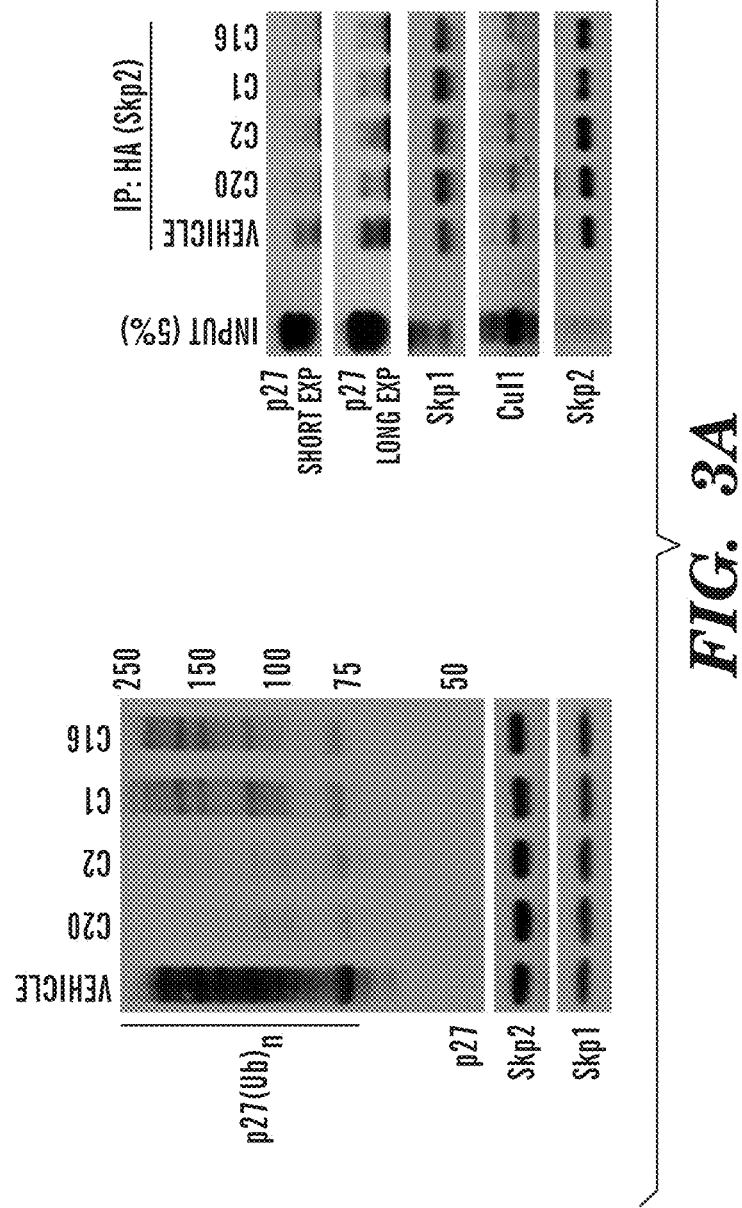

The docked poses predicted that the active compounds sterically clash with p27 (FIG. 2B and FIG. 7A). To test this model, immunoprecipitations for HA-Skp2 were performed from the in vitro ubiquitylation assay mix. The compounds (10 µM) exhibited various degrees of Skp2 ligase inhibition (FIG. 3A, left), which corresponded with a reduction of p27 binding to HA-Skp2 (FIG. 3A, right). The amount of Skp1 and Cul1 bound was not affected (FIG. 3A, right), confirming that the compounds were not disrupting SCF formation.

Figure 8C:
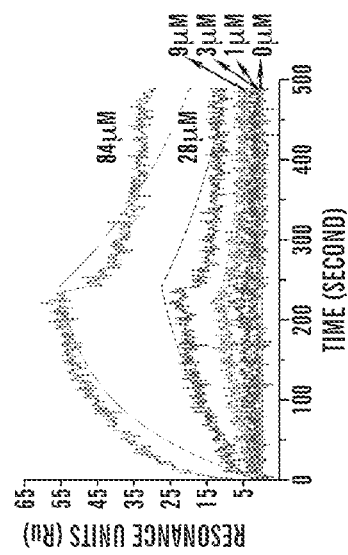

To test if the compounds are specifically targeting the Skp2-Cks1 interface, immunoprecipitations were performed in the absence of ubiquitylation. The amount of p27 bound to HA-Skp2 was reduced in the presence of the inhibitors, whereas Cks1 binding was unaffected (FIG. 3B). Knowing which chemical groups in C1 and C2 are necessary for inhibiting ubiquitylation (FIG. 2D, FIG. 8A), it was tested if the same groups are responsible for blocking p27 binding. Unmatched compounds for C1 (UM-C1) and C2 (UM-C2b) lost the ability to inhibit p27 from binding to Skp2 (FIG. 3C, lane 3 versus 4 and lane 5 versus 6). The same chemical contact was also important in mediating direct interaction with purified Skp2-Cks1 complex. Using differential scanning fluorimetry, C1 but not UM-C1 shifted the melting temperature of purified protein complex (FIG. 3D). Surface plasmon resonance assays also confirmed the ability of the compounds to bind Skp2-Cks1 complex (FIG. 8C). These data validate that the specific chemical groups identified from the VLS docking poses are mediating the compounds' interaction at the Skp2-Cks1 interface and blocking p27 binding.

Example 4

Induction of p27 by Inhibitors in Cancer Cells

Figures 4A, 4B:
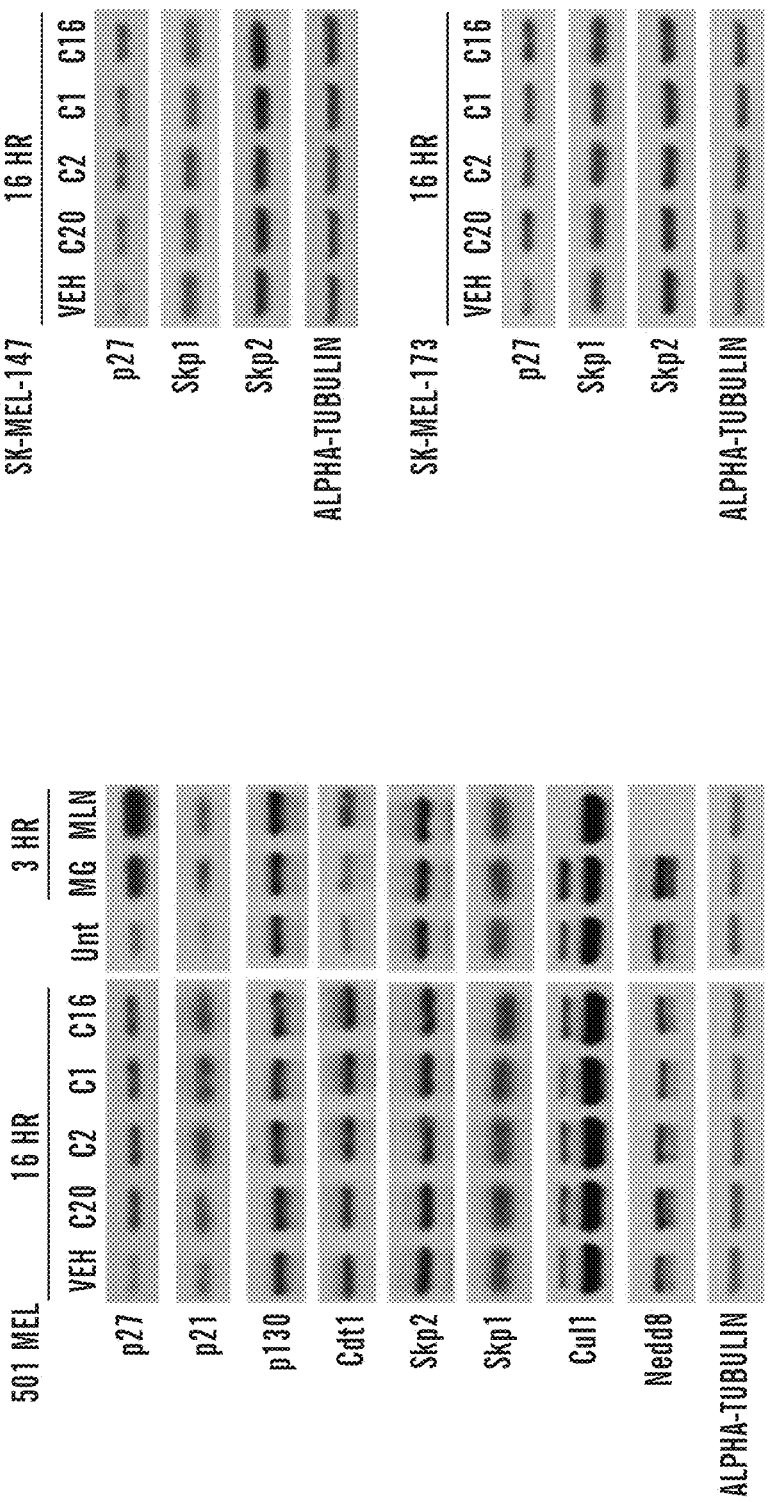
FIGS. 4A-D shows that inhibitors induce p27 protein in melanoma cells.

To test if these compounds prevented p27 degradation in cells, the metastatic melanoma cell lines 501 Mel, SK-MEL-147, and SK-MEL-173 were treated with each inhibitor (10 µM) or 0.1% DMSO (vehicle). Steady state protein levels of p27 were induced with inhibitors in a dose dependent manner (FIGS. 4A-B, FIG. 9A). p21 protein levels also increased, supporting p21 ubiquitylation by SCF-Skp2 is enhanced with Cks1 (Bornstein et al., "Role of the SCFSkp2 Ubiquitin Ligase in the Degradation of p21Cip1 in S Phase," *J. Biol. Chem.* 278:25752-25757 (2003), which is hereby incorporated by reference in their entirety) Inhibitor treatment did not alter protein levels of Skp2, Skp1, Cul1, and other Skp2 (Cks1-independent) targets p130, Cdt1, Tob1, and Cyclin E (FIG. 4A, left). 501 Mel cells were also treated with MG-132 (a proteasome inhibitor) to confirm that p27 and p21 induction were responsive to known UPS inhibitors (FIG. 4A, right). MLN-4924 inhibited neddylation of Cul1 (FIG. 4A, bottom 2 blots), an effect not mediated by the ligase inhibitors. Thus, treatment of cells with inhibitors targeting the Skp2-Cks1 interface induces protein levels of specific Skp2-Cks1 substrates.

Figure 4C:
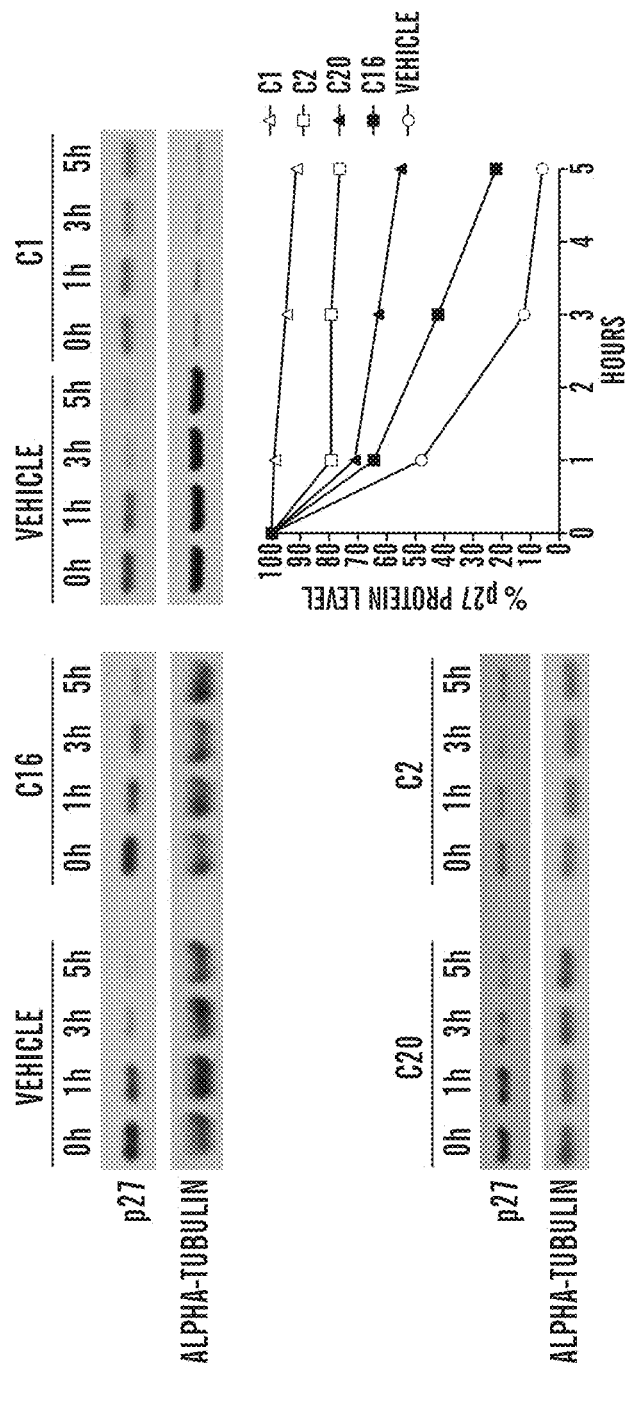

To assess the mechanism of p27 induction, cycloheximide half-lives were analyzed in 501 Mel cell lines pretreated with each inhibitor (10 µM) or 0.1% DMSO (vehicle). p27 degraded rapidly with a half-life of 1 hour with vehicle, and this rate was slowed by the inhibitors (FIG. 4C). C1 and C2 exhibited the strongest stabilization, with a p27 half-life greater than 5 hours, whereas C20 extended it to 5 hours and C16 extended it to 3 hours (FIG. 3C, graph). Protein levels of Skp2 and Skp1 remained constant.

Figure 4D:
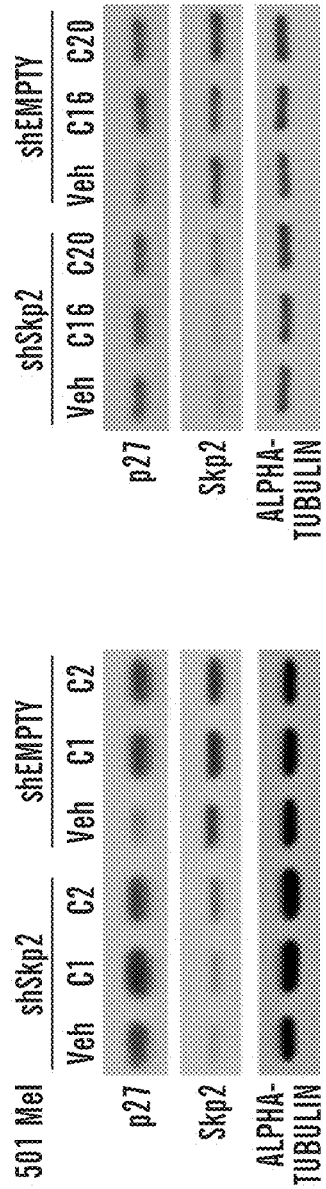

Since p27 has additional reported E3 ligases (Cao et al., "WW Domain-containing E3 Ubiquitin Protein Ligase 1 (WWP1) Delays Cellular Senescence By Promoting p27 (Kip1) Degradation in Human Diploid Fibroblasts," *J. Biol. Chem.* 286:33447-33456 (2011); Kamura et al., "Cytoplasmic Ubiquitin Ligase KPC Regulates Proteolysis of p27 (Kip1) at G1 Phase," *Nat. Cell Biol.* 6:1229-1235 (2004), which are hereby incorporated by reference in their entirety), the dependency of inhibitors for Skp2 using lentiviral tet-inducible short hairpins to Skp2 (shSkp2) was tested. Immunoblotting revealed that Skp2 knockdown eliminated inhibitor-mediated p27 induction (FIG. 4D, lane 1 versus 2, 3), whereas the 501 Mel cells expressing control shEmpty shRNA retained marked induction of p27 (FIG. 4D, lane 4 versus 5, 6). Compound induced p27 levels were similar to the basal level of p27 in the Skp2 knockdown cells (FIG. 4D, lane 1 versus 5, 6), suggesting that Skp2 is responsible for maintaining low levels of p27 in the 501 Mel cells. Taken together, the small molecules designed to the Skp2-Cks1 interface inhibited Skp2-dependent p27 degradation in metastatic melanoma cells.

Additional cancer cells were treated with C1, C2, and C20 to show the effect of inhibiting Skp2 ligase activity. Multiple myeloma (MM) cells are selective to killing by bortezomib (Chauhan et al., "Targeting the UPS as Therapy In Multiple Myeloma," *BMC Biochemistry* 9:S1 (2008), which is hereby incorporated by reference in its entirety). To test if direct inhibition of Skp2 ligase activity would also lead to lower viability, two different MM cell lines were treated with increasing concentrations of C1. Both cell lines exhibited low micromolar IC50 in response to C1 treatment, 1.84 μM in KSM-11 and 3.84 μM in ARP-1 (FIG. 10A). In mantle cell lymphoma, cell to cell contact leads to G1 arrest by down-regulating Skp2 and inducing p27 (Boss et al., "Cell Adhesion Induces p27Kip1-associated Cell-cycle Arrest Through Down-regulation of the SCFSkp2 Ubiquitin Ligase Pathway In Mantle-cell and Other Non-Hodgkin B-cell Lymphomas," *Neoplasia* 110:1631-1638 (2007), which is hereby incorporated by reference in its entirety). To address if antagonizing Skp2 ligase activity can directly reduce tumor viability, JeKo-1 mantle cell lines were treated with increasing doses of either C1 or C20 (FIG. 10B, top and middle graph). The calculated IC50 at 24 hours for C1 was 4.8 μM and for C2 was 9.3 μM (FIG. 10B, bottom chart), displaying cell type specific sensitivity to each compound. Estrogen induces Type 1 endometrial cancers by inducing proliferation via enhanced p27 degradation by SCF-Skp2 (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012), which is hereby incorporated by reference in its entirety). To address if direct inhibition of Skp2 ligase activity can restore p27 levels, ECC-1 cells (a human epithelial cell line derived from endometrium adenocarcinoma) was treated with increasing concentration of C2 and compared to Lactacystin treatment, a selective inhibitor of the proteasome. The protein levels of p27 were induced, with as low as 0.1 μM C2, to the same level as p27 induction mediated by the proteasome inhibitor (FIG. 10C). Thus, multiple human cancers that implicate Skp2-p27 axis in the pathogenesis of the disease are also responsive to treatment with Skp2 ligase inhibitors.

Example 5

Cell Cycle Effects of Inhibitor Treatment

Figure 5A:
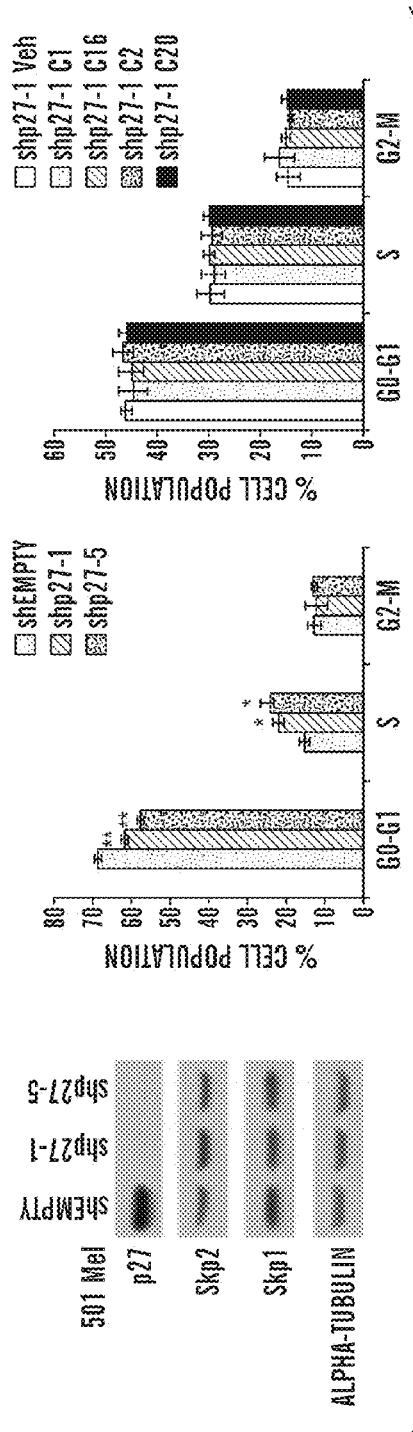
Figure 5B:
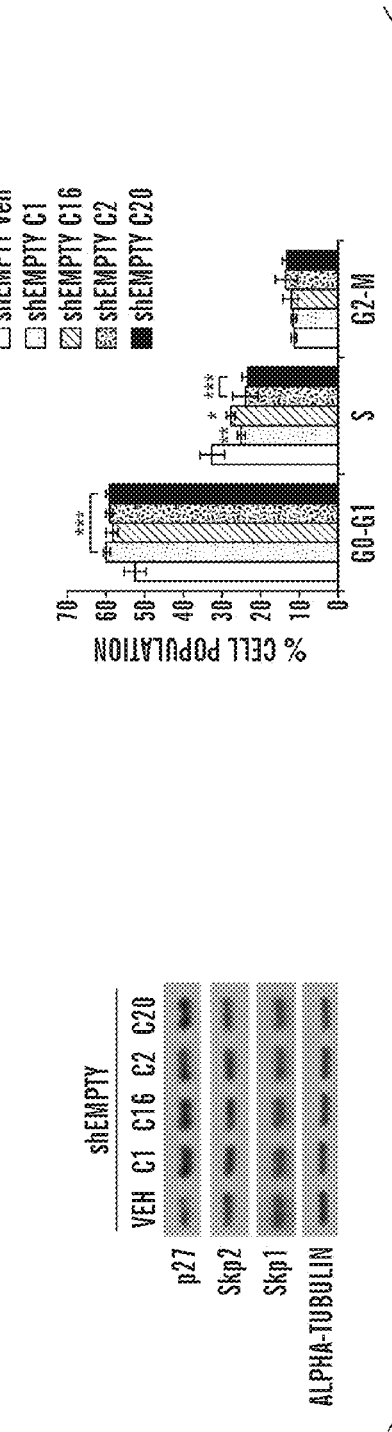
Figure 9A:
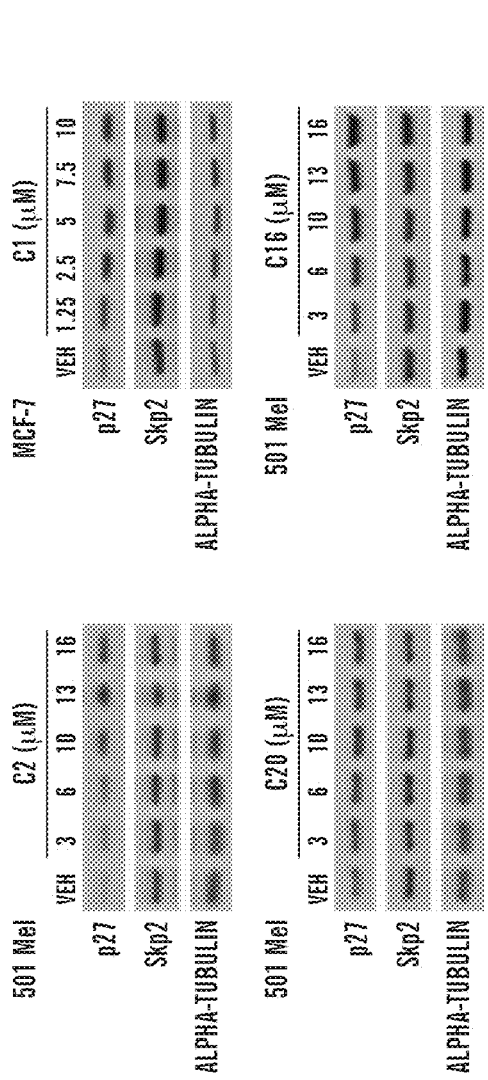
FIGS. 9A-B relate to dose response in metastatic melanoma and breast cancer cells.
Figure 9B:
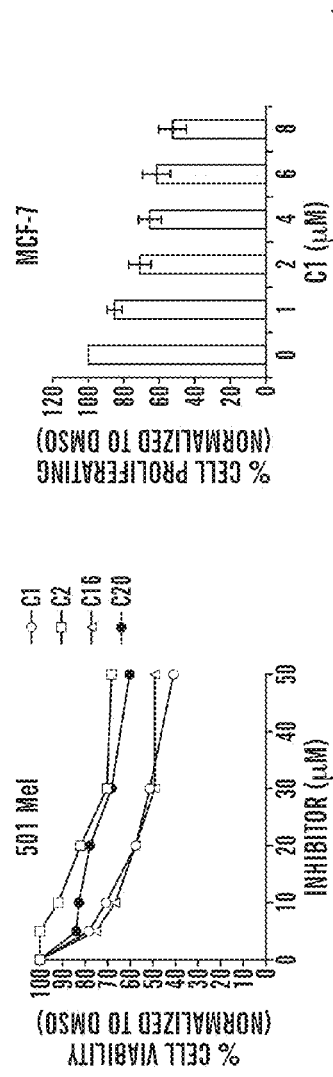

Skp2 siRNA treatment in melanoma cells resulted in p27 upregulation and reduced cell growth (Katagiri et al., "Knockdown of Skp2 by siRNA Inhibits Melanoma Cell Growth In Vitro and In Vivo," *J. Dermatol. Sci.* 42:215-224 (2006); Sumimoto et al., "Effective Inhibition of Cell Growth and Invasion of Melanoma By Combined Suppression of BRAF (V599E) and Skp2 with Lentiviral RNAi," *Int. J. Cancer* 118:472-476 (2006), which are hereby incorporated by reference in their entirety). 501 Mel cells responded to Skp2 ligase inhibitors by inducing p27 (FIGS. 4A-D, FIG. 9A), with a dose dependent effect on cell viability (FIG. 9B, left). To address the specific role of p27 in 501 Mel cell progression, p27 was knocked down using tet-inducible shRNA to p27 (shp27-1 or shp27-5) and compared to control empty vector shRNA (shEmpty). FACS analysis confirmed that the reduction of p27 protein levels (FIG. 5A, left) correlated with a significant decrease in G1 phase cells (p<0.001) and an increase in S phase cells (p<0.01) (FIG. 5A, middle). In the cells lacking p27, treatment with the inhibitors (10 μM for 16 hours) did not alter the cell cycle profile (FIG. 5A, right), suggesting that the inhibitors require p27 to elicit changes in cell cycle. To demonstrate this, shEmpty control cells were treated with the inhibitors (10 μM for 16 hours) and showed p27 protein induction (FIG. 5B, left) with a corresponding increase in G1 phase cells (p<0.001) and a decrease in S phase cells (p<0.01 for C1, p<0.05 for C16, p<0.0001 for C2 and C20) (FIG. 5B, right). Since inhibitor-mediated G1/S arrest is dependent on p27 and the inhibitors stabilize p27 protein in a Skp2-dependant manner (FIGS. 4A-D), the changes observed in the cell cycle most likely result from the inhibitors targeting Skp2 ligase activity.

In addition to melanomas, the Skp2-p27 axis regulates growth of breast and prostate cancer cells (Lu et al., "The F-box Protein SKP2 Mediates Androgen Control of p27 Stability in LNCaP Human Prostate Cancer Cells," *BMC Cell Biol.* 3:22 (2002); Shibahara et al., "Down-regulation of Skp2 is Correlated with p27-Associated Cell Cycle Arrest Induced by Phenylacetate in Human Prostate Cancer Cells," *Anticancer Res.* 25:1881-1888 (2005); Sun et al., "Knockdown of S-phase Kinase-associated Protein-2 Expression In MCF-7 Inhibits Cell Growth and Enhances the Cytotoxic Effects of Epirubicin," *Acta Biochim. Biophys. Sin.* (Shanghai) 39:999-1007 (2007), which are hereby incorporated by reference in their entirety). Breast cancer cell lines MCF-7 and T47D displayed no significant cellular phenotype after treatment with C2, C16, and C20. In contrast, treatment with C1 resulted in a lower rate of active cells (FIG. 9B, right), thus C1 treatment was reduced from 10 μM to 5 μM in order to monitor early cell cycle effects. T47D cells treated with C1 (5 μM for 16 hours) displayed an increase in G1 phase (p<0.0001) and a decrease in S phase (p<0.0001), correlating with p27 protein induction (FIG. 5C, left; FIG. 5E, center). In contrast, MCF-7 cells responded to C1 with a significant reduction in G1 phase (35%, p<0.0001) and an increase in G2-M phase (43%, p<0.0001) (FIG. 5C, left). This G1 reduction and G2/M arrest is dose dependent on C1 (FIG. 5C, right; p<0.001 and p<0.01, respectively) and correlates with increased p27 protein levels (FIG. 5E, left; FIG. 9A, top right). LNCaP prostate cancer cells treated with C2 (10 μM for 16 hours) displayed a mild, but significant, increase in G1 cells (p<0.0001) and a reduction in S phase cells (p<0.0001) (FIG. 5D), correlating with p27 protein induction (FIG. 5E, right). Therefore, multiple Skp2 ligase inhibitors induced p27 protein expression in a number of cancer cells, and this induction correlated with changes in cell cycle distribution. However, the cell cycle effects were dependent on cell type, with blocks at either the G1/S transition or the G2/M phase.

Example 6

Specific Small Molecule Inhibitors of Skp2-Mediated p27 Degradation

In silico high-throughput VLS was combined with low-throughput in vitro bioassays to identify the first set of small molecule inhibitors targeted to block Skp2-mediated p27 ubiquitylation and alter cell cycle progression. Multiple human cancers, including prostate, breast, ovarian, lung, and metastatic melanoma, express low levels of p27 and high Skp2 protein levels, with either protein status independently associated with poor prognosis and low patient survival (Chu et al., "The Cdk Inhibitor p27 in Human Cancer: Prognostic Potential and Relevance to Anticancer Therapy," *Nat. Rev. Cancer* 8:253-267 (2008); Florenes et al., "Protein Expression of the Cell-cycle Inhibitor p27Kip1 in Malignant Melanoma: Inverse Correlation with Disease-free Survival," *Am. J.*

Pathol. 153:305-312 (1998); Hershko, "Oncogenic Properties and Prognostic Implications of the Ubiquitin Ligase Skp2 In Cancer," Cancer 112:1415-1424 (2008); Li et al., "Skp2 and p27kip1 Expression In Melanocytic Nevi and Melanoma: An Inverse Relationship," J. Cutan. Pathol. 31:633-642 (2004); Woenckhaus et al., "Expression of Skp2 and p27KIP1 In Naevi and Malignant Melanoma of the Skin and Its Relation to Clinical Outcome," Histol. Histopathol. 20:501-508 (2005), which are hereby incorporated by reference in their entirety). Thus, the Skp2-p27 axis is an attractive target for drug discovery, and cancers that rely on Skp2 ligase activity for their oncogenic properties should be highly susceptible to specific and direct inhibitors of Skp2-mediated p27 ubiquitylation.

One major challenge was that the target site was a protein-protein interface. It was previously proposed that certain protein-protein interfaces may be targeted for drug discovery if they exhibited favorable configurations, including the presence of a drug-binding pocket of sufficient size located at a functionally sensitive location on the interface (Cardozo et al., "Druggability of SCF Ubiquitin Ligase-protein Interfaces," Methods Enzymol. 399:634-653 (2005), which is hereby incorporated by reference in their entirety). In order to target such surfaces, pocket specific screening approaches, as opposed to high-throughput screening (HTS), must be utilized, of which VLS is perhaps the most suitable. In this study, this theory was successfully put into practice. Furthermore, this study extended the theory by suggesting that pockets formed by the association of two proteins, in this case Skp2 and Cks1, are no different from mono-domain pockets and can be equally targeted with success.

A second major challenge was to confirm the primary target of the inhibitors, given that previous attempts identified compounds that either blocked Skp2 incorporation into an active SCF or reduced Skp2 mRNA levels (Chen et al., "Targeting the p27 E3 Ligase SCF(Skp2) Results in p27- and Skp2-mediated Cell-cycle Arrest and Activation of Autophagy," Blood 111:4690-4699 (2008); Rico-Bautista et al., "Chemical Genetics Approach to Restoring p27Kip1 Reveals Novel Compounds with Antiproliferative Activity In Prostate Cancer Cells," BMC Biol. 8:153 (2010), which are hereby incorporated by reference in their entirety). Since the in silico screen selected small molecules that were highly structurally compatible with the Skp2-Cks1 protein interface, there is a high likelihood that validated compounds would not nonspecifically inhibit any of the multiple proteins/enzymes present in the ubiquitylation process. This included sites small molecules were shown to inhibit: (1) the F-box domain interface with Skp1, (2) CyclinE/Cdk2 kinase activity, (3) E2 Ubc3 (Cdc34) activity, and (4) a known druggable protein interface MDM2-p53 (Aghajan et al., "Chemical Genetics Screen for Enhancers of Rapamycin Identifies a Specific Inhibitor of an SCF Family E3 Ubiquitin Ligase," Nat. Biotechnol. 28:738-742 (2010); Ceccarelli et al., "An Allosteric Inhibitor of the Human Cdc34 Ubiquitin-conjugating Enzyme," Cell 145:1075-1087 (2012); Meijer et al., "Biochemical and Cellular Effects of Roscovitine, a Potent and Selective Inhibitor of the Cyclin-dependent Kinases cdc2, cdk2 and cdk5," Eur. J. Biochem. 243:527-536 (1997); Millard et al., "Small-molecule Inhibitors of p53-MDM2 Interaction: The 2006-2010 Update," Curr. Pharm. Des. 17:536-559 (2011), which are hereby incorporated by reference in their entirety). The compounds described herein do not exhibit activity against any of these off-targets, showing high selectivity for SCF-Skp2 ligase.

One major advantage of the approach described herein is that the predicted VLS docking poses highlight key chemical groups that can be used as a chemical fingerprint to identify additional Skp2 ligase inhibitors. Interrogating receptor-ligand atomic contacts and using chemical similarity searches identified more diverse and/or potent inhibitors (Cheltsov et al., "Vaccinia Virus Virulence Factor N1L Is a Novel Promising Target for Antiviral Therapeutic Intervention," J. Med. Chem. 53:3899-3906 (2010); Wang et al., "Skp2 Is Required for Survival of Aberrantly Proliferating Rb1-deficient Cells and for Tumorigenesis In Rb1+/−Mice," Nat. Genet. 42:83-88 (2009), which are hereby incorporated by reference in their entirety). Thus, a blueprint or pharmacophore of the entire Skp2 ligase inhibitor class is preliminarily visualized, which may guide the rational synthesis of derivatives of C1, C2, C16, and C20 during preclinical lead optimization stages. Using thermal shifts and SPR technologies, the compounds display specific binding to the Skp2-Cks1 protein complex, but the co-crystal structures of Skp1-Skp2-Cks1 have not been obtained in complex with the inhibitors, possibly due to stringent crystallization conditions. Nevertheless, the compendium of data on these inhibitors leaves little doubt that they act at the targeted pocket formed by Skp2-Cks1. The clear visualization of their pharmacophore also leaves little doubt that chemically diverse, more potent and soluble compounds derived from this pharmacophore will be resolved crystallographically.

By targeting the Skp2-Cks1-p27 interface, the focus was on inhibiting cell cycle progression (Bloom et al., "Deregulated Degradation of the Cdk Inhibitor p27 and Malignant Transformation," Semin. Cancer Biol. 13:41-47 (2003), which is hereby incorporated by reference in their entirety). Inhibitor-treated metastatic melanoma cells displayed a significant shift of cells from S phase into G1 phase that was dependent on both p27 and Skp2, validating the inhibitors are regulating p27 levels to elicit cellular changes. Interestingly, C1 treatment of MCF-7 breast cancer cells lines did not increase, but rather decreased the percentage of cells in G1 while increasing the G2/M population. This same G2/M phenotype has been observed in Skp2−/− MEFs and was reversed by knocking out p27, suggesting that p27 also plays a pivotal role in G2/M phase (Nakayama et al., "Skp2-mediated Degradation of p27 Regulates Progression into Mitosis," Dev. Cell 6:661-672 (2004); Pagano, "Control of DNA Synthesis and Mitosis By the Skp2-p27-Cdk1/2 Axis," Mol. Cell 14:414-416 (2004), which are hereby incorporated by reference in their entirety). Elucidation of the specific mechanism may now be interrogated in MCF-7 cells that are especially sensitive to C1 mediated G2/M accumulation. This type of chemical genetic approach would not be possible without the availability of inhibitors specifically blocking Skp2 mediated p27 degradation.

In this study, the principle that Skp2 ligase activity is susceptible to inhibition by small molecules was proved. UPS inhibitor research has accelerated since the FDA approval of Bortezomib, and the focus has been on the additional enzymes present in this pathway. The approach described herein demonstrates that a non-enzymatic protein-substrate interface is druggable with a high degree of selectivity. This added level of specificity may prove indispensable when evaluating combinatorial therapies between inhibitors of the UPS and conventional chemotherapies (Ning et al., "Liposomal Doxorubicin In Combination with Bortezomib for Relapsed or Refractory Multiple Myeloma," Oncology (Williston Park) 21:1503-1508; discussion 1511, 1513, 1516 passim (2007); Wright, "Combination Therapy of Bortezomib with Novel Targeted Agents: An Emerging Treatment Strategy," Clin. Cancer Res. 16:4094-4104 (2010), which are hereby incorporated by reference in their entirety). These pharmacological inhibitors may also aid in identifying and treating cancers that rely on the Skp2 ligase activity for their oncogenic properties.

Example 7

Experimental Procedures

In Silico Assays

The in silico protein receptor and ligand preparations, the docking simulations during VLS, and the docking score calculations as well as chemical similarity and substructure searches were carried out with ICM-Pro, ICM-VLS and ICM-Chemistry software (Molsoft LLC, La Jolla, Calif.) (Abagyan et al., "ICM—A New Method for Protein Modeling and Design: Applications to Docking and Structure Prediction from the Distorted Native Conformation," *Journal of Computational Chemistry* 15:488-506 (1994), which is hereby incorporated by reference in its entirety). Pockets on the crystallographic structure PDB 2ast were identified with the ICM PocketFinder module in ICM-Pro and screened by ICM-VLS against the ChemBridge Library (ChemBridge Corp, San Diego, Calif.) using default ICM-VLS docking parameters. Dockings used global optimization with a biased probability Monte Carlo (BPMC) conformational search of fully flexible, full-atom models of the ligands within a set of grid potential maps calculated from the coordinates of the atoms in the protein receptor (Abagyan et al., "Biased Probability Monte Carlo Conformational Searches and Electrostatic Calculations for Peptides and Proteins," *J. Mol. Biol.* 235:983-1002 (1994); Abagyan et al., "High-throughput Docking for Lead Generation," *Curr. Opin. Chem. Biol.* 5:375-382 (2001), which are hereby incorporated by reference in their entirety). These grid energy maps account for the hydrophobic, heavy atom and hydrogen van der Waals interactions, hydrogen-bonding interactions, and electrostatic potential. Hits with VLS docking score better than −30U were further filtered by Lipinski's rules to eliminate non-drug-like compounds. Substructure search was performed using the ChemBridge and ICM MolCart databases, with Tanimoto distance as a measure of chemical similarity.

Plasmids

HA-Skp2, Cks1, Q52L-Cks1, p27, Flag-Beta-TrCP, and HA-PDCD4 cloned into pcDNA3.1 plasmids were provided by Dr. Michele Pagano (NYUMC). Short hairpins for p27 (cat. no. RHS4740-NM_004064) and Skp2 (cat. no. RHS4740-NM_005983) in doxycycline-regulated TRIPZ lentiviral vector were obtained from Open Biosystems and prepared following manufacturer instructions.

pcDNA3.1 HA-Skp2 and Cks1 was used as template to generate Skp2-R294A, -R344A, and Cks1-R44A/H with the QuickChange site-directed mutagenesis (Strategene) kit following manufacturer's instruction.

Antibodies and Immunoblotting

Antibodies include mouse monoclonal antisera against Skp2/p45 (Invitrogen), p27 (BD Biosciences), Cks1 (Invitrogen), Cyclin E (Invitrogen), alpha-tubulin (Sigma), and HA (Covance); and rabbit polyclonal antisera against phospho-Thr-187 p27 (Invitrogen), total p27 (Cell Signaling), p21 (Cell Signaling), Skp1 (Invitrogen), NEDD8 (Cell Signaling), Cul1 (Invitrogen), p130 (Santa Cruz), Cdt1 (Cell Signaling), His (Santa Cruz), HA (Invitrogen), and β-TrCP (Invitrogen).

Ubiquitylation Assays

In vitro reconstituted assays were performed as previously described (Dorrello et al., "S6K1- and betaTRCP-mediated Degradation of PDCD4 Promotes Protein Translation and Cell Growth," *Science* 314:467-471 (2006), which is hereby incorporated by reference in their entirety) with the exceptions of the use of (1) unlabeled proteins (wild-type and mutant Skp2 and Cks1, p27, Flag-βTrCP, and HA-PDCD4) generated by in vitro transcription-translation (TNT T7 Coupled Reticulocyte Lysate System, Promega); (2) chain elongation with non-methylated ubiquitin; and (3) immunoblotting to detect poly-ubiquitylation. The following reagents were obtained from Boston Biochem: UBE1, His-UbcH3, His-UbcH5c, Ubiquitin, and Ubiquitin Aldehyde. Additional reagents include CDK2/CyclinE1 (Sigma-Aldrich), S6K (Invitrogen), Okadaic acid (Sigma), and DMSO (Sigma-Aldrich). For ubiquitin charging, UBE1 (100 nM) and His-UbcH3 (10 ng/μl) were incubated with ubiquitin (2.5 μg/μl), ATP (2 mM), and 10 μM □ of inhibitors or Vehicle control for 60 min at 30° C. Reactions were stopped in nondenaturing 2× Sample Buffer, with the addition of 10% Beta-mercaptoethanol as indicated, and analyzed by Western blotting.

p53 ubiquitylation was carried out with the p53 Ubiquitylation Kit (Boston Biochem) following manufacturers protocol. Immunoblotting was performed using mouse monoclonal p53 (Santa Cruz) and rabbit polyclonal MDM2 (Santa Cruz).

Inhibitors

Control ubiquitylation inhibitors were Roscovitine (Cayman Chemicals), MG132 (Peptide Institute), and MLN-4924 (Active Biochem), and Lactacystin (Calbiochem). Compounds obtained from ChemBridge Corp. (San Diego, Calif., USA) include C1 (6719837), C2 (6544607), and C16 (6744881). C20 (A067/0031209) was obtained from Ryan Scientific, Inc (Mount Pleasant, S.C., USA).

The following unmatch (UM-) and negative (Neg-) compounds were ordered from ChemBridge Corp (San Diego, Calif., USA): UM-C1 (6747962), Neg-C1b (6781919), UMC2a (5666975), UM-C2b (5953374), Neg-3 (6701160), Neg-4a (6337451), Neg-4b (6319889), Neg-5 (5275605). UM-C20 was obtained from Sigma-Aldrich (cat # R954926).

Binding and Kinase Assays

In vitro ubiquitylation assays were incubated with anti-HA affinity matrix (Roche) in IP buffer (50 mM Tris pH 7.6, 150 mM NaCl, 0.1% NP40, and Roche Complete EDTA-free protease tablet) for 16 h at 4° C. Beads were washed 3× with IP buffer and eluted with 2×SDS Sample Buffer (Boston Bioproducts) and 10% Beta-mercaptoethanol. For binding without ubiquitylation, HA-Skp2 IVT (10 μl) and Cks1 IVT (10 μl) were preincubated with anti-HA affinity matrix in IP buffer for 2 hours, with the addition of p27 kinase reaction (10 μl) for another 16 h incubation at 4° C. All reactions were analyzed after SDS/PAGE by western blotting. Where indicated, Skp2 and Cks1 were pretreated with 10 μM inhibitors for 30 minutes. Kinase reactions were performed with p27 IVT (10 μl) and 0.5 μg/ul CyclinE/CDK2 in kinase buffer (50 mM Tris HCL pH 7.5, 10 mM $MgCl_2$, 2 mM ATP, 2.5 μM Okadaic Acid, and 0.6 mM DTT) at 30° C. for 1 h.

Differential Scanning Fluorimetry

Protein melt assays were carried out following the manufacturer's protocol on the LightCycler 480 System II (Roche) using Sypro Orange dye (Sigma). Fluorescence (465 nm excitation/580 nm detection) was acquired (10 data points/sec) at a ramp rate of 0.06° C./sec between 20° C. and 85° C. Melting temperatures were calculated using the LightCycler 480 Protein Melt analysis tool (Roche).

Surface Plasmon Resonance (SPR) Analysis

The ProteOn XPR36 protein interaction array system (Bio-Rad, Hercules, Calif.) was used to measure the binding affinity of the compounds to the Skp1-Skp2-Cks1 complex. His6-tagged human Skp2 (residues 89-424) and truncated Skp1

(Schulman et al., "Insights Into SCF ubiquitin Ligases from the Structure of the Skp1-Skp2 Complex," *Nature* 408:381-386 (2000), which is hereby incorporated by reference in its entirety) were coexpressed and purified as described (Hao et al., "Structural Basis of the Cks1-dependent Recognition of p27(Kip1) By the SCF(Skp2) Ubiquitin Ligase," *Mol. Cell* 20:9-19 (2005), which is hereby incorporated by reference in its entirety). Human full-length Cks1 was produced as described (Hao et al., "Structural Basis of the Cks1-dependent Recognition of p27(Kip1) By the SCF(Skp2) Ubiquitin Ligase," *Mol. Cell* 20:9-19 (2005), which is hereby incorporated by reference in its entirety). The His6-Skp2-Skp1-Cks1 complex was prepared by mixing the Skp2-Skp1 complex with Cks1 in a 1:1.5 molar ratio, followed by gel filtration chromatography purification. The purified His6-Skp2-Skp1-Cks1 complex was coupled to two ligand channels in a HTE sensor chip based on histidine-NTA affinity interaction, with final immobilization levels of ~4,000 resonance units. Reference channel was prepared in parallel following the same activation and immobilization procedure but without the injection of the complex. After 90° rotation of the fluid system, each compound was injected simultaneously at five different concentrations over the immobilized proteins at a flow-rate of 30 µl/min for 4 min in buffer containing 10 mM Tris (pH 8.0), 200 mM NaCl, 10 mM imidazole, and 0.05% Tween 20 (v/v). The dissociation phase involved the injection of buffer alone for additional 3 minutes. All the experiments were performed at 25° C. The compound-dependent signals were processed by double referencing, subtracting the response observed on surfaces immobilizing the complex alone and the signal observed injecting the buffer alone. The resulting sensorgrams were fitted by the simplest 1:1 interaction model (Proteon analysis software).

Cell Lines and Knockdown

MCF-7, T47D, JeKo-1, and ECC-1[EnCA1] were purchased from ATCC and cultured as specified. 501 Mel, SK-MEL-147, and SK-MEL-173 were kindly provided by Dr. Eva Hernando of NYUMC. LNCaP were a kind gift from Dr. Michael Garabedian (NYUMC). KSM-11 and ARP-1 cell were kindly provided by Dr. Seth Orlow (NYUMC). 501 Mel were cultured in OPTI-MEM reduced serum supplemented with 5% FBS and 1% pen-strep. SK-MEL lines, KSM-11, ARP-1, and LNCaP were cultured in DMEM supplemented with 10% FBS and 1% pen-strep. All cell culture reagents were obtained from GIBCO, except Tet System approved Fetal Bovine Serum (#631101) and doxycycline (#631311), which were supplied by Clontech. For knockdown, 501 Mel cells were infected with TRIPZ p27, Skp2, or empty vector and treated for 3 days with 2 ng/ml doxycycline. Cells expressing more than 70% RFP were used for further analysis. From the p27 shRNA set, knockdown was achieved with V3THS_410220 (shp27-1) and V3THS_372105 (shp27-5). From the Skp2 shRNA set, knockdown was achieved with V2THS_254607 (shSkp2).

Cell Based Analysis

Whole cell extracts were prepared and immunoblotted as previously described Dorrello et al., "S6K1- and betaTRCP-mediated Degradation of PDCD4 Promotes Protein Translation and Cell Growth," *Science* 314:467-471 (2006), which is hereby incorporated by reference in its entirety. For knockdown of Skp2 or p27, shRNAs were induced with 2 ng/ml doxycycline for 48 hours, with the last 16 hours co-treated with 0.1% Vehicle or 10 µM inhibitors as indicated. For cycloheximide chase, cells were pretreated 16 h with 0.1% Vehicle or 10 µM inhibitors, followed by 20 ng/ml cycloheximide (Sigma) and whole cell extracts collected for each time point. 20 ng/ml cycloheximide (Sigma) was added to each plate and whole cell extract was collected for each time point. Scanning densitometry was performed on immunoblots using Image J software. For cell cycle analysis, cells were treated with 0.1% Vehicle or 10 µM inhibitors for 16 h. 1×10$^6$ cells were fixed in 70% ethanol for 2 h, treated with 200 µg/ml RNase A (Invitrogen) for 30 minutes, and stained with 20 µg/ml Propidium Iodine (Sigma). All samples were assayed in triplicates. Signal was detected using the Becton Dickson LSRII flow cytometer and cell cycle profiles were analyzed with FloJo.

Viable and metabolically active cells were assayed using CellTiter-Blue (Promega) or PrestoBlue (Invitrogen) following manufacturer's instruction. In a 96 well plate format, 15×10$^3$ cells were pretreated with 0.1% Vehicle or increasing concentration of inhibitors as noted (for 16 h, 24 h, 48 h, and/or 72 hr) and fluorescence was detected on the SpectraMax M2e (Molecular Devices) after 30 min incubation with dye.

Statistical Methodologies

Statistical significance between and among groups was determined by Student's paired two-tailed t test or One-way ANOVA, using Dunnett's multiple comparison test as the post hoc analysis. $p<0.05$ was considered significant. (GraphPad Prism Software).

Example 8

Inhibitors of SCF-Skp2/Cks1 E3 Ligase Stabilize Nuclear p27$^{kip1}$ for Growth Regulation in Human Endometrial Carcinoma Introduction An early event in carcinogenesis is loss of growth regulation. The cyclin-dependent kinase (Cdk) inhibitor, p27$^{kip1}$ (p27) inhibits cell proliferation by arresting cells in late G1 phase of the cell cycle by specifically blocking CyclinE/Cdk2 activity (Chu et al., "The Cdk Inhibitor p27 in Human Cancer: Prognostic Potential and Relevance to Anticancer Therapy," *Nat. Rev. Cancer,* 8:253-267 (2008) and Sherr et al., "CDK Inhibitors: Positive and Negative Regulators of G1-phase Progression," *Genes Dev.* 13:1501-1512 (1999), which are hereby incorporated by reference in their entirety. The importance of p27 binding to Cdk2 for its tumor suppressive function was shown by the development of tumors of multiple organs in mice p27 knock-in studies in which Cdk2 regulatory domain of p27 was deleted (Besson et al., "Discovery of an Oncogenic Activity in p27Kip1 that Causes Stem Cell Expansion and a Multiple Tumor Phenotype," *Genes Dev.* 21:1731-1746 (2007), which is hereby incorporated by reference in its entirety. The tumor suppressor function of p27 can switch to being oncogenic either by its loss from the nucleus via ubiquitin mediated degradation or by mislocalization to the cytoplasm (Chu et al., "The Cdk Inhibitor p27 in Human Cancer: Prognostic Potential and Relevance to Anticancer Therapy," *Nat. Rev. Cancer,* 8:253-267 (2008); Wander et al., "p27: A Barometer of Signaling Deregulation and Potential Predictor of Response to Targeted Therapies," *Clin. Cancer Res.* 17:12-18 (2011); Serres et al., "Cytoplasmic p27 is Oncogenic and Cooperates with Ras both In Vivo and In Vitro," *Oncogene* 30:2846-2858 (2011), which are hereby incorporated by reference in their entirety) where p27 represses RhoA signaling thereby affecting cytoskeletal organization, cell migration, and tumor metastasis (Chu et al., "The Cdk Inhibitor p27 in Human Cancer: Prognostic Potential and Relevance to Anticancer Therapy," *Nat. Rev. Cancer,* 8:253-267 (2008); Denicourt et al., "Relocalized p27Kip1 Tumor Suppressor Functions as a Cytoplasmic Metastatic Oncogene in Melanoma," *Cancer Res.* 67:9238-9243 (2007); Larrea et al., "Jekyll and Hyde: Regulation of Cell Cycle and Cell Motility," *Cell Cycle* 8:3455-3461 (2009), which are hereby incorporated by reference in their entirety). Phosphorylation of p27 on specific amino acids by different kinases controls the fate of p27 (Chu et al., "The Cdk Inhibitor p27 in Human Cancer: Prognostic Potential and Relevance to Anticancer Therapy," *Nat. Rev. Cancer*, 8:253-267 (2008), which is hereby incorporated by reference in its entirety) and, accordingly, high kinase activity associated with malignant cellular behavior obviates the anti-proliferative effect of p27 (Chu et al., "p27 Phosphorylation by Src Regulates Inhibition of Cyclin E-Cdk2," Cell 128:281-294 (2007); Kelly-Spratt et al., "Inhibition of PI-3K Restores Nuclear p27Kip1 Expression In a Mouse Model of Kras-driven Lung Cancer," *Oncogene* 28:3652-3662 (2009); Chen et al., "Combined Src and ER Blockade Impairs Human Breast Cancer Proliferation In Vitro and In Vivo," *Breast Cancer Res. Treat.* 128:69-78 (2011), which are hereby incorporated by reference in their entirety. Phosphorylation on Thr187 by CyclinE/Cdk2 or MAPK is required for p27 ubiquitylation in the nucleus by the E3 ligase complex SCF-Skp2/Cks1, which targets p27 for subsequent proteasomal degradation (Lecanda et al., "Transforming Growth Factor-beta, Estrogen, and Progesterone Converge on the Regulation of p27Kip1 in the Normal and Malignant Endometrium," *Cancer Res.* 67:1007-1018 (2007); Bloom & Pagano, "Deregulated Degradation of the Cdk Inhibitor p27 and Malignant Transformation," *Semin. Cancer Biol.* 13:41-47 (2003); Huang et al., "Estrogen and Progesterone Regulate p27kip1 Levels Via the Ubiquitin-proteasome System: Pathogenic and Therapeutic Implications for Endometrial Cancer," *PLoS One* 7:e46072 (2012), which are hereby incorporated by reference in their entirety). Phosphorylation on Ser10 by KIS facilitates p27 binding to CRM-1 for nuclear export (Ishida et al., "Phosphorylation of p27Kip1 on Serine 10 is Required for Its Binding to CRM1 and Nuclear Export," *J. Biol. Chem.* 277:14355-14358 (2002), which is hereby incorporated by reference in its entirety) and PI3K/Akt-dependent phosphorylation of p27 on T157 and T198 prevents nuclear re-entry (Kelly-Spratt et al., "Inhibition of PI-3K Restores Nuclear p27Kip1 Expression in a Mouse Model of Kras-driven Lung Cancer," *Oncogene* 28:3652-3662 (2009); Shin et al., "Phosphorylation of p27Kip1 at Thr-157 Interferes with Its Association with Importin Alpha During G1 and Prevents Nuclear Re-entry," *J. Biol. Chem.* 280:6055-6063 (2005); Wen et al., "Promotion of Cytoplasmic Mislocalization of p27 by *Helicobacter pylori* in Gastric Cancer," *Oncogene* 31:1771-1780 (2012), which are hereby incorporated by reference in their entirety). Whereas both low levels or loss of nuclear p27 and/or cytoplasmic mislocalization can serve as prognostic indicators of poor outcome in numerous human malignancies (Chu et al., "The Cdk Inhibitor p27 in Human Cancer: Prognostic Potential and Relevance to Anticancer Therapy," *Nat. Rev. Cancer*, 8:253-267 (2008) and Wen et al., "Promotion of Cytoplasmic Mislocalization of p27 by *Helicobacter pylori* in Gastric Cancer," *Oncogene* 31:1771-1780 (2012), which are hereby incorporated by reference in their entirety), cytoplasmic expression particularly carries a poor prognosis in certain cancers including of breast, prostate, and kidney (Chu et al., "The Cdk Inhibitor p27 in Human Cancer: Prognostic Potential and Relevance to Anticancer Therapy," *Nat. Rev. Cancer*, 8:253-267 (2008); Wen et al., "Promotion of Cytoplasmic Mislocalization of p27 by *Helicobacter pylori* in Gastric Cancer," *Oncogene* 31:1771-1780 (2012); Liang et al., "PKB/Akt Phosphorylates p27, Impairs Nuclear Import of p27 and Opposes p27-mediated G1 Arrest," *Nat. Med.* 8:1153-1160 (2002); Kruck et al., "High Cytoplasmic Expression of p27 (Kip1) is Associated with a Worse Cancer-specific Survival in Clear Cell Renal Cell Carcinoma," *BJU Int.* 109:1565-1570 (2012); Duncan et al., "Cytoplasmic p27 Expression is an Independent Prognostic Factor in Ovarian Cancer," *Int. J. Gynecol. Pathol.* 29:8-18 (2010); Hidaka et al., "The Combination of Low Cytoplasmic and High Nuclear Expression of p27 Predicts a Better Prognosis in High-grade Astrocytoma," *Anticancer Res.* 29:597-603 (2009), which are hereby incorporated by reference in their entirety). Interestingly, *H. pylori* infection, which predisposes to gastric cancer was shown to promote cytoplasmic mislocalization of p27 through PI3K/Akt signaling as a potential mechanism of gastric carcinogenesis (Wen et al., "Promotion of Cytoplasmic Mislocalization of p27 by *Helicobacter pylori* in Gastric Cancer," *Oncogene* 31:1771-1780 (2012), which is hereby incorporated by reference in its entirety). In addition, restoration of nuclear p27 expression can predict response to chemotherapy in colon and lung cancers (Wander et al., "p27: A Barometer of Signaling Deregulation and Potential Predictor of Response to Targeted Therapies," *Clin. Cancer Res.* 17:12-18 (2011); Kelly-Spratt et al., "Inhibition of PI-3K Restores Nuclear p27Kip1 Expression In a Mouse Model of Kras-driven Lung Cancer," *Oncogene* 28:3652-3662 (2009), which are hereby incorporated by reference in their entirety).

Previously, it has been shown that loss of nuclear p27 occurs early in E2-induced type I endometrial carcinogenesis (85% of ECAs) (Lecanda et al., "Transforming Growth Factor-beta, Estrogen, and Progesterone Converge on the Regulation of p27Kip1 in the Normal and Malignant Endometrium," *Cancer Res.* 67:1007-1018 (2007), which is hereby incorporated by reference in its entirety). In vitro, it was shown that E2 induces MAPK (Erk1/Erk2)-mediated phosphorylation of p27 on T187 causing Skp2-dependent proteasomal degradation of p27 to enable E2-induced proliferation of both primary EECs and ECA cell lines (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012), which is hereby incorporated by reference in its entirety). Furthermore, consistent with the opposing effects of E2 and progesterone (Pg) on endometrial cell proliferation, it was shown that Pg markedly increases p27 by decreasing Skp2/Cks1 via a mechanism involving degradation of this complex by their specific E3ligase, APC/Cdh1. These studies provided a novel mechanism by which hormones regulate cell proliferation through the ubiquitin proteasome pathway. In addition, it was shown that that TGF-β prevents p27 degradation also by increasing APC/Cdh1-mediated degradation of Skp2/Cks1, and that p27 is required for TGF-β mediated inhibition of proliferation in endometrial epithelial ("EECs") cells (Lecanda et al., "TGFbeta Prevents Proteasomal Degradation of the Cyclin-dependent Kinase Inhibitor p27kip1 for Cell Cycle Arrest," *Cell Cycle* 8:742-756 (2009), which is hereby incorporated by reference in its entirety). Together, these studies provide compelling evidence that Skp2-dependent degradation of p27 is an important molecular target to harness growth regulation of EECs and is linked to the pathogenesis of E2-induced ECA.

General proteasome inhibitors, such as Bortezomib, as a class of cancer therapeutics have been marginally successful for only a few cancers (e.g., multiple myeloma) (Kane et al., "United States Food and Drug Administration Approval Summary: Bortezomib for the Treatment of Progressive Multiple Myeloma After One Prior Therapy," *Clin. Cancer Res.* 12:2955-2960 (2006); Diefenbach & O'Connor, "Mantle Cell Lymphoma in Relapse: The Role of Emerging New Drugs," *Curr. Opin. Oncol.* 22:419-423 (2010); Orlowski & Kuhn, "Proteasome Inhibitors in Cancer Therapy: Lessons from the First Decade," *Clin. Cancer Res.* 14:1649-1657 (2008), which are hereby incorporated by reference in their entirety), likely because they target the degradation of both tumor suppressors and oncogenes (Kitagawa et al., "Ubiquitin-mediated Control of Oncogene and Tumor Suppressor Gene Products," *Cancer Sci.* 100:1374-1381 (2009), which is hereby incorporated by reference in its entirety). Three enzymes collaborate to transfer (E1), conjugate (E2), and ligate (E3) ubiquitin to a protein for targeted degradation by the 26S proteasome (Hershko & Ciechanover, "The Ubiquitin System," *Ann. Rev. Biochem.* 67:425-479 (1998), which is hereby incorporated by reference in its entirety). The E3 ligases provide the specificity for ubiquitylation of proteins that signal their destruction and thus, inhibitors of specific E3 ligases with substrate specificity for tumor suppressors would be a major advance in proteasome inhibitor therapeutics. However, whereas the identification of specific inhibitors of tumor suppressor degradation has been sought, only one, that blocked p53 degradation by Mdm2, has evolved (Herman et al., "Discovery of Mdm2-MdmxE3 Ligase Inhibitors Using a Cell-Based Ubiquitination Assay," *Cancer Discovery* 1:312-325 (2011), which is hereby incorporated by reference in its entirety). Solving the crystal structure of Skp2-Cks1-p27 (Hao et al., "Structural Basis of the Cks1-dependent Recognition of p27(Kip1) by the SCF(Skp2) Ubiquitin Ligase," *Mol. Cell* 20:9-19 (2005), which is hereby incorporated by reference in its entirety) facilitated the identification of small molecule inhibitors specific to SCF-Skp2/Cks1 E3 ligase activity (Skp2E3LIs). This was accomplished by computational ligand docking and in silico screening of the binding interface between p27 and a pocket formed by the C-terminus of Skp2 interacting with Cks1 (Cardozo & Abagyan, "Druggability of SCF Ubiquitin Ligase-protein Interfaces," *Methods Enzymol.* 399:634-653 (2005) and Cardozo & Pagano, "Wrenches in the Works: Drug Discovery Targeting the SCF Ubiquitin Ligase and APC/C Complexes," *BMC Biochem.* 8 Suppl 1:S9 (2007), which are hereby incorporated by reference in their entirety). Whereas the SCF-Cul1, Skp1, Rbx1 complex can combine with a number of recognition module E3 ligases with numerous target substrates, including oncogenes, the F-box E3 ligase Skp2/Cks1 pocket has specificity for only the cyclin-dependent kinase inhibitors p27 and p21 (Cardozo & Pagano, "Wrenches in the Works: Drug Discovery Targeting the SCF Ubiquitin Ligase and APC/C Complexes," *BMC Biochem.* 8 Suppl 1:S9 (2007), which is hereby incorporated by reference in its entirety). The Skp2E3LIs were shown to directly interact with Skp2 by blocking Skp2-dependent degradation of p27 without affecting the level of Skp2 and other components of the SCF complex (Wu et al., "Specific Small Molecule Inhibitors of Skp2-mediated p27 Degradation," *Chemistry & Biology* 19:1515-1524 (2012), which is hereby incorporated by reference in its entirety). These inhibitors increased cellular levels of p27 in various cancer cell lines. The current study queries whether any of these inhibitors could specifically prevent the degradation of nuclear p27 but not cause accumulation of p27 in the cytoplasm. Therefore, pertinent to this question, we now show that two of five Skp2E3LIs, designated as C2 and C20, increase nuclear p27 while simultaneously decreasing cytoplasmic p27 in an ECA cell line, ECC-1, and primary ECA cells. Moreover, these Skp2E3LIs block both E2-induced proliferation and degradation of p27 suggesting their direct functional interaction with Skp2/Cks1 and strong therapeutic potential for E2-linked ECA. As p27 proteasomal degradation due to aberrantly high levels of Skp2 is a common molecular defect in human cancers and is associated with poor survival in ECA (Kamata et al., "High Expression of Skp2 Correlates with Poor Prognosis in Endometrial Endometrioid Adenocarcinoma," *J. Cancer Res. Clin. Oncol.* 131:591-596 (2005), which is hereby incorporated by reference in its entirety) and other cancers and resistance to chemotherapy (Davidovich et al., "Over-expression of Skp2 is Associated with Resistance to Preoperative Doxorubicin-based Chemotherapy in Primary Breast Cancer," *Breast Cancer Res.* 10:R63 (2008); Frescas & Pagano, "Deregulated Proteolysis by the F-box Proteins SKP2 and Beta-TrCP: Tipping the Scales of Cancer," *Nat. Rev. Cancer* 8:438-449 (2008); Lin et al., "Skp2 Targeting Suppresses Tumorigenesis by Arf-p53-independent Cellular Senescence," *Nature* 464: 374-379 (2010); Assoian & Yung, "A Reciprocal Relationship Between Rb and Skp2: Implications for Restriction Point Control, Signal Transduction to the Cell Cycle and Cancer," *Cell Cycle* 7:24-27 (2008), which are hereby incorporated by reference in their entirety), the bioavailability and nuclear localization of Skp2E3 ligase-mediated degradation of p27 would be a major advance in the inhibition of the proteasome for cancer therapy.

Materials and Methods

Cell Culture and Treatments

The endometrial carcinoma cell line (derived from a well-differentiated endometrioid Type I ECA) ECC-1 cells (ATCC, Manassas, Va.) were plated at a density of $3 \times 10^5$/well/6-well plate and grown in DMEM:F12 supplemented with 10% FBS (BioWest, Ocala, Fla.). The cell line was passaged in the laboratory for fewer than 6 months after receipt. Primary endometrial carcinoma (ECA) cells from fresh ECA tissues from Type I endometrioid tumors derived from hysterectomies of women ages 35-55 years performed at NYU Langone Medical Center and Bellevue Hospital were procured, separated from stromal cells, and adapted to tissue culture as previously described (Lecanda et al., "Transforming Growth Factor-beta, Estrogen, and Progesterone Converge on the Regulation of p27Kip1 in the Normal and Malignant Endometrium," *Cancer Res.* 67:1007-1018 (2007), which is hereby incorporated by reference in its entirety). The protocol was approved by The Institutional Review Board of NYU, informed consent was obtained, and the samples were identified and graded by two surgical pathologists and graded according to the WHO (I-III) for decreased glandular structure and nuclear atypia (Silverberg, "Hyperplasia and Carcinoma of the Endometrium," *Semin. Diagn. Pathol.* 5:135-153 (1988), which is hereby incorporated by reference in its entirety). ECAs were plated at a density of $2.2 \times 10^6$ cells/6-well Primaria® plates (BD Biosciences, San Jose, Calif.) in McCoys 5A media without phenol red containing 10% charcoal-stripped FBS, 2 mM L-Glutamine (Invitrogen) and antimycotic antibiotic solution (Mediatech, Hendon, Va.). ECC-1 cells and primary ECA cells were grown to 70-80% confluence, synchronized in serum-free media for 24 h, treated with 10 ILLM Skp2E3LIs for 18 h or as indicated in the figures. The Skp2E3LIs, C2 (#6544607; ChemBridge Corp, San Diego, Calif.), C20 (#A067/0031209; Ryan Scientific, Mount Pleasant, S.C.), N1 (#6281766; ChemBridge Corp), and C16 (#6744881; ChemBridge Corp), but not L6 (#7839058; ChemBridge Corp) increase p27 protein levels in ECC-1 cells over Vehicle (Veh) control (0.1% DMSO). The Skp2E3LIs have been previously characterized (Wu et al., "Specific Small Molecule Inhibitors of Skp2-mediated p27 Degradation," *Chemistry & Biology* 19:1515-1524 (2012), which is hereby incorporated by reference in its entirety). To determine whether Skp2E3LIs, C2, and C20 block E2-induced degradation of nuclear and cytoplasmic p27, ECC-1 cells were plated, cultured, synchronized, and treated with either 1 nM 17-β estradiol (E2; Sigma), E2 plus the ER antagonist 10 nM ICI 182,780 (ICI, Zeneca Limited, Macclesfield, UK), 10 µM C2, 10 µM C2 plus E2, 10 µM C20, or 10 µM C20 plus E2 for 18 h. The effect of Skp2E3LIs, C2, and C20 on blocking E2E2-induced proliferation in ECC-1 cells was determined using the proliferation assay described below. Another treatment was with the general proteasome inhibitor, 1 µM Lactacystin (Calbiochem, San Diego, Calif.). To determine p27 half-life, ECC-1 cells were cultured, synchronized, and treated with C2, C20, or Vehicle for 18 h, as described above, washed with media, and 20 µM and cycloheximide (CHX; 20 µM) was added to each plate as a chase. Whole cell lysates were collected at increasing time points (0, 2, 4, 6 h) and 20 µg protein/well analyzed for p27 by immunoblotting.

Cell Proliferation, Viability, and Apoptosis Assays

ECC-1 cells were seeded in 96-well plates (BD Biosciences) at a density of $4\times10^3$/well, grown to 70-80% confluence, synchronized in serum-free media for 24 h and treated with increasing doses of C2 and C20 (0.1-10 µM) in triplicate, as described above and cell proliferation was determined by the CellTiter 96 Aqueous One Solution (MTS) assay (Promega, Madison, Wis.). Values were calculated as percent of Vehicle-treated control ±SD, as described (Lecanda et al., "TGFbeta Prevents Proteasomal Degradation of the Cyclin-dependent Kinase Inhibitor p27kip1 for Cell Cycle Arrest," *Cell Cycle* 8:742-756 (2009), which is hereby incorporated by reference in its entirety). The half-maximal effective concentration (EC50) of C2 in inhibiting proliferation of ECC-1 was obtained by treating and analyzing the cells as described above for determining growth inhibition, and analyzing the values derived as percent of Vehicle treated control with the Hillslope method, which characterizes the slope of the curve at the midpoint, using GraphPad Prism software to determine the variable slope dose. The Hillslope experiment is graphed on a logarithmic scale representing the increasing concentrations of C2 treatment. Cytotoxicity of the Skp2E3LIs was determined by plating the ECC-1 cells at a density of $1.5\times10^5$/well in 12-well plates (BD Biosceinces), growing and synchronizing the cells as described above. The cells were treated with 10 µM Skp2E3LIs (C2, C20, C16, N1, and L6) for 48 h and supernatants were collected by centrifugation, adherent cells obtained by trypsinization, and the number of dead cells per 100 was determined by trypan blue (Invitrogen) exclusion and cell counting. Values were calculated as percent of Vehicle-treated control. The values (y axis) were determined as percent of Vehicle control. In separate experiments, the effect of Skp2E3LIs on apoptosis was determined by growing, synchronizing, and treating ECC-1 cells with 10 µM Skp2E3LIs for 18 h, and analyzing for Caspase 3 cleavage by immunoblotting.

Immunoblot Analysis

Whole cell lysates were prepared in ice cold RIPA buffer (50 mM Tris-HCL, 150 mM NaCl, 0.25% sodium deoxycholate, 1% NP-40 and 1 mM EDTA) containing 1 mM $Na_3VO_4$, pH 7.4) and 1× Protease Inhibitor Cocktail (Sigma Chem, St Louis, Mo.). Following freezing and thawing once, and soluble proteins obtained by centrifugation at 14,000×g for 10 min at 4° C. Protein concentrations were quantified (BCA kit, Thermo Scientific, Rockland, Ill.) and 20 µg protein in Laemmli buffer were subjected to SDS-PAGE (12.5% polyacrylamide) and immunoblotted using anti-p27 and anti-Skp2 antibodies to probe protein levels, as described (Lecanda et al., "TGFbeta Prevents Proteasomal Degradation of the Cyclin-dependent Kinase Inhibitor p27kip1 for Cell Cycle Arrest," *Cell Cycle* 8:742-756 (2009), which is hereby incorporated by reference in its entirety). For subcellular fractionation, following treatments, cells were separated into nuclear and cytoplasmic fractions using the NE-PER kit (Thermo Scientific), and 10 µg cytoplasmic and nuclear protein fractions were loaded onto SDS-PAGE for immunoblotting. Following protein transfer onto nitrocellulose membranes, the membrane was blocked with 5% non-fat dry milk in TBS containing 0.1% Tween 20 (TBST) for 1 h, incubated overnight with mouse anti-human p27 (1:1000, Clone 57, BD Transduction Labs) or mouse anti-human p45/Skp2 (1:1000, Clone 8D9, Invitrogen, Grand Island, N.Y.) or rabbit anti-human Caspase-3 antibody (1:500, Clone 8G10, Cell Signaling Technology (Danvers, Mass.)). Purity of the subcellular fractions was confirmed using mouse anti-human α-tubulin (1:10,000, Clone B-5-1-2, Sigma) for cytoplasmic or rabbit anti-human Sp1 (1:1000, Clone H-225, Santa Cruz Biotechnology, Santa Cruz, Calif.) for nuclear fractions. The membranes were incubated with peroxidase-conjugated goat anti-rabbit or goat anti-mouse secondary antibodies in TBST (1:2000; Thermo Scientific). The blots were stripped and re-probed with mouse anti-β-actin (1:10000, Clone AC15, Sigma) as loading control. Protein bands were resolved using the SuperSignal West Dura kit (Thermo Scientific), visualized by exposure to X-ray film (HyBlot; Denville Scientific, Denville, N.J.), and following densitometric scanning (Kodak Logic-100), the protein bands were quantified by normalizing to β-actin and compared to the untreated control, and the values represented by the graphs of relative protein levels compared to actin in each well and shown as % of Vehicle control.

RNA Interference

ECC-1 cells in complete media were seeded at $1.2\times10^5$/well in 12-well plates and after 24 h the cells were transfected with either control siRNA or 10 nM Skp2 siRNA using HiPerfect transfection reagent (Qiagen; Valencia, Calif.) and siRNA to three different sites including a pool of siRNAs as shown in the experiment, as previously described (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012), which is hereby incorporated by reference in its entirety). To determine the effect of Skp2E3LIs, C2, and C20 on p27 levels following knocking-down of Skp2 24 h after transfection, the cells were synchronized and treated with C2 and C20 and analyzed by immunoblotting. To determine the effect of C2 and C20 on cell proliferation after knock-down of Skp2, the cells were seeded in 96-well plates at a density of $1\times10^4$ in complete media, transfected, synchronized, treated with C2 and C20, and cell proliferation determined, as described above.

Statistical Analysis

All proliferation and toxicity data are presented as means±SD. A two-tailed, paired Students's t test was used to predict statistical significance of the comparison between two means with results significant at *P<0.05 using GraphPad Prism software.

Results and Discussion

Figure 11A:
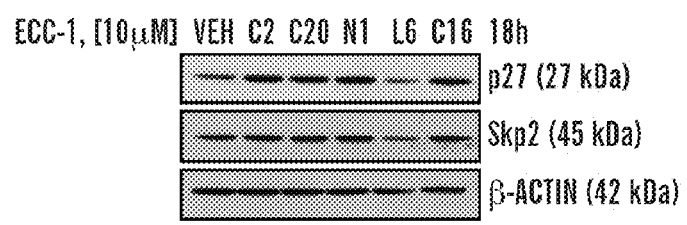
FIGS. 11A-D show that small molecule inhibitors of SCF-Skp2E3 ligase ("Skp2E3LIs") increase nuclear p27 in the endometrial carcinoma (ECA) cell line, ECC-1.
Figure 11B:
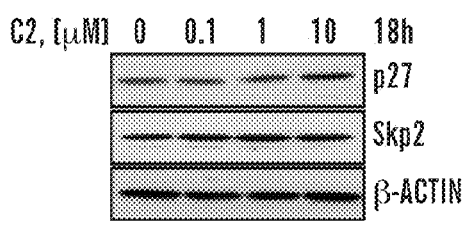
Figure 11B:
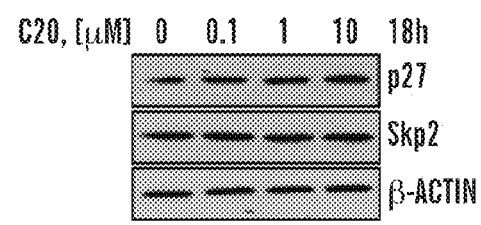
Figure 11C:
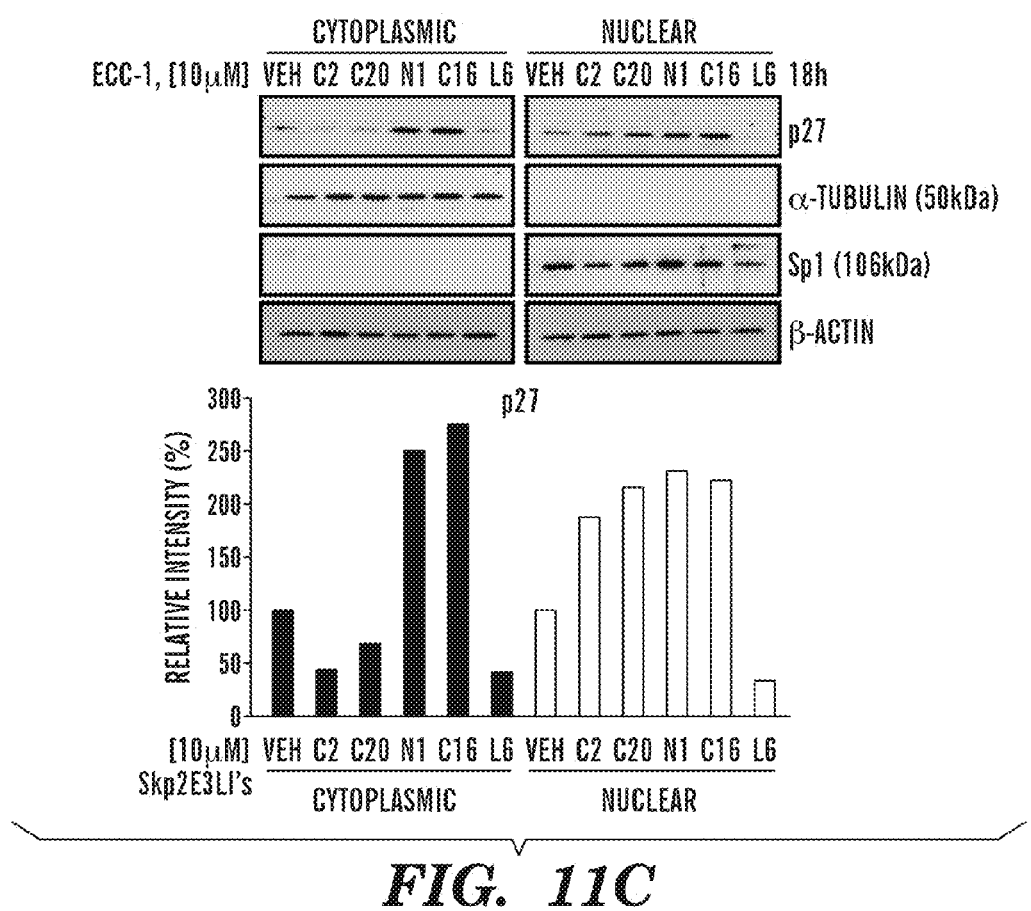
Figure 11D:
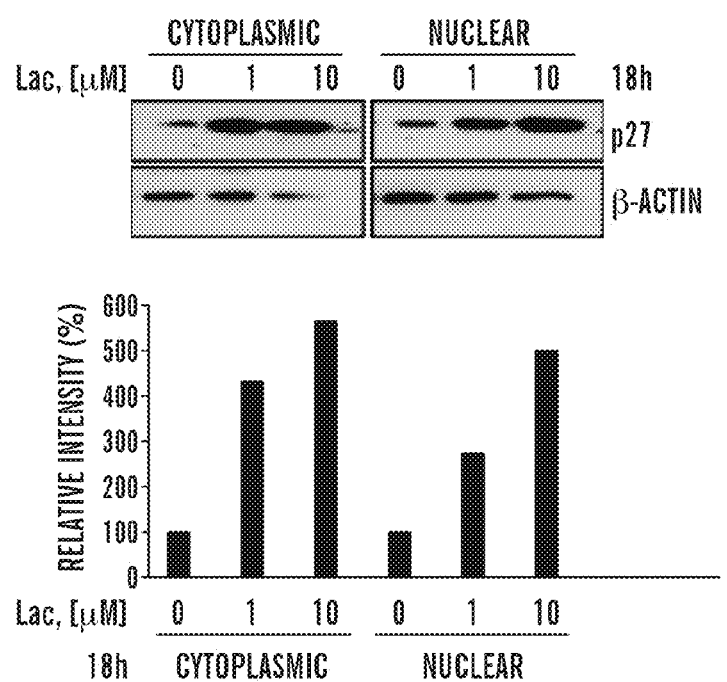
Figure 12A:
FIGS. 12A-B show estrogen (E2)-induced decrease of p27 is mediated by ERK-dependent phosphorylation on Thr187.
Figure 12B:
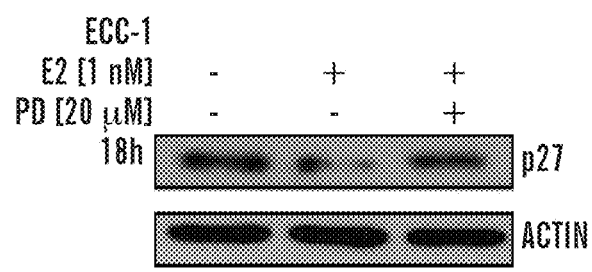

Small Molecule Inhibitors of SCF-Skp2E3 Ligase (Skp2E3LIs) Increase Nuclear p27 and Inhibit Proliferation An array of the small molecule inhibitors of SCF-Skp2/Cks1 (Skp2E3LIs) were previously shown to have differential effects in cell based assays using melanoma, breast, and prostate cancer cell lines in terms of the degree of p27 stabilization and cell cycle effects (Wu et al., "Specific Small Molecule Inhibitors of Skp2-mediated p27 Degradation," *Chemistry & Biology* 19:1515-1524 (2012), which is hereby incorporated by reference in its entirety). It has been shown that p27 is an important molecular target for growth arrest in primary endometrial epithelial cells (EECs) and ECA cell lines (Lecanda et al., "Transforming Growth Factor-beta, Estrogen, and Progesterone Converge on the Regulation of p27Kip1 in the Normal and Malignant Endometrium," Cancer Res. 67:1007-1018 (2007); Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012); Lecanda et al., "TGFbeta Prevents Proteasomal Degradation of the Cyclin-dependent Kinase Inhibitor p27kip1 for Cell Cycle Arrest," *Cell Cycle* 8:742-756 (2009); Muggia et al., *Future Directions: New Targets*, p. 267-283, Totowa, N.J.: Humana Press, Inc. (2009), which are hereby incorporated by reference in their entirety). It was first determined whether Skp2E3LIs could increase p27 in an ECA cell line, ECC-1. As shown in FIG. 11A, four out of five Skp2E3LIs added to cells at 10 µM for 18 h increase the levels of p27 by 2-2.5-fold. Whereas it has been thought that Skp2 is localized in the nucleus where it ubiquitylates p27 (Bashir et al., "Phosphorylation of Ser72 is Dispensable for Skp2 Assembly Into an Active SCF Ubiquitin Ligase and Its Subcellular Localization," *Cell Cycle* 9:971-974 (2010) and Boutonnet et al., "Phosphorylation of Ser72 Does Not Regulate the Ubiquitin Ligase Activity and Subcellular Localization of Skp2," *Cell Cycle* 9:975-979 (2010), which are hereby incorporated by reference in their entirety), it has been shown that Skp2 can reside in the cytoplasm (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012); Gao et al., "Phosphorylation by Akt1 Promotes Cytoplasmic Localization of Skp2 and Impairs APCCdh1-mediated Skp2 Destruction," *Nat. Cell Biol.* 11:397-408 (2009); Lin et al., "Phosphorylation-dependent Regulation of Cytosolic Localization and Oncogenic Function of Skp2 by Akt/PKB," *Nat. Cell Biol.* 11:420-432 (2009), which are hereby incorporated by reference in their entirety) and also, that E2 increases and Pg decreases Skp2 in both subcellular compartments with an inverse effect on the levels of nuclear and cytoplasmic p27 (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012), which is hereby incorporated by reference in its entirety). The optimal concentration of C2 and C20 that increases p27 was 10 µM (2.3 and 2.2 over control, respectively; FIG. 11B), with no further increase at 20 µM (FIGS. 12A-B). C2 and C20 do not effect the levels of Skp2 confirming their specificity for Skp2 E3 ligase activity. Importantly, it was assessed whether any of the Skp2E3LIs could specifically increase nuclear p27 since accumulation of cytoplasmic p27 would be an adverse effect of these potential therapeutic agents (Chu et al., "The Cdk Inhibitor p27 in Human Cancer: Prognostic Potential and Relevance to Anticancer Therapy," *Nat. Rev. Cancer,* 8:253-267 (2008); Wander et al., "p27: A Barometer of Signaling Deregulation and Potential Predictor of Response to Targeted Therapies," *Clin. Cancer Res.* 17:12-18 (2011); Serres et al., "Cytoplasmic p27 is Oncogenic and Cooperates with Ras both In Vivo and In Vitro," *Oncogene* 30:2846-2858 (2011); Denicourt et al., "Relocalized p27Kip1 Tumor Suppressor Functions as a Cytoplasmic Metastatic Oncogene in Melanoma," *Cancer Res.* 67:9238-9243 (2007), which are hereby incorporated by reference in their entirety). FIG. 11C shows that treatment of ECC-1 cells, with basal levels of p27 in the cytoplasm with C2 and C20 for 18 h specifically increases nuclear p27 by 1.8 and 2.2-fold compared to Vehicle control. In contrast, N1 and C16 increase p27 in both the nucleus by 2.3 and 2.2 fold, respectively, and cytoplasm p27 by 2.5 and 2.7-fold, respectively. This is identical to lactacystin, a general proteasome inhibitor (i.e., Bortezomib), which increases p27 in both subcellular fractions (FIG. 11D). Therefore, the Skp2E3LIs, C2, and C20 could specifically increase nuclear p27.

Figure 13A:
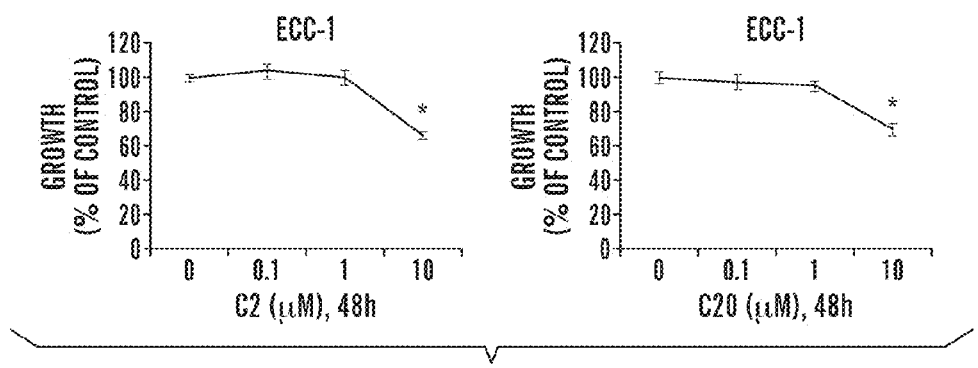
FIGS. 13A-D show that the Skp2e3LIs C2 and C20 inhibit cell proliferation, are not cytotoxic, and do not induce apoptosis in ECC-1 cells.
Figure 13B:
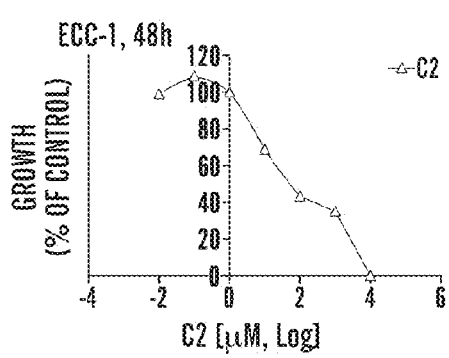
Figure 13C:
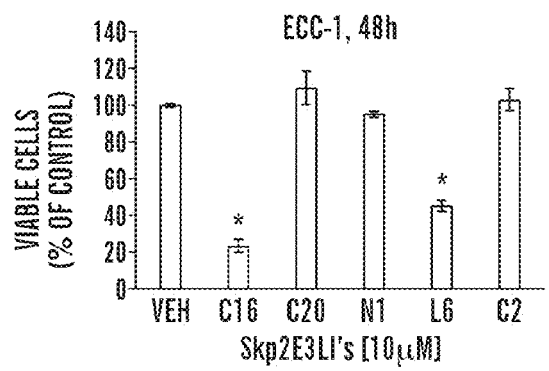
Figure 13D:
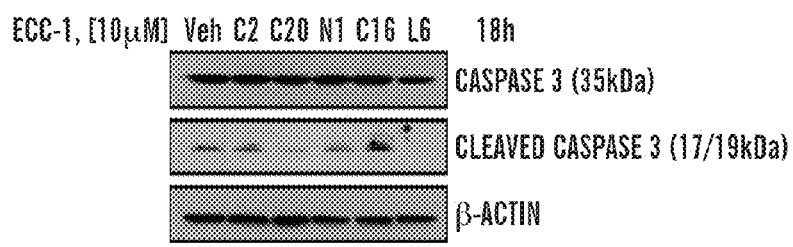

As shown in FIG. 13A, at the concentration causing maximal accumulation of p27 (10 µM), C2 and C20 were functionally active as a statistically significant inhibition of cellular proliferation was obtained 33% (p≤0.012) and 30% (p≤0.019), respectively, over the Vehicle control; no greater effect on proliferation was observed with 20 µM. The same percent inhibition was obtained in response to Pg, which showed a similar relationship between the amount of p27 increased by the inhibitor (2-fold) and the extent of growth inhibition (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012), which is hereby incorporated by reference in its entirety). From these data, an EC50 for C2 of 14.32 µM was obtained (FIG. 13B). As shown in FIG. 13C, C2 and C20 (10 µM) were not cytotoxic following treatment of ECC-1 cells for 48 h. However, both C16, which increased nuclear and cytoplasmic p27 and L6, which did not increase p27, induced 77% (p≤0.001) and 55% (p≤0.007) cell death, respectively. Notably, as shown in FIG. 13D, whereas C2 and C20 activate caspase 3 to a similar extent as the control, in accordance with the toxicity shown for C16, this compound shows cleavage of caspase 3. These data suggest that C2 and C20 indeed reduce cell growth by inhibiting proliferation and not by apoptosis in ECC-1 cells. The requirement for p27 in the effectiveness of C2 and C20 to affect cell cycle arrest by increasing the number of cells in G0/G1 was previously shown in Mel 501 melanoma cells as the inhibitors were not effective when p27 was knocked-down (Wu et al., "Specific Small Molecule Inhibitors of Skp2-mediated p27 Degradation," *Chemistry & Biology* 19:1515-1524 (2012), which is hereby incorporated by reference in its entirety). The results shown here with ECC-1 cells strongly suggest that the Skp2E3LIs, C2, and C20 reduce cell growth by increasing nuclear p27 through the specific inhibition of Skp2 E3ligase activity without increasing cytoplasmic p27.

Figure 14A:
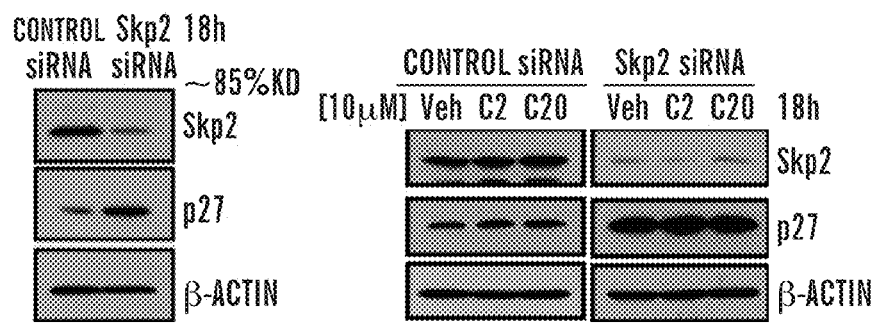
FIGS. 14A-E shows that the small molecule inhibitors of SCF-Skp2E3 ligase (Skp2E3LIs), C2 and C20, block estrogen (E2)-induced degradation of nuclear p27 and E2-induced proliferation in ECC-1 cells.
Figure 14B:
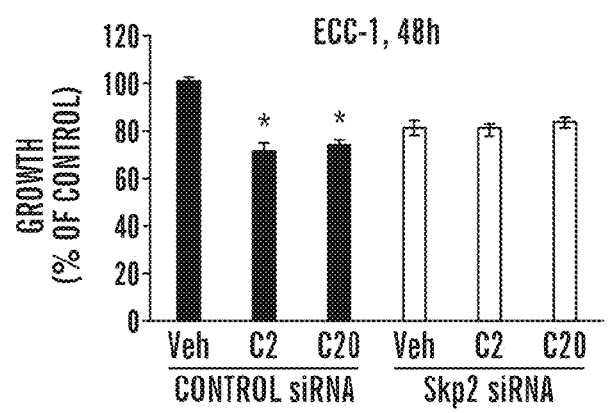

Skp2E3LIs, C2, and C20 Block Estrogen (E2)-Induced Proteasomal Degradation of Nuclear p27 and E2-Induced Proliferation It was previously shown that knocking-down Skp2 in ECA cell lines completely obviated both E2-induced proliferation and degradation of nuclear (and cytoplasmic) p27 (Huang et al., "Estrogen and Progesterone Regulate p27kip1 Levels via the Ubiquitin-Proteasome System: Pathogenic and Therapeutic Implications for Endometrial Cancer," *PLoS One* 7:e46072 (2012), which is hereby incorporated by reference in its entirety). This strongly suggests that the pathogenesis of E2-induced ECA is dependent on Skp2-mediated degradation of p27. As shown in FIGS. 14A and 14B, the increase in p27 nuclear levels and inhibition of cell proliferation at 29% and 27% by C2 and C20, respectively, was completely abrogated following Skp2 knock-down (by 85%) in ECC-1, thereby confirming the specific inhibition of Skp2/Cks1 E3 ligase activity by these inhibitors. In addition, knocking-down Skp2 decreases cell proliferation (by 19%). As E2 induces p27 degradation by decreasing the E3 ligase APC/Cdh1 to spare Skp2 and Cks1 proteins from proteasomal degradation so that SCF-Skp2/Cks1 can degrade p27 (Huang et al., "Estrogen and Progesterone Regulate p27kip1 Levels via the Ubiquitin-Proteasome System: Pathogenic and Therapeutic Implications for Endometrial Cancer," *PLoS One*

7:e46072 (2012), which is hereby incorporated by reference in its entirety), it is shown that whereas the classic ER blocker ICI182,780 abrogated the 67% decrease in nuclear p27 induced by E2 to the level of untreated control (FIG. 14C), both C2 and C20 block E2-induced degradation of p27 nearly restoring nuclear p27 levels close to the 2-fold increase over the control, as observed in FIGS. 11B and 11C. In contrast, both C2 and C20 decrease cytoplasmic p27 levels by approximately 33%. Whereas previous studies using cancer cell lines show that p27 levels are increased by Skp2E3LIs (Wu et al., "Specific Small Molecule Inhibitors of Skp2-mediated p27 Degradation," Chemistry & Biology 19:1515-1524 (2012), which is hereby incorporated by reference in its entirety) that C2 and C20 block, E2-induced degradation of nuclear p27 in ECA cells provides evidence that these Skp2E3LIs have a direct functional effect on Skp2/Cks1 E3 ligase activity. This activity underscores the potential for these inhibitors to treat endometrial hyperplasia and prevent ECA as this pre-neoplastic state is caused by unopposed E2, which precedes type I ECA (Ellenson & Wu, "Focus on Endometrial and Cervical Cancer," Cancer Cell 5:533-538 (2004) and Lacey et al., "Endometrial Hyperplasia and the Risk of Progression to Carcinoma," Maturitas 63:39-44 (2009), which are hereby incorporated by reference in their entirety).

Figure 14C:
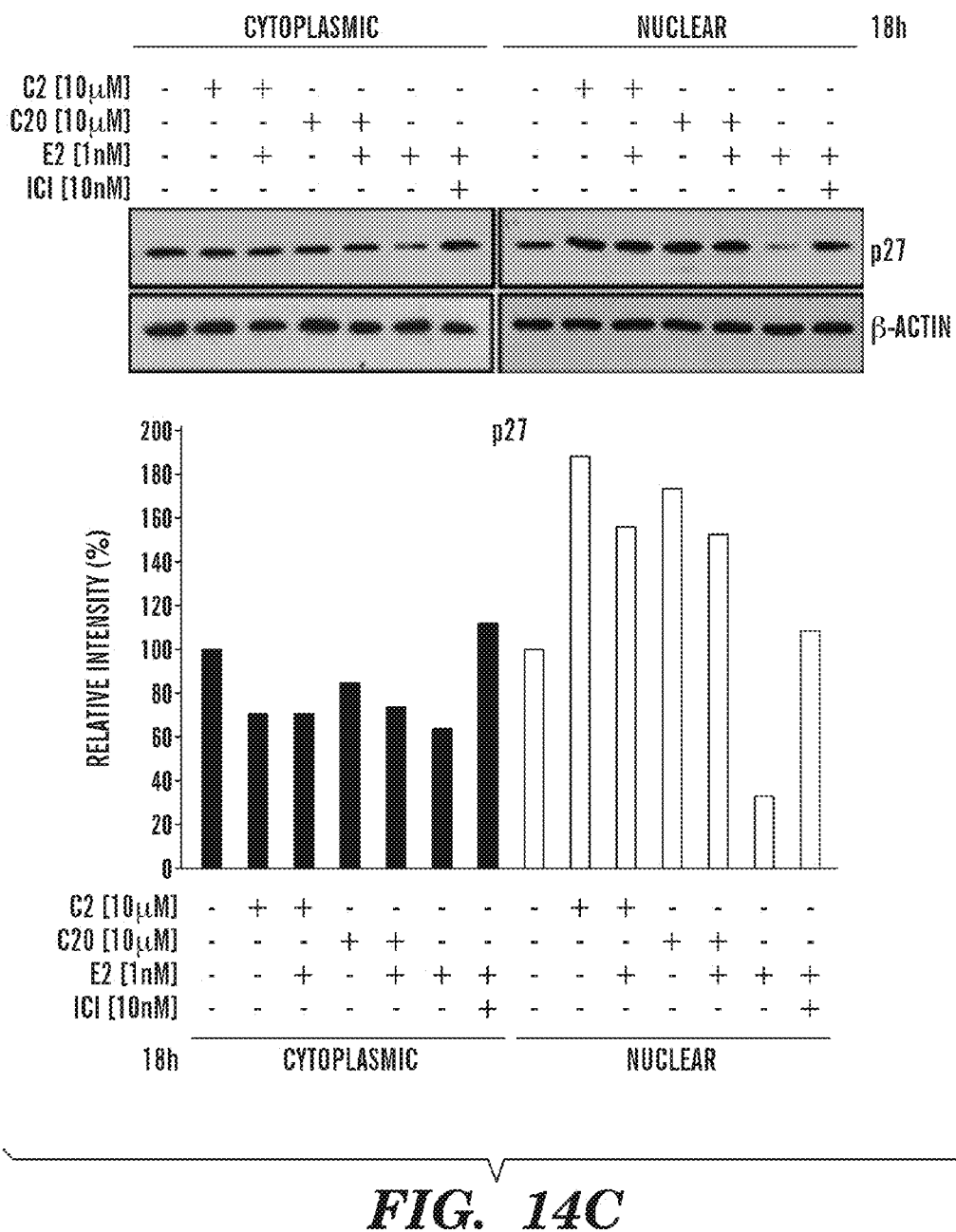
Figure 14D:
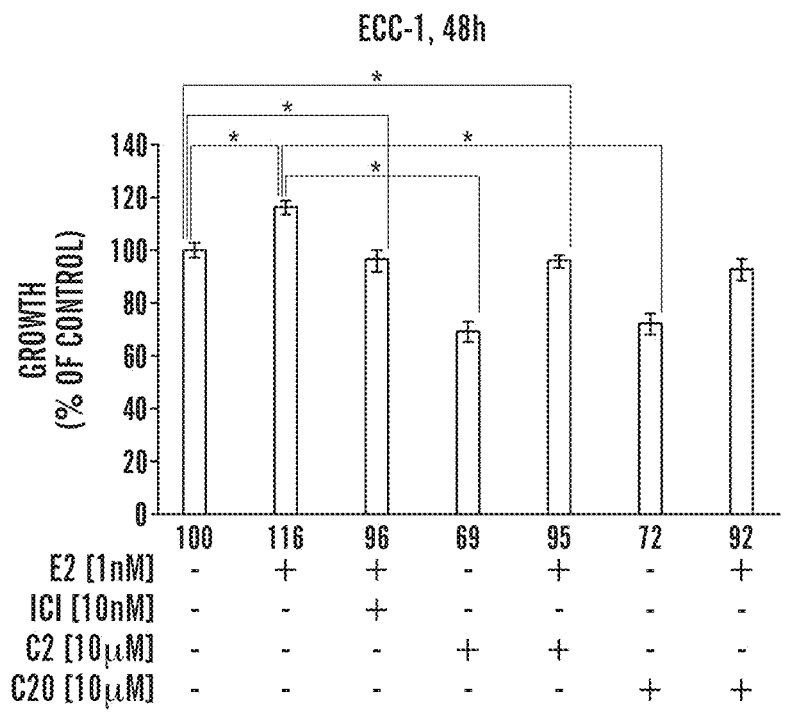
Figure 14E:
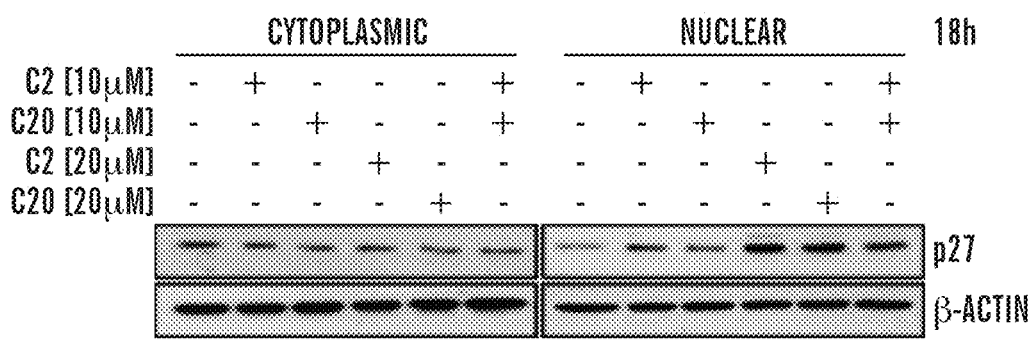

The Skp2E3LI C2 Increases Nuclear p27 while Decreasing p27 in the Cytoplasm in an ECA Cell Line and Primary Endometrial Carcinoma Cells Importantly, blocking E2-induced proliferation by C2 and C20 was equal to the effect of blocking ER activation with ICI 182,780 (FIG. 14D). The partial reversal of these Skp2E3LIs on E2-induced proliferation was statistically significant ($p \leq 0.022$; $p \leq 0.019$) and is commensurate with their ability to recover p27 levels (FIG. 14C). Addition of C2 and C20 together (FIG. 14E) did not further increase nuclear p27 levels, suggesting they both block the interactive pocket formed by Skp2/Cks1 for which they were originally screened by ICM-VLS (Wu et al., "Specific Small Molecule Inhibitors of Skp2-mediated p27 Degradation," Chemistry & Biology 19:1515-1524 (2012), which is hereby incorporated by reference in its entirety). To optimize the pharmacologic action of Skp2E3LIs, these compounds are being derivatized to improve solubilities, bioavailabilities, and potency and to decrease toxicity. C2 and C20 as well as other Skp2E3LIs that increase p27 levels by blocking Skp2 ubiquitylating activity have different chemical backbone scaffolds and, therefore, maximize potential for improving the compounds including increasing probabilities for cell-type specific effects as well as for in vivo use in preclinical animal studies.

Figure 15A:
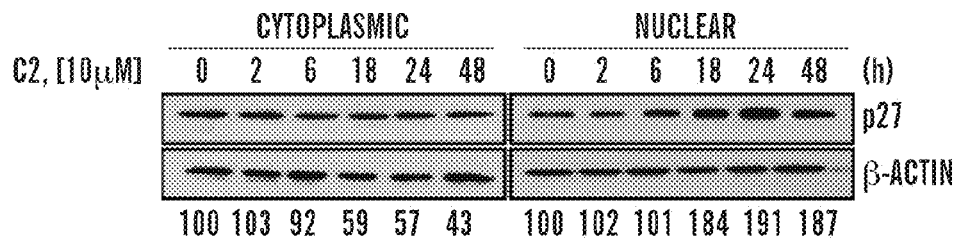
FIGS. 15A-C show that the Skp2E3LI C2 increases nuclear p27 while decreasing p27 in the cytoplasm over time.
Figure 15B:
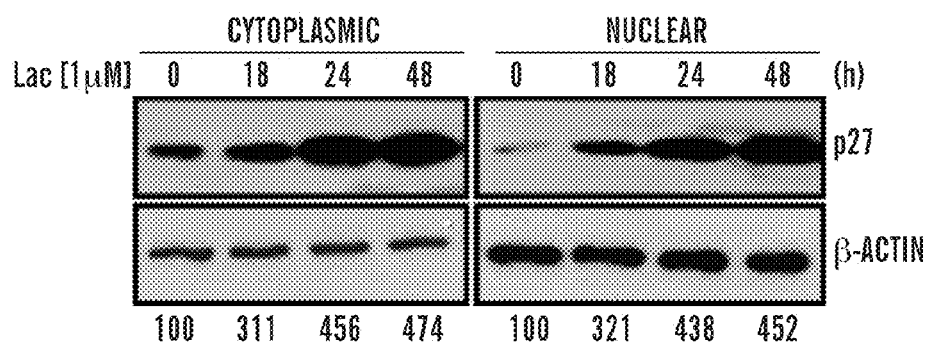
Figure 15C:
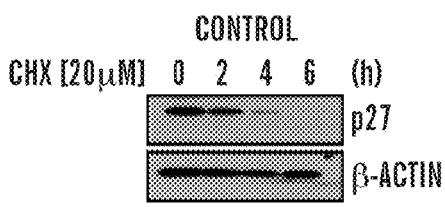
Figure 15C:
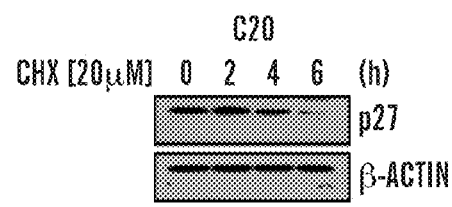
Figure 15C:
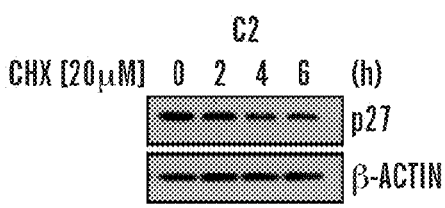
Figure 15C:
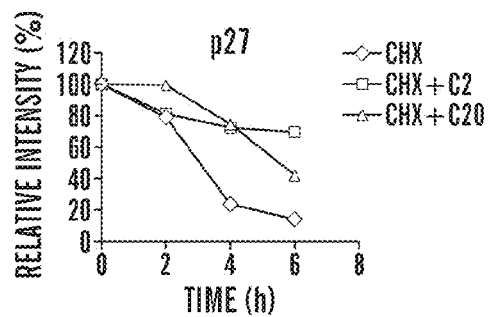
Figure 16:
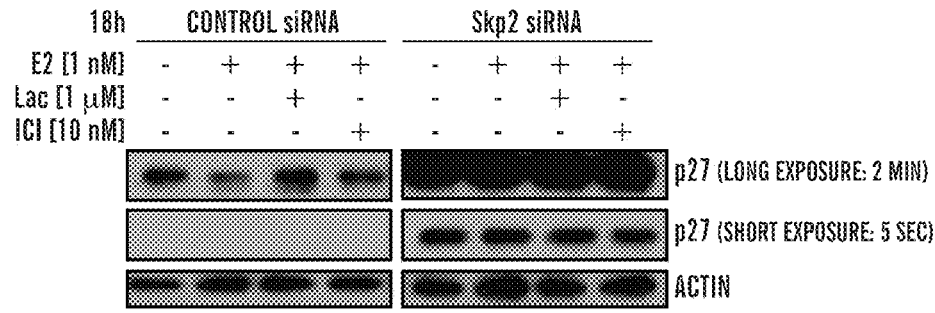
FIG. 16 shows that knocking-down Skp2 (Skp2 siRNA) blocks the estrogen (E2)-induced decrease in p27 and markedly increases the level of p27. ECC-1 cells were seeded at $1.2 \times 10^5$ in 12-well plates in DMEM/F12 supplemented with 10% FBS. 24 h later, the cells were transfected with either control siRNA (Santa Cruz. Biotechnology) or Skp2 siRNA (pool of 3 siRNAs) using HiPerfect transfection reagent (Qiagen). After 24 h, the cells were synchronized and treated for 18 h with 1 nM E2 or 1 nM E2 plus 1 µM Lactacystin (Lac; proteasome inhibitor) or 1 nM E2 plus 10 nM ICI 182,780 (ICI; E2 antagonist), total cell lysates prepared in cold RIPA buffer, and 20 µg of total protein analyzed for Skp2 and p27 levels. The membranes were blocked with 5% non-fat dry milk in TBST for 1 h and incubated overnight at 4° C. with mouse anti-human p45/Skp2 (1:1000, 8D9, Invitrogen) or mouse anti-human p27 (BD Transduction Labs; membranes were cut a the appropriate anticipated molecular weight and incubated separately), as described for each antibody in Example 8 herein, followed by peroxidase conjugated goat anti-mouse IgG (1:2000) in TBST for 1 h. The blots were reprobed with anti-actin and bands quantified as described in FIG. 12A. The blot shows that in the control siRNA transfected cell, E2 decreases p27 by 50%, which is completely blocked by Lac and nearly completely blocked by ICI compared to the untreated control. In the Skp2 siRNA transfected cells, the p27 levels were greatly increased as shown by the 2 min compared to 5 sec exposure. Importantly, p27 levels remained unchanged following treating the cells with E2. (n=3 separate experiments).

The therapeutic success of Skp2E3LIs would be heightened if these compounds could increase nuclear p27 while simultaneously decreasing cytoplasmic p27. As this was implicated in FIG. 11B, a time course of C2 treatment of ECC-1 cells was performed and it was shown (FIG. 15A) that p27 increases in the nucleus between 18 h to 24 h with no further increase at 48 h. Compared to the general proteasome inhibitor Lactacystin, which increases p27 in both the nucleus and cytoplasm (FIG. 15B), C2 causes a simultaneous increase in nuclear p27 while decreasing cytoplasmic p27 (FIG. 15A and FIG. 16). By 18 h, the cytoplasm contained half the level of p27 while nuclear p27 doubled. The X-ray film exposure times were comparable at 30 sec. Whereas there is a higher level of nuclear p27 in the Lactacystin-treated cells, inhibition of proliferation was similar to the Skp2E3LIs at 36%. These experiments indicate that C2 facilitates p27 translocation from the cytoplasm to the nucleus thereby providing a dual positive functional significance of this specific Skp2E3LI. An assessment of the dynamic influence of Skp2E3LIs on nuclear cytoplasmic shuttling and nuclear retention of p27 by single cell high content imaging (Szafran et al., "Androgen Receptor Mutations Associated with Androgen Insensitivity Syndrome: A High Content Analysis Approach Leading to Personalized Medicine," PLoS One 4:e8179 (2009); Szafran et al., "Androgen Receptor Functional Analyses by High Throughput Imaging: Determination of Ligand, Cell Cycle, and Mutation-specific Effects," PLoS One 3:e3605 (2008); Ashcroft et al., "High Content Imaging-based Assay to Classify Estrogen Receptor-alpha Ligands Based on Defined Mechanistic Outcomes," Gene 477:42-52 (2011), which are hereby incorporated by reference in their entirety) provides further clues to this important putative function of C2 and other further optimized Skp2E3LIs. To measure the degree of p27 stabilization, it is shown by incubating the cells with C2 and C20 in the presence of cyclohexamide (CHX) that these inhibitors increase the half-life of p27 at 3.2 h for control cells and by 6.1 and 2.7 h, respectively (FIG. 15C). This stabilization of p27 by Skp2E3LIs is similar to previous studies in which C20 and C16 extended the half-life of p27 to 5 and 3 h, respectively, in the 501 melanoma cell line (Wu et al., "Specific Small Molecule Inhibitors of Skp2-mediated p27 Degradation," Chemistry & Biology 19:1515-1524 (2012), which is hereby incorporated by reference in its entirety).

Figure 17A:
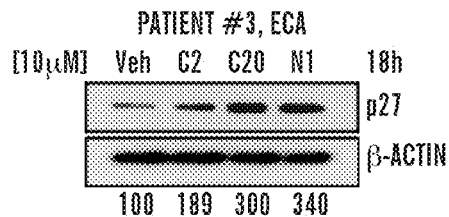
FIGS. 17A-B show that Skp2LIs stabilize nuclear p27 and decrease cytoplasmic p27 in primary endometrial carcinoma cells isolated from fresh endometrial tissue.
Figure 17B:
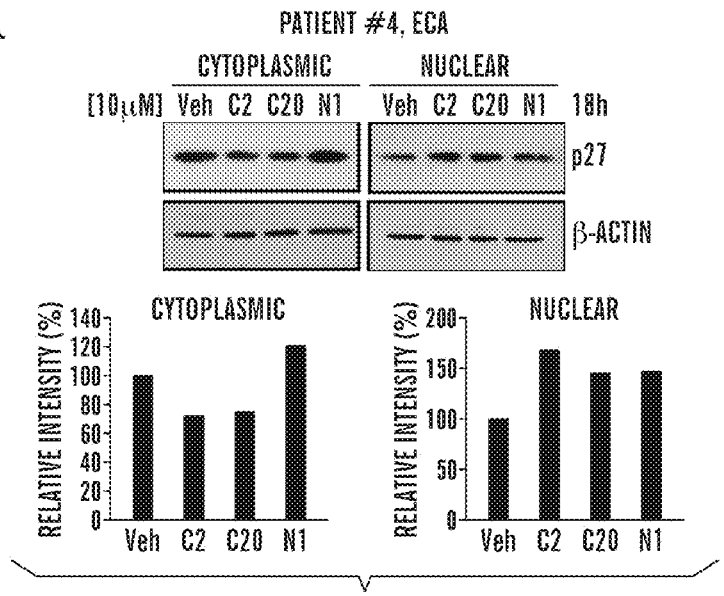

As a step toward interrogating the potential for Skp2E3LIs as pharmacological inhibitors of p27 degradation to regain growth control in cancer, primary ECA cells isolated from endometrioid type I uterine surgical tissues were treated with 10 μM C2, C20, and N1 for 18 h. As shown in FIG. 17A, C2, C20, and N1 increase p27 levels by 1.9-, 3-, and 3.4-fold over the Vehicle-treated control, respectively, in cells from a grade I ECA. Following subcellular fractionation of Skp2E3LI-treated ECA cells derived from a grade II type I ECA, C2 and C20 specifically decrease p27 in the cytoplasm by approximately 25% while simultaneously increasing nuclear p27 by 67% and 46%, respectively. N1 causes accumulation of p27 in both subcellular compartments (FIG. 17B). The patient's ECA cells shown in FIG. 17B have a greater amount of cytoplasm compared to nuclear p27 in the control suggesting that part of the pathology is cytoplasmic mislocalization of p27. In addition, C2 and C20 appear to drive accumulation of nuclear p27 from a cytoplasmic pool or by an unknown mechanism (e.g., KPC-mediated cytoplasmic degradation of p27) (Kotoshiba et al., "Molecular Dissection of the Interaction Between p27 and KPC, the Ubiquitin Ligase that Regulates Proteolysis of p27 in G1 Phase," J. Biol. Chem., published online Mar. 3, 2005), which is hereby incorporated by reference in its entirety) to specifically decrease cytoplasmic p27. Further studies are needed to unravel this interesting role of Skp2E3LIs. Nonetheless, the effects of C2 and C20 on ECA cells from patients provides proof of concept that Skp2E3LIs can be further developed as a novel therapeutic approach to block Skp2-dependent degradation of p27.

Figure 18:
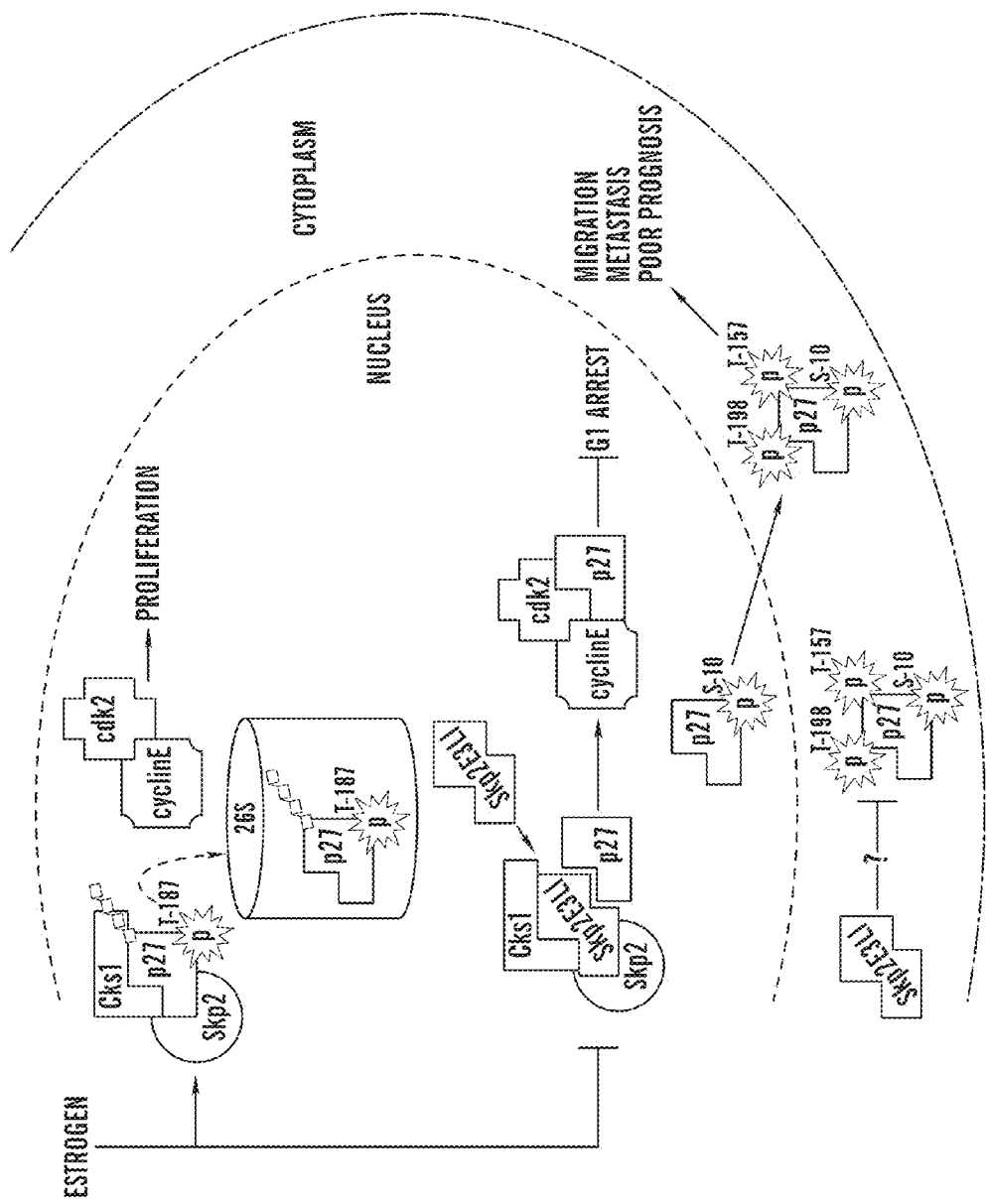
FIG. 18 shows that Skp2E3LIs stabilize nuclear p27, inhibit cell proliferation, and block estrogen (E2)-induced degradation of p27 and E2-induced cell proliferation in ECC-1 cells and primary ECA cells. The diagram depicts phosphorylation of p27 on T187, which causes recognition of p27 by the SCF-Skp2/Cks1 complex and subsequent polyubiquitylation (Ub) of p27 by Skp2 in a pocket formed by the interaction of Skp2 with Cks1 (Cardozo & Abagyan, "Drugability of SCF Ubiquitin Ligase-protein Interfaces," *Methods Enzymol.* 399:634-653 (2005) and Cardozo & Pagano, "Wrenches in the Works: Drug Discovery Targeting the SCF Ubiquitin Ligase and APC/C Complexes," *BMC Biochem.* 8 Suppl 1:S9 (2007), which are hereby incorporated by reference in their entirety). As ubiquitylated p27 is degraded in the 26S proteasome (26S), CyclinE/Cdk2 becomes available to enact unrestrained cell proliferation (Wander et al., "p27: A Barometer of Signaling Deregulation and Potential Predictor of Response to Targeted Therapies," *Clin. Cancer Res.* 17:12-18 (2011), which is hereby incorporated by reference in its entirety). Loss of nuclear p27 and increased Skp2 is characteristic of many human cancers (Chu et al., "The Cdk Inhibitor p27 in Human Cancer: Prognostic Potential and Relevance to Anticancer Therapy," *Nat. Rev. Cancer* 8:253-267 (2008); Wander et al., "p27: A Barometer of Signaling Deregulation and Potential Predictor of Response to Targeted Therapies," *Clin. Cancer Res.* 17:12-18 (2011); Gstaiger et al., "Skp2 is Oncogenic and Overexpressed in Human Cancers," *Proc. Natl. Acad. Sci. USA* 98:5043-5048 (2001), which are hereby incorporated by reference in their entirety). E2 causes p27 MAPK-mediated phosphorylation of p27 on T187 and increases Skp2 and Cks1, thereby inducing cell proliferation as a mechanism for E2-linked endometrial hyperplasia and ECA (Huang et al., "Estrogen and Progesterone Regulate p27kip1 Levels Via the Ubiquitin-proteasome System: Pathogenic and Therapeutic Implications for Endometrial Cancer," *PLoS One* 7:e46072 (2012), which is hereby incorporated by reference in its entirety). The small molecule inhibitors of Skp2 E3 ligase (Skp2E3LIs) C2 and C20 interact with the binding interface between p27 and the pocket of Skp2 interacting with Cks1 and, thus, prevent p27 from binding (Wu et al., "Specific Small Molecule Inhibitors of Skp2-mediated p27 Degradation," *Chemistry & Biology* 19:1515-1524 (2012), which is hereby incorporated by reference in its entirety). p27 is free to bind CyclinE/Cdk2 causing G1 arrest to harness the unrestrained proliferation of cancer cells. The Skp2E3LIs block E2-induced degradation of p27 and E2-induced proliferation and, therefore, are a potential novel therapeutic approach for ECA. Phosphorylation of p27 on S10 causes its export to the cytoplasm while phosphorylation of p27 on T157 and T198 prevents its nuclear entry (Ishida et al., "Phosphorylation of p27Kip1 on Serine 10 is Required for Its Binding to CRM1 and Nuclear Export," *J. Biol. Chem.* 277:14355-14358 (2002) and Shin et al., "Phosphorylation of p27Kip1 at Thr-157 Interferes with Its Association with Importin Alpha During G1 and Prevents Nuclear Re-entry," *J. Biol. Chem.* 280:6055-6063 (2005), which are hereby incorporated by reference in their entirety). Cytoplasmic mislocalization of p27 not only allows CyclinE/Cdk2 activity for cell cycle progression but represses RhoA signaling causing cell migration and metastasis (Chu et al., "The Cdk Inhibitor p27 in Human Cancer: Prognostic Potential and Relevance to Anticancer Therapy," *Nat. Rev. Cancer* 8:253-267 (2008) and Denicourt et al., "Relocalized p27Kip1 Tumor Suppressor Functions as a Cytoplasmic Metastatic Oncogene in Melanoma," *Cancer Res.* 67:9238-9243 (2007), which are hereby incorporated by reference in their entirety). Skp2E3LIs increase nuclear p27 while simultaneously decreasing cytoplasmic p27 by unknown mechanisms demonstrating a dual positive effect as therapeutic cancer agents.

The studies herein indicate that Skp2E3LIs have a dual therapeutic function for ECA and other cancers to correct unrestrained proliferation and by possibly blocking metastasis when p27 is aberrantly present in the cytoplasm. Specifically, as depicted in FIG. 18, it is shown that C2 and C20 not only increase nuclear p27 but these Skp2E3LIs also block E2-induced p27 degradation and, putatively, thereby block E2-induced proliferation through the accumulation of nuclear p27. Simultaneously, the specific Skp2E3LIs are shown here to decrease cytoplasmic p27 in both ECC-1 cells and ECA cells. These inhibitors might therefore be effective in E2-induced endometrial carcinogenesis in which p27 is both, degraded in the nucleus or sequestered in the cytoplasm. Furthermore, their effects should be applicable to other human cancers having similar pathology of low levels of p27 and high levels of Skp2/Cks 1 in the nucleus, and/or high cytoplasmic p27. Since there is a need for therapies that specifically target cancer cells and are not cytotoxic for normal cells, Skp2E3LIs might selectively increase nuclear p27 to regulate growth control early in malignant progression when p27 has been shown to be lost in ECA and other cancers (Chu et al., "The Cdk Inhibitor p27 in Human Cancer: Prognostic Potential and Relevance to Anticancer Therapy," *Nat. Rev. Cancer* 8:253-267 (2008), which is hereby incorporated by reference in its entirety). In addition, these inhibitors of Skp2 interaction with p27 allow a chemical genetics approach to pinpoint and interrogate a single pathway linked to p27 and loss of growth control. This was not previously possible with general proteasome inhibitors that affect the entire cell machinery. For this same reason, these E3 ligase inhibitors represent a key advance in the use of proteasome inhibitor therapy which have lacked the specificity to be successful as anti-cancer agents (Rico-Bautista & Wolf, "Skipping Cancer: Small Molecule Inhibitors of SKP2-Mediated p27 Degradation," *Chem. Biol.* 19:1497-1498 (2012), which is hereby incorporated by reference in its entirety).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating endometrial cancer in a subject, said method comprising: selecting a subject with endometrial cancer and administering to the subject a compound from the group consisting of

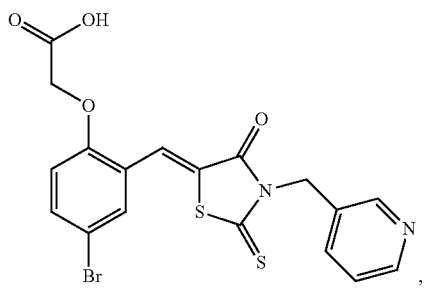

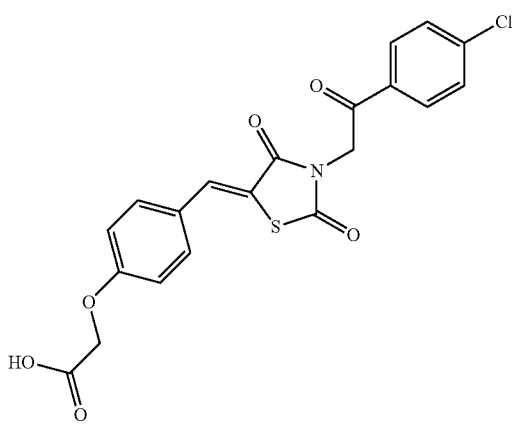

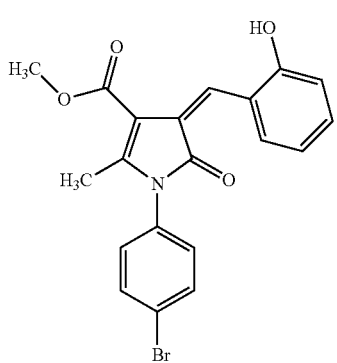

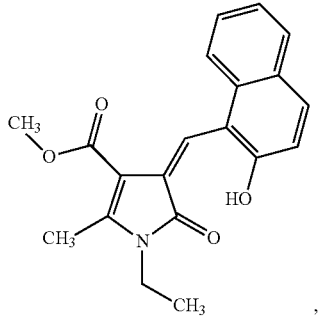

-continued
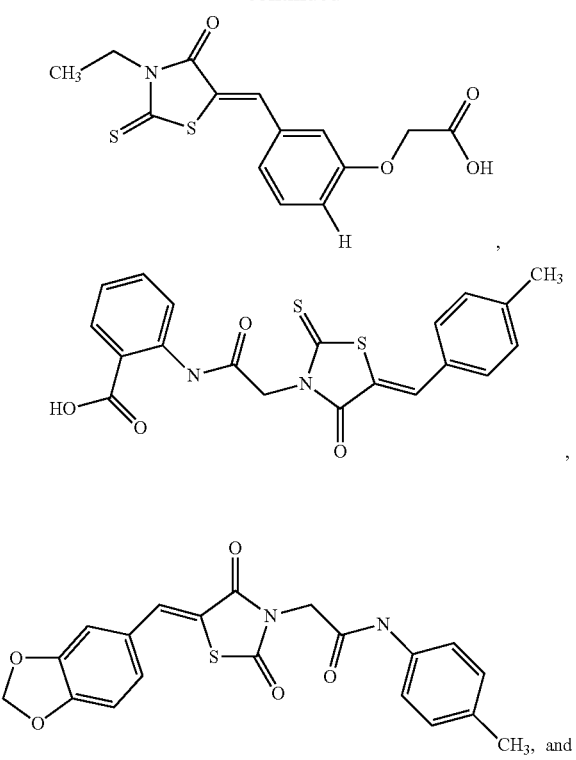
2. The method of claim 1, wherein the compound is selected from
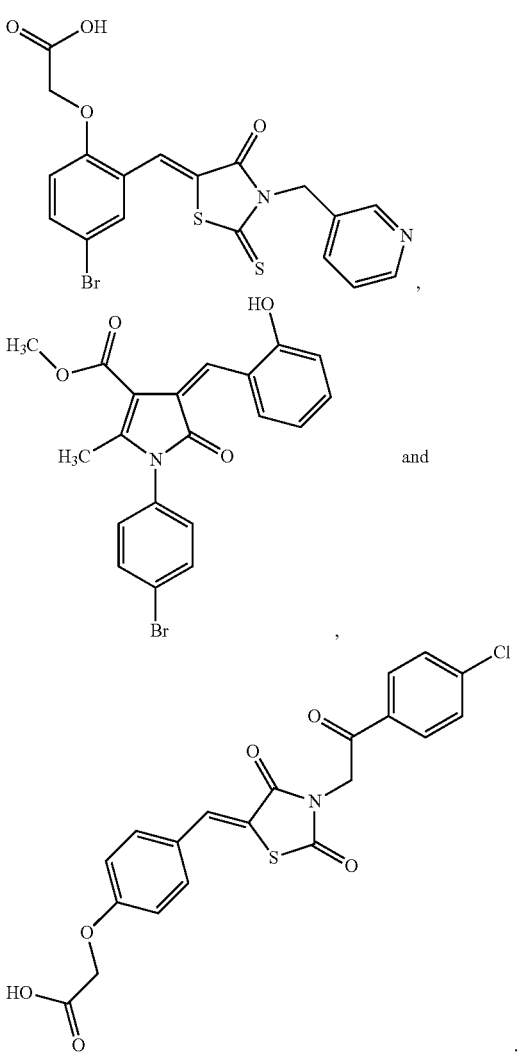
* * * * *

SEQUENCE LISTING

<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: primer p27 F

<400> SEQUENCE: 1
cttgcccgag ttctactaca gac                                            23

<210> SEQ ID NO 2
<211> LENGTH: 23
<212> TYPE: DNA
<213> ORGANISM: Artificial Sequence
<220> FEATURE:
<223> OTHER INFORMATION: primer p27 R

<400> SEQUENCE: 2
caaatgcgtg tcctcagagt tag                                            23

<210> SEQ ID NO 3
<211> LENGTH: 24
<212> TYPE: DNA
<213> ORGANISM: Artificial Sequence
<220> FEATURE:
<223> OTHER INFORMATION: primer Skp2 F

<400> SEQUENCE: 3
tcaactacct ccaacaccta tcac                                           24

<210> SEQ ID NO 4
<211> LENGTH: 21
<212> TYPE: DNA
<213> ORGANISM: Artificial Sequence
<220> FEATURE:
<223> OTHER INFORMATION: primer Skp2 R

<400> SEQUENCE: 4
ggtaccatct ggcacgattc c                                              21

<210> SEQ ID NO 5
<211> LENGTH: 22
<212> TYPE: DNA
<213> ORGANISM: Artificial Sequence
<220> FEATURE:
<223> OTHER INFORMATION: primer Cks1 F

<400> SEQUENCE: 5

```
gagtatcgac atgtcatgct gc                                              22

<210> SEQ ID NO 6
<211> LENGTH: 20
<212> TYPE: DNA
<213> ORGANISM: Artificial Sequence
<220> FEATURE:
<223> OTHER INFORMATION: primer Cks1 R

<400> SEQUENCE: 6
tctttggttt cttgggtagt                                                 20

<210> SEQ ID NO 7
<211> LENGTH: 26
<212> TYPE: DNA
<213> ORGANISM: Artificial Sequence
<220> FEATURE:
<223> OTHER INFORMATION: primer Cdh1 F

<400> SEQUENCE: 7
gtccaagcac gccaacgagc tggtga                                          26

<210> SEQ ID NO 8
<211> LENGTH: 24
<212> TYPE: DNA
<213> ORGANISM: Artificial Sequence
<220> FEATURE:
<223> OTHER INFORMATION: primer Cdh1 R

<400> SEQUENCE: 8
gacacagact cctttgtcga acgg                                            24

<210> SEQ ID NO 9
<211> LENGTH: 20
<212> TYPE: DNA
<213> ORGANISM: Artificial Sequence
<220> FEATURE:
<223> OTHER INFORMATION: primer PR F

<400> SEQUENCE: 9
ggtctacccg ccctatctca                                                 20

<210> SEQ ID NO 10
<211> LENGTH: 20
<212> TYPE: DNA
<213> ORGANISM: Artificial Sequence
<220> FEATURE:
<223> OTHER INFORMATION: primer PR R

<400> SEQUENCE: 10
ggcttggctt tcatttggaa                                                 20

<210> SEQ ID NO 11
<211> LENGTH: 25
<212> TYPE: DNA
<213> ORGANISM: Artificial Sequence
<220> FEATURE:
<223> OTHER INFORMATION: primer glycodelin F

<400> SEQUENCE: 11
cacgctgctc gatactgact acgac                                           25

<210> SEQ ID NO 12
<211> LENGTH: 23
<212> TYPE: DNA
<213> ORGANISM: Artificial Sequence
```

```
<220> FEATURE:
<223> OTHER INFORMATION: primer glycodelin R

<400> SEQUENCE: 12
tggaggcgga ggtgagctag aaa                                       23

<210> SEQ ID NO 13
<211> LENGTH: 20
<212> TYPE: DNA
<213> ORGANISM: Artificial Sequence
<220> FEATURE:
<223> OTHER INFORMATION: primer actin F

<400> SEQUENCE: 13
atcatgtttg agaccttcaa                                           20

<210> SEQ ID NO 14
<211> LENGTH: 20
<212> TYPE: DNA
<213> ORGANISM: Artificial Sequence
<220> FEATURE:
<223> OTHER INFORMATION: primer actin R

<400> SEQUENCE: 14
catctcttgc tcgaagtcca                                           20
```